(12) United States Patent
Martz et al.

(10) Patent No.: US 7,988,699 B2
(45) Date of Patent: Aug. 2, 2011

(54) ADJUSTABLE INSTRUMENTATION FOR SPINAL IMPLANT INSERTION

(75) Inventors: Erik O. Martz, Savage, MN (US); Jo-Wen Lin, Philadelphia, PA (US); David Chow, West Chester, PA (US); Daniel Rosenthal, Short Hills, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 871 days.

(21) Appl. No.: 11/253,410

(22) Filed: Oct. 19, 2005

(65) Prior Publication Data

US 2006/0095043 A1    May 4, 2006

Related U.S. Application Data

(60) Provisional application No. 60/620,172, filed on Oct. 19, 2004.

(51) Int. Cl.
*A61B 17/58* (2006.01)
(52) U.S. Cl. .......................................................... 606/99
(58) Field of Classification Search ............... 606/79–85, 606/86 R, 99
See application file for complete search history.

(56) References Cited

U.S. PATENT DOCUMENTS

| | | | |
|---|---|---|---|
| 695,783 | A | 3/1902 | Bean |
| 740,937 | A | 10/1903 | Smith |
| 1,359,164 | A | 11/1920 | Lo Guidice |
| 2,503,373 | A * | 4/1950 | Browning et al. ........... 81/177.7 |
| 2,631,585 | A | 3/1953 | Siebrandt |
| 3,254,649 | A | 6/1966 | Wood |
| 3,439,423 | A | 4/1969 | Sedwick |
| 3,844,291 | A | 10/1974 | Moen |
| 3,848,601 | A | 11/1974 | Ma et al. |
| 4,349,921 | A | 9/1982 | Kuntz |
| 4,385,628 | A | 5/1983 | Straith |
| 4,697,586 | A | 10/1987 | Ganzale |
| 4,736,738 | A | 4/1988 | Lipovsek et al. |
| 4,878,915 | A | 11/1989 | Brantigan |

(Continued)

FOREIGN PATENT DOCUMENTS

EP    0 646 366 A1    4/1995

(Continued)

OTHER PUBLICATIONS

*Campbell's Operative Orthopaedics*, vol. 5, 8$^{th}$ Ed., pp. 3505-3509, Mosby Year Book, Inc. (1992).

(Continued)

*Primary Examiner* — Nicholas Woodall

(57) ABSTRACT

A plurality of differently configured bone spinal implants for insertion in a spine have a cylindrical bore for receiving an insertion head stud. A plurality of instruments are disclosed each of which have a first connection element which is either a male or female member such as e.g., a ball and socket, a cylinder and socket and so on for forming either a stationary or articulating interchangeable joint for a plurality of disc processing heads or implant insertion heads. The plurality of disc space processing heads or implant insertion heads have a complementary second joint member for interchangeable attachment to the first connection element. The implant insertion heads or disc processing heads have different configurations for different shaped implants. Different instrument insertion or disc processing heads such as implant inserters, impactors, rasps, distractors, curettes, rongeur, and so on are disclosed as being interchangeable with a common instrument in which articulating or fixed joints are provided the interchangeable heads.

18 Claims, 40 Drawing Sheets

U.S. PATENT DOCUMENTS

| | | | |
|---|---|---|---|
| 4,950,273 A * | 8/1990 | Briggs | 606/113 |
| D312,309 S | 11/1990 | Michelson | |
| 5,192,327 A | 3/1993 | Brantigan | |
| 5,256,064 A | 10/1993 | Riihimaki et al. | |
| 5,385,471 A | 1/1995 | Chuen | |
| 5,423,855 A | 6/1995 | Marienne | |
| 5,425,772 A | 6/1995 | Brantigan | |
| 5,441,059 A | 8/1995 | Dannan | |
| 5,443,514 A | 8/1995 | Steffee | |
| 5,454,827 A | 10/1995 | Aust et al. | |
| 5,499,984 A * | 3/1996 | Steiner et al. | 606/80 |
| 5,499,985 A * | 3/1996 | Hein et al. | 606/99 |
| 5,522,899 A | 6/1996 | Michelson | |
| 5,549,637 A | 8/1996 | Crainich | |
| 5,554,191 A | 9/1996 | Lahille et al. | |
| 5,564,922 A * | 10/1996 | Rosa et al. | 433/173 |
| 5,571,137 A | 11/1996 | Marlow et al. | |
| 5,575,805 A | 11/1996 | Li | |
| 5,674,225 A * | 10/1997 | Muller | 606/99 |
| 5,752,973 A * | 5/1998 | Kieturakis | 606/207 |
| 5,776,199 A | 7/1998 | Michelson | |
| 5,782,830 A | 7/1998 | Farris | |
| 5,782,919 A | 7/1998 | Zdeblick et al. | |
| 5,810,864 A | 9/1998 | Schaller | |
| 5,810,878 A | 9/1998 | Burel et al. | |
| 5,814,084 A | 9/1998 | Grivas et al. | |
| 5,836,958 A * | 11/1998 | Ralph | 606/160 |
| 5,860,995 A | 1/1999 | Berkelaar | |
| 5,906,616 A | 5/1999 | Pavlov et al. | |
| 5,910,141 A | 6/1999 | Morrison et al. | |
| 5,925,077 A * | 7/1999 | Williamson et al. | 623/22.34 |
| 5,946,988 A | 9/1999 | Metz-Stavenhagen | |
| 5,957,836 A | 9/1999 | Johnson | |
| 5,968,098 A | 10/1999 | Winslow | |
| 5,984,967 A | 11/1999 | Zdeblick et al. | |
| 5,989,289 A | 11/1999 | Coates et al. | |
| 6,004,326 A | 12/1999 | Castro et al. | |
| 6,033,405 A | 3/2000 | Winslow et al. | |
| 6,033,438 A | 3/2000 | Bianchi et al. | |
| 6,036,692 A | 3/2000 | Burel et al. | |
| 6,053,933 A | 4/2000 | Balazs et al. | |
| 6,066,174 A | 5/2000 | Farris | |
| 6,099,483 A | 8/2000 | Palmer et al. | |
| 6,105,473 A * | 8/2000 | Huang | 81/177.75 |
| D439,338 S | 3/2001 | Huttner | |
| 6,277,149 B1 | 8/2001 | Boyle et al. | |
| 6,309,403 B1 | 10/2001 | Minor et al. | |
| 6,425,920 B1 | 7/2002 | Hamada | |
| 6,436,101 B1 | 8/2002 | Hamada | |
| 6,500,206 B1 | 12/2002 | Bryan | |
| 6,511,509 B1 | 1/2003 | Ford et al. | |
| 6,569,168 B2 | 5/2003 | Lin | |
| 6,579,318 B2 | 6/2003 | Varga et al. | |
| 6,610,065 B1 | 8/2003 | Branch et al. | |
| 6,666,866 B2 | 12/2003 | Martz et al. | |
| 6,746,454 B2 | 6/2004 | Winterbottom et al. | |
| 6,911,045 B2 | 6/2005 | Shimp | |
| 2001/0010001 A1 | 7/2001 | Michelson | |
| 2001/0010002 A1 | 7/2001 | Michelson | |
| 2001/0021853 A1 | 9/2001 | Heckele et al. | |
| 2002/0016592 A1 | 2/2002 | Branch et al. | |
| 2002/0016633 A1 | 2/2002 | Lin | |
| 2002/0019637 A1 | 2/2002 | Frey et al. | |
| 2002/0022845 A1 | 2/2002 | Zdeblick et al. | |
| 2002/0065558 A1 | 5/2002 | Varga et al. | |
| 2002/0068941 A1 | 6/2002 | Hanson et al. | |
| 2002/0072752 A1 | 6/2002 | Zucherman et al. | |
| 2002/0077632 A1 | 6/2002 | Tsou | |
| 2002/0107523 A1 | 8/2002 | Naughton et al. | |
| 2002/0111679 A1 | 8/2002 | Zucherman et al. | |
| 2002/0138143 A1 | 9/2002 | Grooms et al. | |
| 2002/0156530 A1 | 10/2002 | Lambrecht et al. | |
| 2002/0165612 A1 | 11/2002 | Gerber et al. | |
| 2003/0028249 A1 | 2/2003 | Baccelli et al. | |
| 2003/0036764 A1 | 2/2003 | Hamada | |
| 2003/0040798 A1 | 2/2003 | Michelson | |
| 2003/0060886 A1 | 3/2003 | Van Hoeck et al. | |
| 2003/0069586 A1 * | 4/2003 | Errico et al. | 606/99 |
| 2003/0125739 A1 | 7/2003 | Bagga et al. | |
| 2003/0130667 A1 | 7/2003 | Lin | |
| 2003/0130737 A1 | 7/2003 | McGahan | |
| 2003/0139815 A1 | 7/2003 | Grooms et al. | |
| 2004/0098129 A1 | 5/2004 | Lin | |
| 2004/0162562 A1 | 8/2004 | Martz | |
| 2004/0243242 A1 | 12/2004 | Sybert et al. | |
| 2004/0249377 A1 | 12/2004 | Kaes et al. | |
| 2005/0027360 A1 * | 2/2005 | Webb et al. | 623/17.11 |
| 2005/0038511 A1 | 2/2005 | Martz et al. | |
| 2005/0096745 A1 * | 5/2005 | Andre et al. | 623/17.11 |
| 2005/0240188 A1 | 10/2005 | Chow et al. | |
| 2005/0251146 A1 | 11/2005 | Martz et al. | |
| 2006/0149376 A1 | 7/2006 | Shimp et al. | |
| 2007/0073293 A1 | 3/2007 | Martz et al. | |

FOREIGN PATENT DOCUMENTS

| | | |
|---|---|---|
| EP | 1 138 285 A1 | 10/2001 |
| FR | 2 795 945 | 12/2001 |
| WO | WO 90/00037 | 1/1990 |
| WO | WO 93/18713 | 9/1993 |
| WO | WO 00/44288 | 8/2000 |
| WO | WO 01/41681 | 6/2001 |

OTHER PUBLICATIONS

Cloward, M.D., Ralph B., *Description of a New Instrument, The Vertebral Spreader*, Lumbar Intervertebral Disc Surgery, vol. 32, No. 5, pp. 852-857.

Crock, Henry V., *Practice of Spinal Surgery*, pp. 64-92, Springer-Vertag/Wein, New York (1983).

Fraser, Robert D., MBBS, MD, FRACS, *Spine*, vol. 20, No. 245, pp. 1675-1775, Lippincott-Raven Publishers (1995).

Hirabayashi, Kiyoshi, *Lumbar Interbody Fusion*, pp. 127-131, Aspen Publishers, Inc., Rockville, Maryland (1989).

Janssen, Michael E. et al., *Biological Cages*, Eur Spine J (Suppl1), S102-S109, Springer-Verlag (2000).

Johnson & Johnson Professional, Inc., *Codman Surgical Products Catalog*, 1996.

Koh, Charles H., M.D. Facog, Frcog, U="The Colpotomy Optimized Hysterectomy", Blairden, Lenexa, Kansas.

LifeNet Product Information , *VG2 Interbody Bone Grafts*, 2000.

Miltex Instrument Company, Inc. *Miltex Surgical Instruments*, 1986.

White III, MD, Augustus A., DMed Sci, *Clinical Biomechanics of the Spine*, 2nd Ed., pp. 547-563, Lippincott-Raven, Philadelphia.

* cited by examiner

ADJUSTABLE INSTRUMENTATION FOR SPINAL IMPLANT INSERTION

This application claims the benefit of provisional application Ser. No. 60/620,172 filed Oct. 19, 2004, entitled "Adjustable Instrumentation For Spinal Implant Insertion," incorporated by reference herein in its entirety.

FIELD OF THE INVENTION

This invention relates to spinal intervertebral fusion implant insertion instruments for insertion of the implant into the intervertebral disc space.

DESCRIPTION OF RELATED ART

Cross Reference to Related Applications and Patents

Of interest are commonly owned copending provisional application Ser. No. 60/340,734 filed Oct. 30, 2001 and Ser. No. 60/372,972 filed Apr. 16, 2002, both in the name of John Winterbottom et al., both applications corresponding to U.S. utility application Ser. No. 10/282,552 filed Oct. 29, 2002 entitled Bone Implant and Insertion Tools and PCT application Ser. No. PCT/US02/34466 filed Oct. 28, 2002, Ser. No. 10/086,041 entitled Spinal Intervertebral Implant Insertion Tool filed Oct. 25, 2001 in the name of Erik Martz et al. and Ser. No. 10/046,866 (now US Pub. No. US 2002/0058950A1) entitled Implant Insertion Tool filed Jan. 15, 2002 in the name of John M. Winterbottom et al., Ser. No. 60/425,941 filed Nov. 13, 2002 in the name of Jo Wen Lin entitled Spinal Implant Insertion Adjustment Instrument and Implants for use Therewith and Ser. No. 09/705,377 entitled Spinal intervertebral Implant filed Nov. 3, 2000 in the name of Lawrence A. Shimp et al., and U.S. Pat. No. 6,277,149, all incorporated by reference herein.

During spinal surgery, the surgeon may approach the spine from a variety of different orientations. One orientation uses the posterior approach, another uses the anterior approach and others may approach laterally, posterior or anterior or antero-lateral, an angle somewhere between the anterior and lateral approaches.

U.S. Pat. No. 5,772,661 to Michelson discloses methods and instrumentation for surgical correction of the human thoracic and lumbar spine from the antero-lateral aspect of the spine.

Henry V. Crock, *Practice of Spinal Surgery*, pages 64-92, 1983, New York, N.Y., discloses the technique of anterior interbody fusion. Fig. 2.34 illustrates the use of retractors and swabs to protect the great vessels. Fig. 2.35 shows the $L_4L_5$ levels. Figs. 2.38, 2.42 and 2.43 illustrate some of the instruments used. Figs. 2.46a and b illustrate some of the orientations of the grafts.

Charles H. Koh, *The Colpotomy Optimized Hysterectomy, A New System for Total Laparoscopic Hysterectomy Using the Rowden Uterine Manipulator Injector (RUMI) with the Koh Colpotomizer and Pneumo-occluder*. The photos 1-12 and the associated text show and describe the use of scissors and various other surgical instruments.

PCT International Publication Number WO 93/18713 to Hodgson discloses a uterine retractor medical device for positioning and controlling the uterus within the abdominal cavity. The uterine retractor includes an elongated actuator grip. One end of the actuator grip includes a handle grip with a trigger, and the other end of the actuator handle mounts a retractor housing. The retractor housing is fixed to a support bar and supports a retractor pivot for movement about an axis substantially perpendicular to the support bar. Actuation of the trigger moves a retractor finger which is inserted within the uterus and thus imparts movement to the uterus allowing placement for medical procedures.

U.S. Pat. No. 5,522,899 to Michelson discloses an implant insertion instrument in which the instrument has an implant engagement face that is concave that engages a convex face of the implant and includes an extension for engaging a depression in the implant face. The implant appears to be inserted from the anterior of the spine. The implant is shown as being inserted along the anterior-posterior axis of the spine.

U.S. Pat. No. 4,349,921 illustrates a cervical spinal implant and insertion instrument. The implant has a threaded bore and the instrument has a threaded stud which mates with the bore for inserting the implant along the posterior-anterior axis.

U.S. Pat. No. 4,878,915 to Brantigan illustrates the PLIF approach (posterior lumbar interbody fusion). He too uses a threaded implant and mating threaded insertion instrument for insertion of the implant along the posterior-anterior axis.

U.S. Pat. Nos. 5,192,327 and 5,425,772 illustrate implants with threaded bores for insertion with threaded insertion instruments. These insert the implant straight into the disc space along a given axis and require the implant to have the desired shape and orientation for such insertion direction.

U.S. Pat. No. 5,645,598 shows an implant with an opening for receiving a screwdriver for inserting the implant.

U.S. Pat. No. 5,957,836 shows a paddle type spinal vertebral distractor.

U.S. Pat. No. 5,683,469 discloses a tibial trial prosthesis and bone preparation system.

U.S. Pat. No. 5,256,064 discloses a dental prosthesis placement instrument.

U.S. Pat. No. 6,261,296 to Aebi et al. discloses a spinal disc distractor.

U.S. Pat. No. 6,136,004 discloses a surgical nail forceps.

U.S. Pat. No. 6,120,506 discloses instrumentation for insertion of a lordotic spinal implant.

U.S. Pat. No. 6,500,206 to Bryan discloses instruments sets for inserting a spinal intervertebral implant. The instruments include inserters, impactors, chisels, scrapers and vertebrae spreaders. Each instrument has a corresponding handle and shaft.

U.S. Pat. No. 6,096,038 to Michelson discloses various instruments for processing the disc space of vertebrae and for insertion of an implant into the processed disc space. Different instruments and configurations are used with distractors, inserters and so on in the disclosed process.

US patent publication 2001/00221853 discloses a surgical instrument for applying implants into the space between adjacent vertebrae. The instrument comprises a shank to which an implant holder is pivotally mounted and can be fixed in position. The implant holder is conical and threaded. The holder is threaded to an implant with a complementary thread. The holder is fixed in an angular orientation by an adjustment of an axially displaceable rod. This instrument is especially adapted to mate with a complementary threaded implant. No other instruments are disclosed that are interchangeable with the implant inserter.

US patent publication 2002/0019637 discloses devices, implants and techniques for a posterior lateral disc space approach. The instruments include spreaders, reamers, cutters, scrapers, chisels, rasps, pushers and implant inserters.

US patent publications 2002/0022845 and 2002/0016592 illustrate still other instruments and implants for spinal surgery interbody fusion.

US patent publication 2002/0111679 discloses apparatus and method for determining implant size. A trial sizer is pivotally mounted to an elongated body so that as the sizer is urged between adjacent spinous process, a physician may rotate the elongated body through a range of motion and not place any torsional forces upon the sizer. Different trial sizers are used to determine the space between adjacent spinous process.

US patent publication 2002/0016592 discloses interbody fusion grafts and instruments including inserters and chisels.

U.S. Pat. No. 6,610,065 to Branch et al. discloses a variety of spinal implant surgical instrumentation including chisels, scrapers, and so on.

U.S. Pat. No. 5,599,279 discloses surgical instruments and method useful for endoscopic spinal procedures. Disclosed is a vertebrae spreader for use in the anterior approach. The spreader includes a handle and an actuating member. A vertebrae spreading mechanism includes a pair of serrated spreading arms and is actuated by the actuating member. The mechanism includes a collar actuating member and a translatable inner cylindrical member with an angled camming slot or cooperating with a camming pin, the slot for locking the pin in arms open position. An actuating rod moves the vertebrae spreading mechanism between open and closed positions. A linkage mechanism connects the spreading mechanism to the rod. The arms have an angled camming slot to permit movement of the vertebrae spreading members to their open and closed positions. Structure is provided to translate the longitudinal reciprocating motion of the rod to pivotal motion of the spreading arms about transverse pins. The arms include teeth to prevent slipage. An alternative embodiment discloses spreading arms that are moved in reciprocal sliding motion by a rack and pinion system with each spreading member connected to a different rack. In a further embodiment, axial displacement of a rod member pivots the spreading members via a linkage arrangement connected between the rod and the spreading members. These embodiments are not disclosed as being interchangeable nor is the mechanisms disclosed as useful with other surgical processing tools.

US patent publication 2002/0072752 discloses interspinous process implant sizer and distractor with a split head and size indicator and method.

U.S. Pat. No. 6,099,311 discloses an abutment delivery system for retaining and delivering dental implant components. The system includes a member that has a plurality of multi-size stepped down portions for hands-off insertion into and frictional engagement with various dental implant components. The member may be selectively attached and pivotally attached to a handle.

Paul M. Lin et al. in a text entitled *Lumbar Interbody Fusion*, chapter II directed to anterior lumbar spinal body fusion pages 127-131, Aspen publishers, Rockville, Md. 1989 discloses instrumentation and procedure for anterior spinal fusion.

An article in Spine, Vol. 20, Number 24S, pp. 167S-177S entitled *Interbody, Posterior, Combined Lumbar Fusions*, discloses posterior, posterior lateral interbody fusions of interest.

Cloward, in an early work in 1952, entitled *Lumbar Intervertebral Disc Surgery*, Surgery, Vol. 32, No. 5, Nov. 1952, discloses lumbar intervertebral disc surgery employing a spreader.

Janssen et al. in an article entitled Biological Cages Eur Spine Jour (2000) 9 (Supp 1) pp. S102-109 discloses the femoral ring allograft and PLIF spacer used for anterior lumbar interbody fusion and posterior lumbar interbody fusion.

Other articles of interest in this field include *Clinical Biomechanics of the Spine*, by White et al. second ed. 1990, pp. 547-563, Lippincott-Raven, New York, N.Y. showing various implant orientations, Campbell's Operative Orthopedics, Vol. Five, eighth ed, 1992, pp. 3505-3509 showing lateral approach and anterior approach spinal surgery, and a text Clinical Orthopaedics, Section II, General Orthopaedics, *Anterior Lumbar Interbody Fusion* by H. V. Crock, Lippincott Co.

Of interest are catalogs by DePuy Acromed VG2 Interbody Bone Grafts, 2000; Acromed Spine Tools Anterior Endoscopic Thoracolumbar Instruments, 8/96, showing various instruments for lumbosacral discectomy and fusion, Miltex Surgical Instruments, 1986 and Codman Surgical Products Catalog 1996, illustrating various surgical instruments.

However, the problem with the suggested techniques and instrumentation of the prior art as discussed above is that separate costly instruments are required for each different surgical function. For example, spreaders, chisels, rasps, rongeurs, curettes, implant insertion instruments, trials, and so on require a separate tool including a handle, a shaft and an instrument head for performing a given task. As a result as shown in the various catalogs mentioned above as well in several of the patents noted, kits of instruments are supplied to the surgeons including instruments for performing the various surgical processes required by spinal implant implantation. These instruments are costly. In addition, each instrument has limited use for a given approach and is difficult to use for other different approaches. As a result different spinal approaches have corresponding unique instruments for that particular technique.

In addition, the surgeon using a fixed angled instrument possibly would have difficulty in some situations displacing the instrument in a relatively narrow space.

A need is seen by the present inventors for a solution to this problem. A need is seen in particular for instrumentation that is less costly and more versatile for various surgical techniques than present instrumentation and that is useful for use in tight surgical spaces.

SUMMARY OF THE INVENTION

According to an embodiment of the present invention, a surgical instrument is provided for processing an intervertebral disc space and/or for insertion of a spinal implant into the processed space. The instrument comprises a shaft having a first axis; a first joint element coupled to the shaft; and at least two different heads for the processing and/or insertion. Each of the different heads for selective attachment to the shaft, and each head having a second axis and a second joint element which mates with the first joint element. The first and second joint elements forming a joint for attaching each selected head to the shaft. In one aspect, the joint and the elements are configured for permitting positioning the second axis of each selected head in any of a plurality of different orientations relative to the first axis.

In a further aspect, the first and second joint elements are mating complementary first and second articulation elements to permit articulation of the head relative to the shaft.

In a further aspect, a connection arrangement is secured to the shaft for temporarily fixedly securing any of the selected heads to the shaft.

In a still further aspect, the connection arrangement secures the selected heads in any one of selected different orientations relative to the first axis.

In a further aspect, the joint elements are configured for permitting each selected head to be positioned at any of a plurality of angular orientations relative to the first axis.

In a further aspect, the joint elements are configured to permit the second axis of the different heads to be positioned parallel to and spaced from the first axis.

In a further aspect, the first articulation element comprises one of a ball, cylinder, or socket and the second articulation element has a configuration complementary to the respective one ball, cylinder or socket for releasably and movably mating to the respective one ball, cylinder or socket.

In a still further aspect, the cylinder or ball is a separate piece with respect the shaft and head for mounting in a mating socket in each of the shaft and head.

In a further aspect, the cylinder or ball is one piece and integral with the corresponding one of the shaft and head.

In a further aspect, the head has a distal end opposite the second articulation element. The distal end has a distal end wall and includes a cantilevered side wall extending from the distal end wall. A stud is attached to the distal end wall thereto and extends substantially parallel to the cantilevered side wall.

In a further aspect, a connection arrangement is secured to the shaft for temporarily fixedly securing any of the selected heads to the shaft wherein the connection arrangement includes a rod coupled to the shaft, a first articulation element being coupled to the rod, the connection arrangement including a plurality of resilient fingers formed in the shaft or head for permitting the one ball or cylinder of one of the elements to be received in and secured to the socket of the other of the elements and a rod displacement member attached to the shaft for displacing the rod relative to the first axis to temporarily fixedly secure the head to the shaft.

In a further aspect, the connection arrangement includes a sleeve coupled to the shaft, the first articulation element being coupled to the shaft, the connection arrangement including a plurality of resilient fingers formed in the shaft and defining the one socket, ball or cylinder, displacement of the sleeve for displacing the fingers to either grip or release the one ball or cylinder in the one socket.

In a further aspect, the first or the second articulation element includes an engagement member for releasably engaging the other articulation element, and the engagement member is adapted to allow angular positioning between the first and second articulation elements.

In a further aspect, both the first and the second articulation elements include mating ratchet teeth arranged in an arc. The first and second articulation elements are incrementally adjustable at a plurality of angles relative to each other and the shaft by selectively mating the ratchet teeth of the first and second articulation elements.

In a further aspect, the at least two different heads are selected from the group consisting of any two different head configurations, the configurations forming categories, each category having one or more different configurations, the categories including a chisel, an implant gripping head, an implant impacting head, an implant inserter, a rasp, a distractor, a trial, a curette and a rongeur.

In a further aspect, the at least two different heads are in the same or different categories.

In a further aspect, the shaft includes a plurality of shaft sections with adjacent sections interconnected by a corresponding articulating joint, each of the heads for selective attachment to a first shaft section.

In a further aspect, the corresponding articulating joint comprises a convex surface on one section and a concave complementary surface on the mating adjacent section.

In a further aspect, the at least two different heads and the first shaft section have complementary surface features for articulating mounting of either of the heads on the first shaft section.

In a further aspect, a spinal implant insertion or intervertebral space processing instrument head for an instrument has a shaft comprising a body having first and second ends and defining a longitudinal axis; a surface adjacent to the first end for the space processing or implant insertion; and one of a ball, cylinder or socket adjacent to the second end for attachment to a mating insertion or intervertebral space processing instrument shaft.

In a further aspect, the head is an implant inserter and the body has a first surface at the first end for mating with and abutting a spinal implant surface.

In a further aspect, the body includes any one of the group consisting of an implant inserter, an implant impactor, a chisel, a rasp, a trial, a curette, a rongeur and a distractor.

The heads and instruments are further provided in an additional plurality of different embodiments as disclosed in the accompanying drawings.

BRIEF DESCRIPTION OF THE DRAWINGS

FIGS. 3 and 4 are respective side elevation and side elevation sectional views of the instrument of FIG. 1 wherein FIG. 4 is taken along lines 4-4 of FIG. 3;

FIG. 33 is a view similar to the view of FIG. 32 with a portion of the shaft and the implant insertion head in section;

FIG. 110 is a fragmented side elevation view of a portion of the trigger of the embodiment of FIG. 106 taken at region 9a;

DETAILED DESCRIPTION OF THE PREFERRED EMBODIMENT(S)

Figure 1:
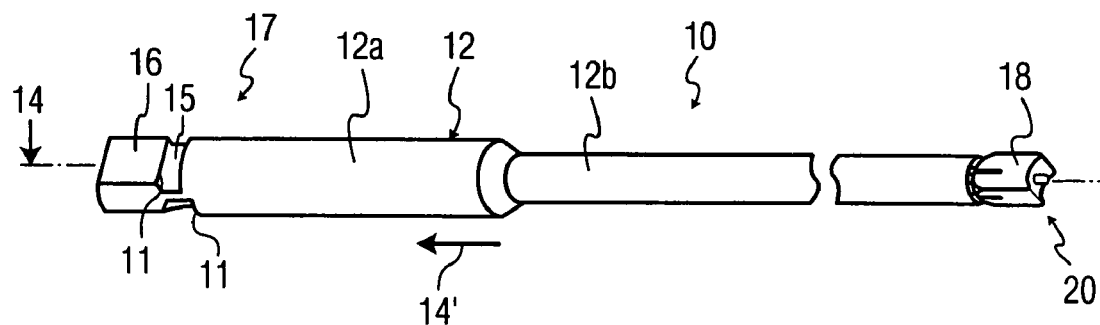
FIG. 1 is an isometric view of a spinal implant insertion instrument according to an embodiment of the present invention.
Figure 3:
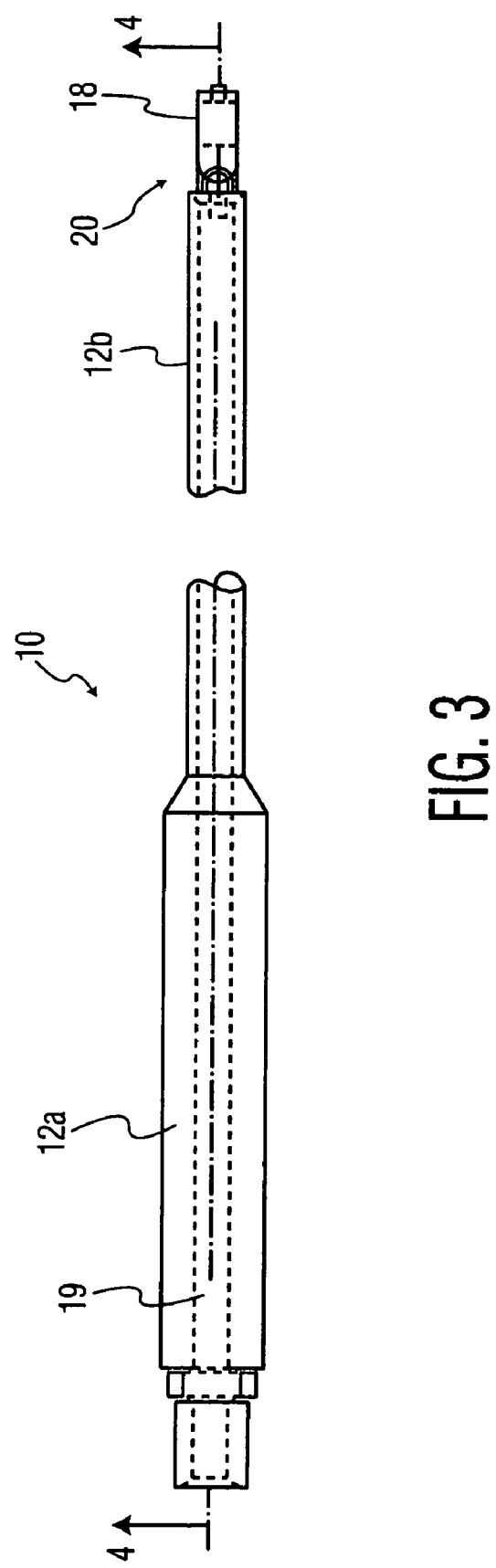
Figure 4:
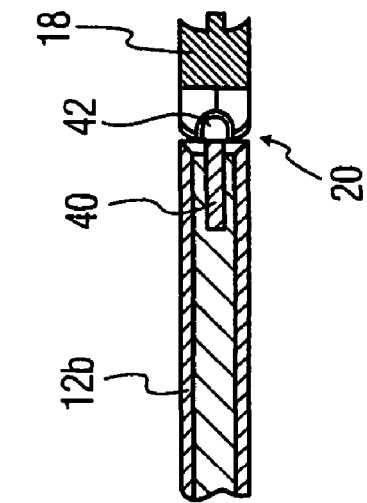
Figure 4:
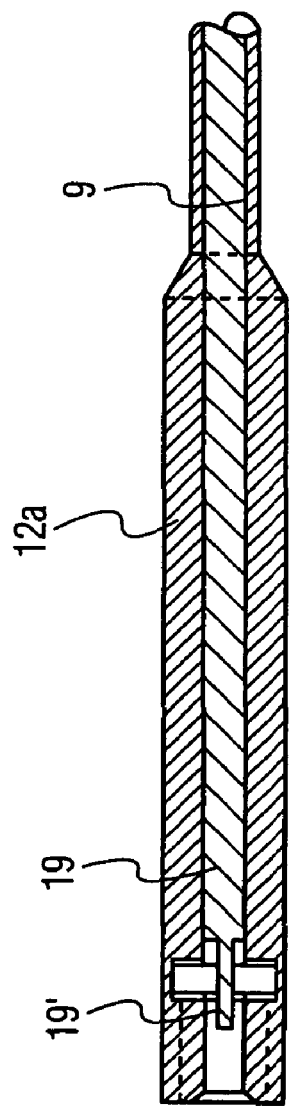
Figure 5:
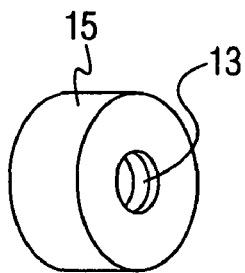
FIGS. 5 and 6 are respective isometric and plan views of a knob and a detailed view of the knob end of the handle used with the embodiment of FIG. 1.
Figure 6:
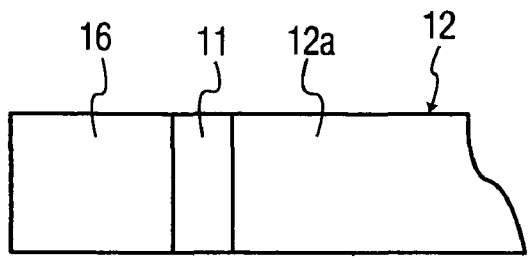
Figure 8:
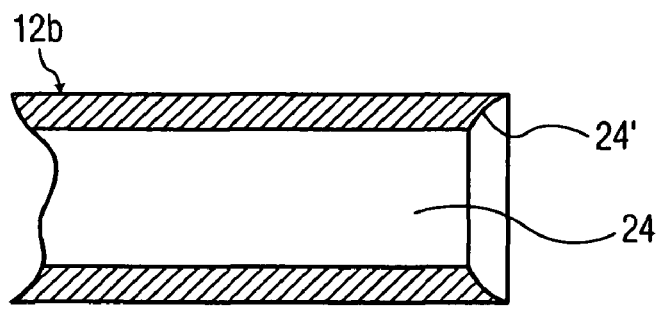
FIG. 8 is a sectional elevation view of the end of the body of the instrument of FIG. 1.

In FIG. 1, surgical instrument 10 comprises an elongated body 12 having a longitudinal axis 14, and a handle extension 16 attached to a cylindrical handle segment 12a of the body 12 at a proximal end 17 of the instrument 10. An implant manipulating and engaging head 18 is attached to a cylindrical shaft segment 12b of the body 12 at a distal end 20 of the instrument 10. The body 12 defines a hollow cavity 24 as shown in FIG. 8. The handle extension 16 and the handle segment 12a define a slot 11 (shown in FIG. 6) therebetween for receiving a knob 15. The knob 15 may be threaded to a mating threaded portion 19' of a shank 19, as shown in FIG. 4. The threaded portion 19' has a smaller diameter than the non-threaded portion of the shank 19. The knob 15 is rotatably threaded to the threaded portion 19' (shown in FIGS. 3 and 4) via a threaded central opening 13 in the knob 15 (shown in FIG. 5). The shank 19 is positioned in the interior 9 of the body 12 and extends through the body 12 from the knob 15 to connection rod 40 and a ball 42 connected to rod 40 and which ball joint connects with the head 18.

The handle segment 12a has a transverse dimension greater than that of the shaft segment 12b to permit ease of gripping by a surgeon during use. The handle segment 12a and body 12 (including handle extension 16, and shaft segment 12b) may be formed of stainless steel, for example, and preferably are cylindrical or, in the alternative, may have other cross section shapes such as square or rectangular, for example. The handle extension 16 may also have flattened surfaces for receiving hammer blows used to manipulate the instrument 10 for manipulating an implant inserted into the intervertebral disc space.

Figure 2:
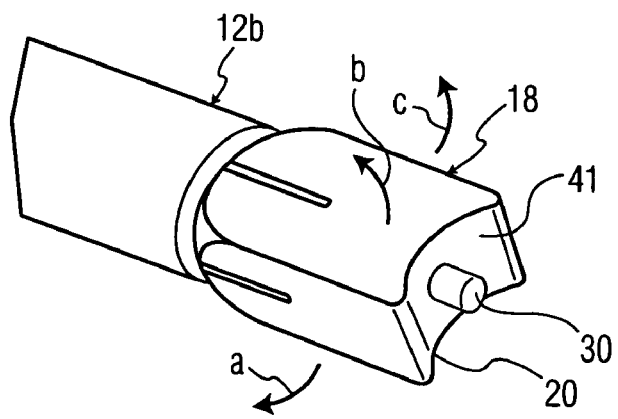
FIG. 2 is a more detailed isometric view of the insertion head of the instrument of FIG. 1.
Figure 9:
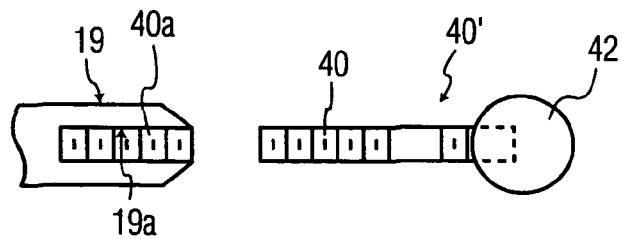
FIG. 9 is a more detailed fragmented side elevation sectional view of a connection rod and articulation joint element in the form of a ball for attaching the head of FIG. 2 to the shaft taken at region 9 of FIG. 11.

In FIG. 2, the head 18 is attached at the distal end 20 of the shaft segment 12b of the body 12 and includes a stud 30 for mating with a hole in an implant (not shown). The shank 19, FIG. 4, extends through the body 12 terminating adjacent to the distal end 20. In FIG. 9, the shank 19 has a threaded bore 19a that receives and mates with the threaded rod 40 attached to the ball 42 of joint 40'.

Figure 7:
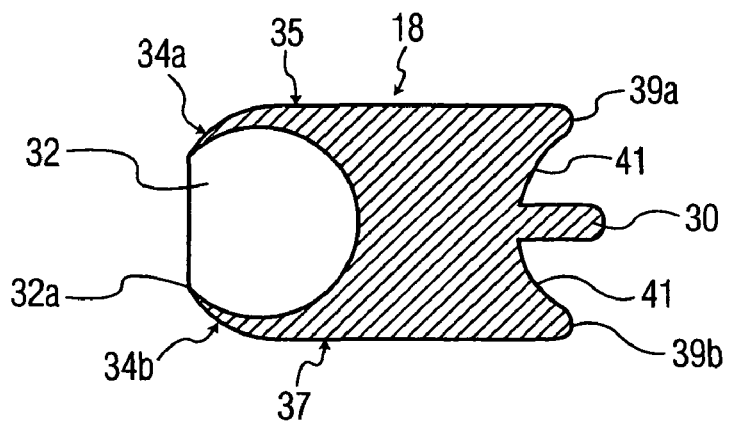
FIG. 7 is a sectional elevation view of the head of FIG. 2.

In FIG. 9, joint 40' comprises the connection rod 40 and an articulation joint element in the preferred form of the ball 42 for removably attaching the head 18 (FIGS. 2, 7). The connection rod 40 includes a threaded portion 40a mating with the threaded bore 19a of the shank 19. The shank 19 is positioned in the hollow cavity 24 of the body 12. The shaft segment 12b of the body 12 and hollow cavity 24 are shown in FIG. 8.

In FIG. 7, the ball 42 affixed to the connection rod 40 mates with a spherical hollow cavity 32 in the head 18 that forms a ball joint socket, the combination of the ball 42 and cavity 32 creating an articulating ball joint. In FIG. 7, the head 18 includes the spherical hollow cavity 32 at one end and an implant receiving stud 30 extending distally at an opposite end. The head 18 further includes top and bottom walls, 35 and 37, respectively. The top and bottom walls 35, 37 terminate at opening 32a to the spherical hollow cavity 32 with convex spherical portions 34a and 34b which mate with and are received in a complementary concave surface at end 20 of the shaft segment 12b. At the opposite end of the head 18, the top and bottom walls 35 and 37 are contiguous with arcuate edges 39a and 39b that extend linearly in and out of the drawing figure, respectively, which edges connect the top and bottom walls 35 and 37 with a concave arcuate implant receiving end wall 41. The implant (not shown) has a complementary surface to the concave wall 41.

The head 18 is interchangable with other implant insertion or disc space processing heads which are adapted to mate with the ball 42 and form a ball joint therewith. In the alternative, the connection rod 40 may include a different articulation joint element, other than the ball 42, such as a cylinder, which in turn connects with a mating joint element such as a cylindrical socket in a head.

Figure 10:
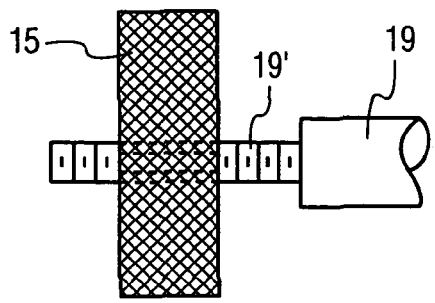
FIG. 10 is a more detailed fragmented side elevation view of the knob of FIG. 5 attached to the end of the connection rod at region 9, FIG. 11.
Figure 12:
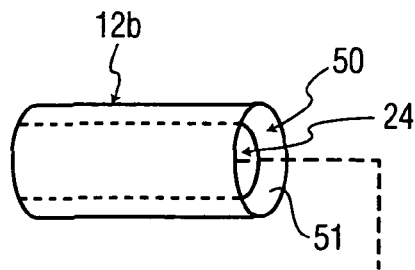
FIG. 12 is an isometric view of the end of the shaft of FIG. 1 for receiving the head of FIG. 2.
Figure 13:
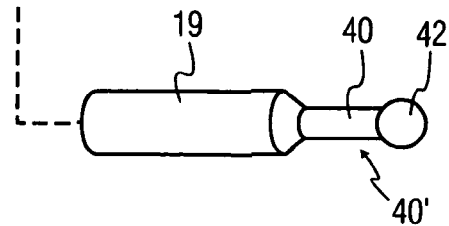
FIG. 13 is a more detailed isometric view of the male articulation joint element attached to the shaft of FIG. 11.

The threaded portion 19' of the shank 19 mates with the threaded central opening 13 of the knob 15, FIG. 10. The shaft segment 12b, FIG. 12, includes the hollow cavity 24 therethrough, which terminates at a distal opening 50. Opening 50 is surrounded by a spherical concave surface 51. The connection rod 40, shown in FIG. 13, connects the ball 42 with the distal end of the shank 19, as shown in cross-section in FIG. 9. The shank 19 passes into the hollow cavity 24 through the opening 50.

Figure 11:
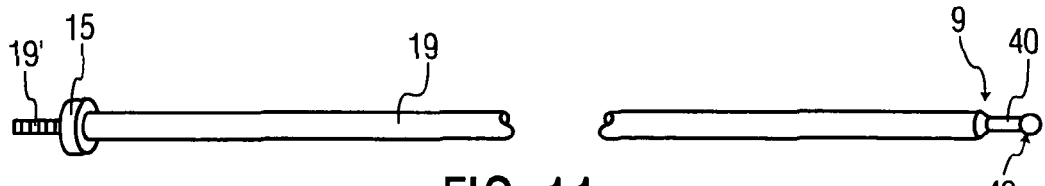
FIG. 11 is a side elevation view of the connection rod assembly used in the embodiments of FIGS. 1, 3 and 4.

The combined shank 19, knob 15, connection rod 40 and ball 42 are shown in FIG. 11. Joint region 9 includes the connection rod 40 and ball 42. FIG. 11 depicts the threaded portion 19' of the shank 19 at the shank 19 proximal end having the knob 15 threaded thereon abutting the shank 19. The knob and connection rod cooperate with the ball joint to form a structure for temporarily fixedly securing the head to the instrument shaft.

Figure 14:
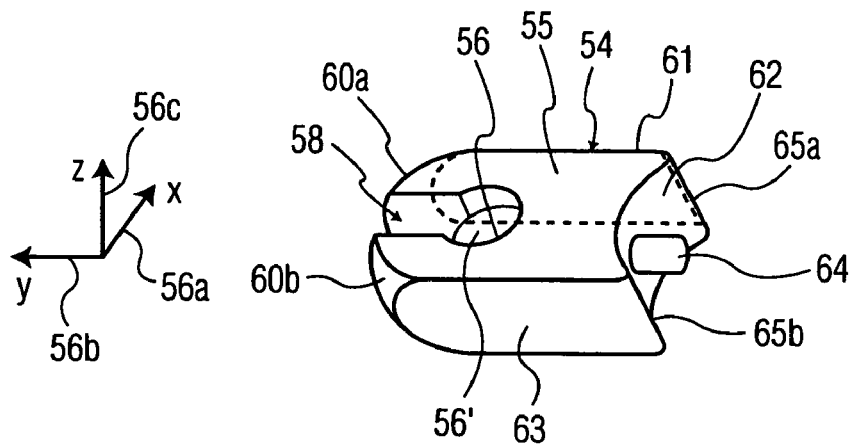
FIG. 14 is an isometric view of an insertion head according to a second embodiment of the present invention.
Figure 15:
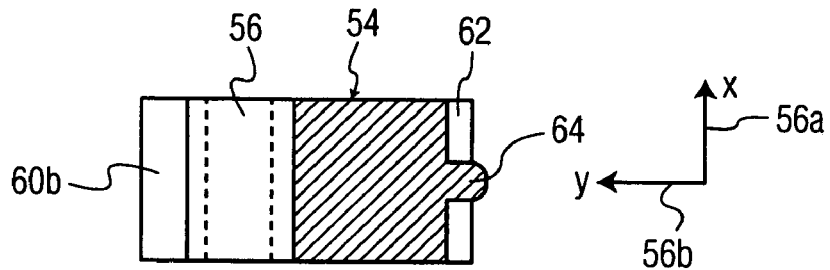
FIG. 15 is a side elevation sectional view of the head of FIG. 14.

In FIGS. 14 and 15, in another embodiment, insertion head 54 includes a body 55 defining a pair of spaced aligned circular cylindrical holes 56, one being shown. The holes 56 communicate with a central spherical cavity 56' forming a joint socket. The holes 56 and cavity 56' communicate with a slot 58 extending through the body 55 along a "z" axis 56c and partially through the body along a longitudinal axis "y" 56b. The holes 56 and cavity 56' receive the ball 42 of the joint 40'. The joint connection is created by insertion of the ball 42 into the socket cavity 56' through the slot 58. The ball 42 and cavity 56' form a ball joint that allows the head 54 to rotate in the plane of the y and z axes. The head can only rotate toward the top and bottom of the drawing figure and not side to side due to the engagement of the rod 40 in the slot 58. The head has side walls 61 and 63 which terminate in convex spherical portions 60*a* and 60*b* which define the opening of the slot 58 at the proximate end of the head. Portions 60*a* and 60*b* mate with concave spherical surface 51, FIG. 12, of the shaft portion 12*b*. At the opposite end of the head from the slot 58, the side walls are contiguous with arcuate edges 65*a* and 65*b* which are linear into and out of the drawing and connect the side walls 61, 63 and a concave distal wall 62 of the head 54. An implant receiving stud 64 extends from the concave distal wall 62 along the longitudinal axis "y" 56*b*, as shown in FIGS. 14 and 15. The wall 62 is shaped to mate with a complementary shaped implant not shown in FIG. 14.

Figure 16:
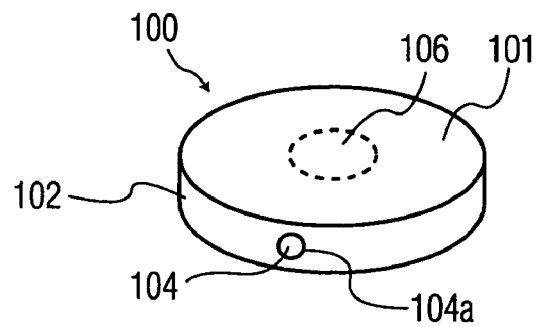
FIGS. 16-24 are various views of different spinal bone implants that may be used with and inserted into a disc space by different instrument insertion heads according to different embodiments of the present invention.

Various spinal bone implants are shown in FIGS. 16-24. An advantage of the instrument according to the present invention is the instrument's adaptability to receive many shapes and sizes of implants and disc space processing heads. All the implant embodiments shown in FIGS. 16-24 include a hole adapted to mate with a stud in an insertion head, for example, the stud 64 of the head 54 shown in FIG. 14, or stud 30 of head 18 shown in FIG. 2. A disc shaped implant 100 is shown in FIG. 16. The implant 100 includes a hole 104 having an opening 104*a* in a circular cylindrical side wall 102 for receiving a stud on the insertion head as discussed above. The wall 102 mates with a complementary shaped concave wall on the mating head. The implant 100 may optionally include a centrally positioned circular hole 106, shown in phantom in FIG. 16 and which may be formed by the medullary canal.

Figure 17:
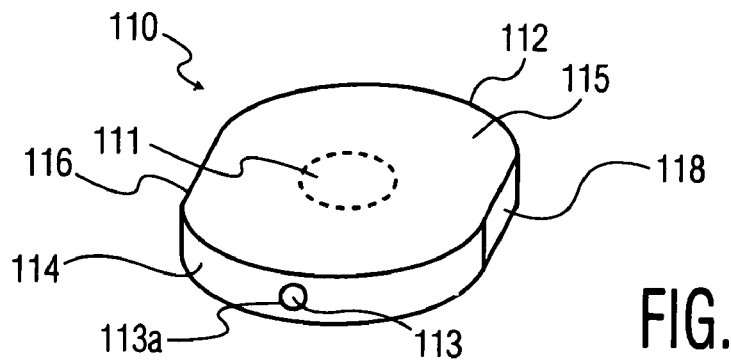

In FIG. 17, another implant embodiment is shown, implant 110. The implant 110 includes opposing arcuate end walls 112 and 114 and planar opposing side walls 116 and 118. End wall 114 is received in a complementary concavity of the mating insertion head. The implant 110 may optionally include a central circular hole 111, shown in phantom in FIG. 17, which may be formed by the medullary canal and further finished as desired. A hole 113 is in the implant 110 end wall 114 with an opening 113*a* in the wall 114 for receiving a stud of an implant head.

Figure 18:
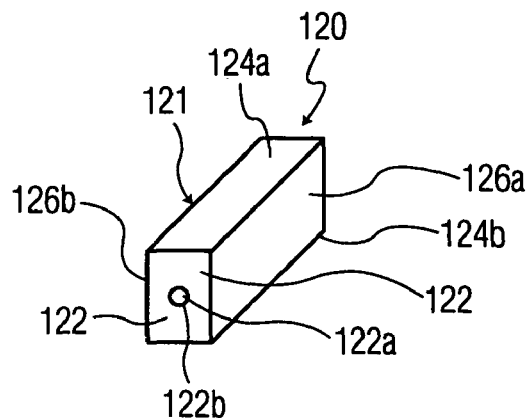

In FIG. 18, another implant 120 is rectangular and includes an elongated body 121 having opposing side walls 124*a* and 124*b*, and 126*a* and 126*b*. An end wall 122 defines an opening 122*b* to a hole 122*a* for mating with a stud of an implant head.

Figure 19:
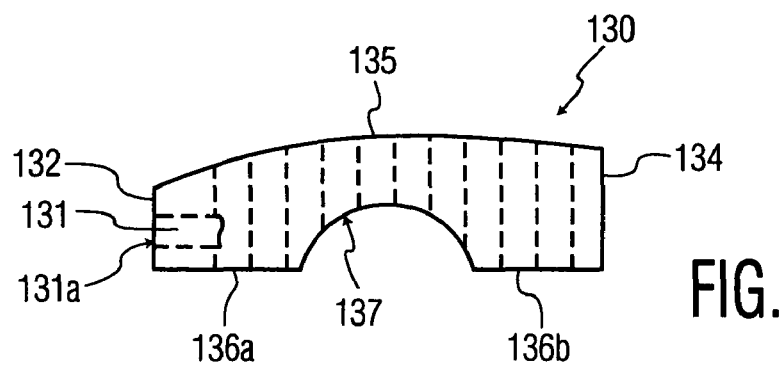

Implant 130, FIG. 19, is of conventional design and is in commercial use, includes opposing end walls 132 and 134, wall 132 being the insertion end and inserted from the posterior approach. End 132 is anterior when inserted. A hole 131 is in the implant 130 anterior end wall 132 with an opening 131*a*. The implant 130 also includes a convex side wall 135 opposite planar wall segments 136*a* and 136*b*. Implant 130 may be formed from a section of a slice taken transversely of a femur bone for example. The planar wall segments 136*a* and 136*b* have a semicircular cavity 137 therebetween which may be formed by the medullary canal of the long bone and further finished. The top and bottom walls which engage the vertebrae have serrations represented by the dashed lines and may be parallel to each other or taper toward each other in a known wedge shape toward the posterior end at wall 134.

Figure 20:
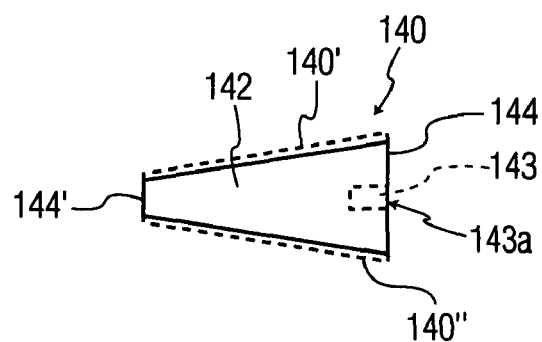

In FIG. 20, implant 140 according to another embodiment is shown. See commonly owned U.S. Pat. No. 6,277,149 which illustrates a similar implant and still other implant configurations which may be used with corresponding complementary instrument heads according to embodiments of the present invention. See also U.S. Pat. No. 6,200,347 which also illustrates similarly shaped implants.

The body 142 of the implant 140 is wedge shaped with tapering respective top and bottom surfaces 140' and 140" and parallel side walls 142 (one being shown). The top and bottom surfaces taper toward each other and toward wall 144'. An axially extending stud receiving hole 143 extending along the longitudinal insertion axis of the implant is formed in anterior end wall 144 having an opening 143*a*. This implant may be inserted using the anterior approach. Hole 143 receives the stud of a mating insertion head. Wall 144' is planar as is wall 144 and side walls 142.

Figure 21:
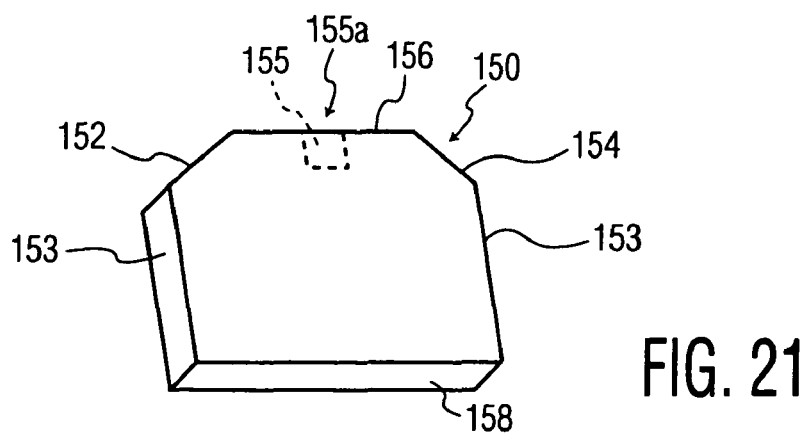

In FIG. 21, another embodiment of an implant is shown, implant 150. A corresponding implant is shown in commonly owned U.S. Pat. No. 6,638,310 and is more fully described therein. The implant 150 includes side walls 153 and end walls 156 and 158. The insertion axis passes through the end walls parallel to the side walls. See the aforementioned '310 patent, FIG. 5B. Walls 152 and 154 are in spaced mirror image to one another and inclined toward each other and terminate at planar insertion end wall 156 therebetween and at respective planar parallel side walls 153. This patent also shows an insertion instrument, FIG. 5B, which would be replaced by the instrument of FIG. 1 for example using an insertion head configured similarly as the head in the patent FIG. 5*b*, but releasably attached to and adjustable as described herein according to one embodiment of the present invention (not shown). The implant would be manipulated during insertion by the instrument of FIG. 1.

The implant 150 end wall 158 is planar and parallel to and in opposing spaced relation to the planar end wall 156. End wall 158 is inserted first into the vertebral disc space. The implant 150 wall 156 has a stud receiving hole 155, shown in phantom, and extending parallel to side walls 153. The hole 155 has an opening 155*a* in the wall 156. The hole 155 receives a stud such as stud 30 of the head 18 of FIG. 2. However, the insertion head for implant 150 would have a head receiving surface such as the surface of wall 41 which is complementary to the implant walls 152, 154 and 156 for receiving these walls as shown in the above noted corresponding patent. The stud such as stud 30, FIG. 2, is dimensioned to closely receive the implant hole 155, FIG. 21, so that the instrument 10, FIG. 1, can temporarily hold the implant during manipulation of the head if needed and during insertion into the disc space.

Figure 22:
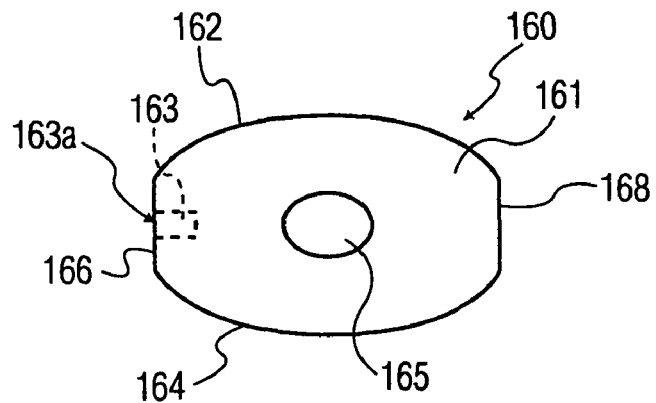

FIG. 22 shows another implant embodiment, implant 160. The implant 160 is somewhat oval shaped includes opposite arcuate side walls 162 and 164, and opposing planar end walls 166 and 168. The planar end wall 166 has a hole 163 with an opening 163*a* in the wall 166. The hole 163 extending partially into the implant 160 in an axial direction, for example, along the anterior-posterior or other axis of the vertebrae. The implant 160 has a substantially central hole 165 which may be formed by the medullary canal.

Figure 23:
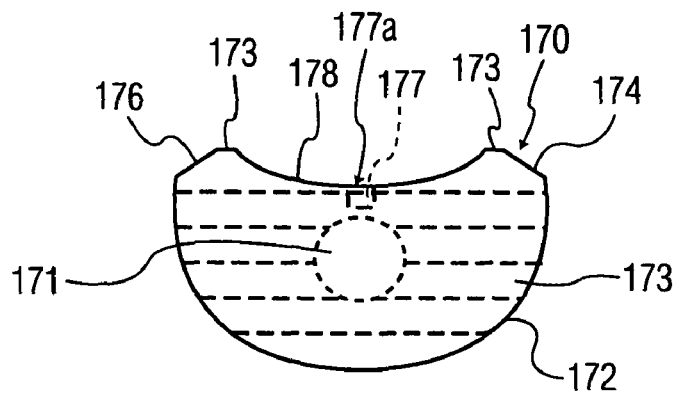

In FIG. 23, another implant embodiment is shown, implant 170. This implant includes an arcuate convex end wall 172 terminating contiguous with angled planar walls 174 and 176 which are inclined toward each other and toward end wall coplanar sections 173. A concave wall 178 terminates at sections 173 and is located therebetween. Wall 178 has a hole 177 with an opening 177*a* which hole extends axially towards the center of the implant 170. The implant 170 may optionally include a central hole 171 shown in phantom in FIG. 23 which may be formed by the medullary canal.

Figure 24:
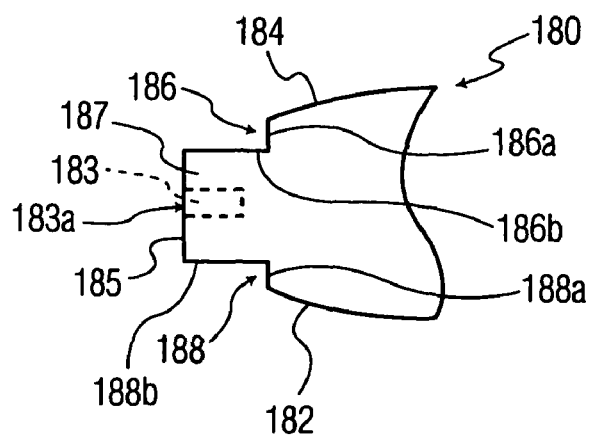

FIG. 24 shows another embodiment of an implant, implant 180. The implant 180 includes opposing arcuate side walls 182 and 184, and stepped portions 186 and 188 in spaced mirror image relation to each other. The stepped portion 186 is formed by walls 186*a* and 186*b* perpendicular to each other, and stepped portion 188 is formed by walls 188*a* and 188*b* perpendicular to each other forming an extension 187. Extension 187 has a hole 183, shown in phantom, in extension end wall 185. The hole has an opening 183*a* in the end wall 185.

The hole 183 receives an insertion head stud. The extension 187 is dimensioned and configured to be complementary to a mating head concavity which receives the extension.

In similar fashion as described above for certain of the implants, all of the implants of FIGS. 16-24 and still numerous others (not shown) which may be commercially available and certain of which are described in corresponding patents (not identified herein), are received in a complementary shaped cavity of an insertion head for insertion by the instrument 10 which releasably receives a mating head in an interchangeable manner according to the configuration of the mating implant being inserted. The holes in the end walls of all of these implants also similarly receive an insertion head stud as explained above.

In operation of the instrument 10, a stud, such as stud 30 of representative head 18, FIG. 2, is inserted in a corresponding implant hole, such as hole 104, implant 100, FIG. 16, hole 113 of implant 110, FIG. 17 and so on, in close, but releasable fitting arrangement to frictionally hold the implant to the corresponding head during insertion. The head attached to the implant is initially loosely held to the instrument shaft portion 12b by the ball joint 40', FIG. 9, so that it may be rotated. This head like all heads for attachment to the instrument 10 have identical ball connection elements as disclosed in the embodiment of FIGS. 2 and 7 or according to the embodiment of FIGS. 14 and 15, by way of example, forming ball joints. Other manipulation head connection elements other than ball joints may be used on the instrument and on the head as disclosed below herein or equivalents thereof according to a given implementation.

As disclosed in FIG. 2, the surgeon can manipulate the head such as head 18 in the directions of arrows a, b and c in any angular orientation. This positions the head and attached implant in the desired orientation relative to the instrument axis 14 for a given insertion direction relative to the body 12 axis 14. Once the relative head orientation is reached, the knob 15 is rotated in a clockwise direction about the axis 14 along the threads 19' (FIG. 4) of the shank 19 to displace the knob relatively on the threads 19' toward the end 20. This action displaces the shank 19 relative position to the left in FIGS. 1-4, direction 14'. This displacement pulls the ball joint 40', FIG. 9, to the left in the figure. The joint 40' is pulled until the head spherical surface corresponding to the surfaces 34a and 34b, FIG. 7, is pulled tightly abutting against the mating complementary concave spherical surface 24', FIG. 8, of the shaft portion 12b. The head is forced sufficiently tight against the surface 24' to lock the head in the preset orientation. The knob and shank thus form a connection structure to temporarily fixedly secure the head to the instrument.

The surgeon then inserts the fixedly held implant in a given orientation relative to the instrument longitudinal axis into the disc space in a conventional manner. The head is then pulled from the inserted implant (held in place in the disc space by the adjacent vertebrae friction load) while the instrument is retracted from the vertebral site. The head can then be used with other implants or removed from the instrument and other heads attached as described hereinbelow.

Figure 25:
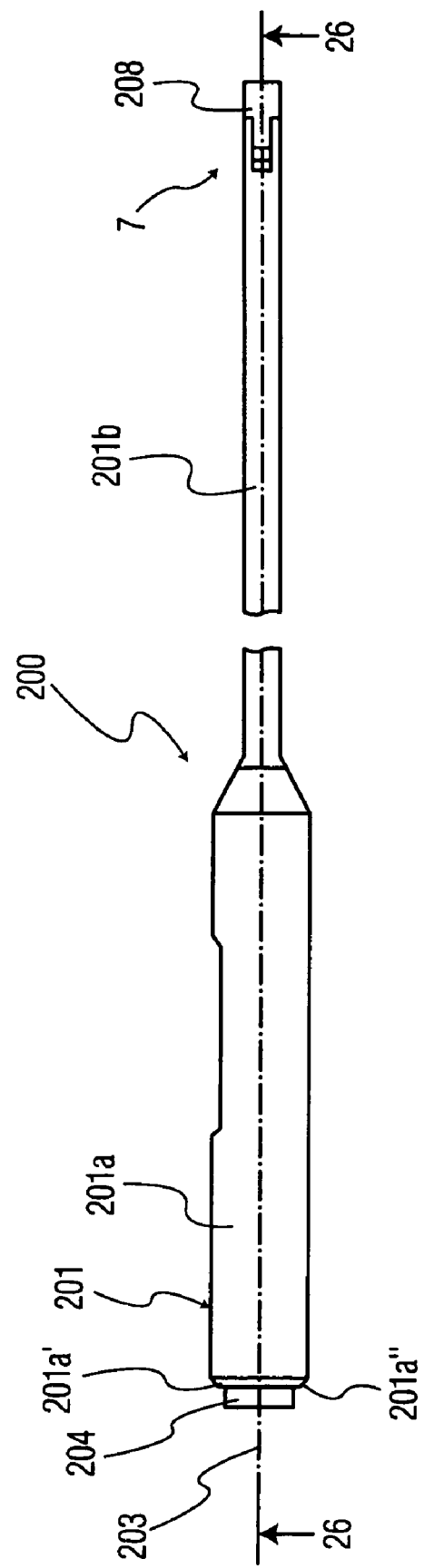
FIGS. 25 and 26 are respective elevation and sectional elevation views, the latter taken along line 26-26 of FIG. 25, of an instrument with an implant insertion head attached according to a further embodiment.
Figure 26:
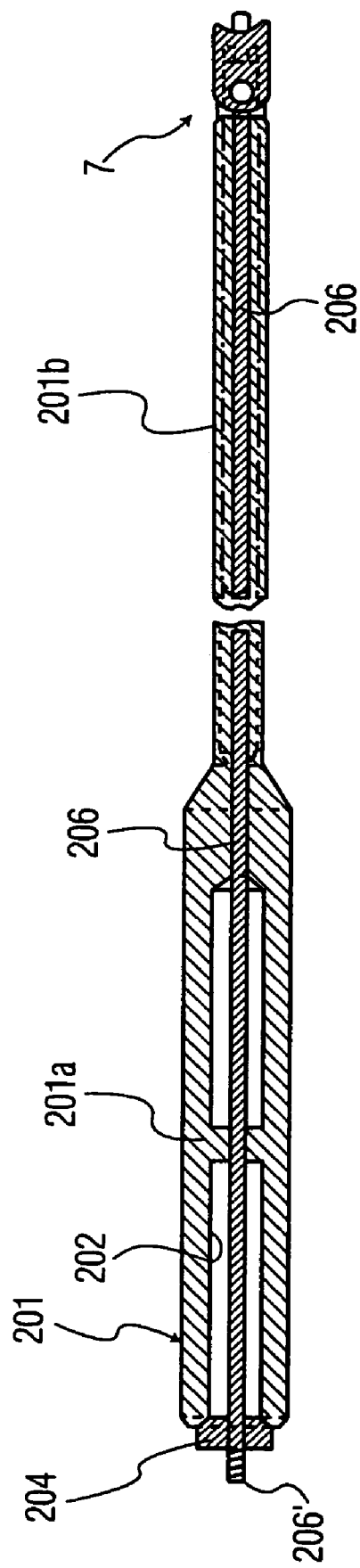
Figure 27:
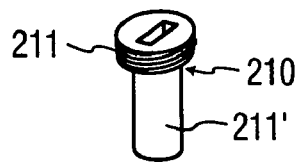
FIG. 27 is an isometric view of a threaded screw for insertion into the articulation joint shown in FIGS. 28-30.

In FIGS. 25 and 26, an implant insertion instrument 200 according to a further embodiment has an elongated cylindrical body 201 including a hollow interior 202. The body 201 includes a handle 201a and a shaft 201b distal to the handle 201a. An articulation joint 7 is attached to the distal end of the shaft 201b. The articulation joint 7 includes an implant manipulation head 208, shown in greater detail in FIGS. 28-30. A knob 204 is attached to a threaded end of a shank 206, FIG. 26, passing through the hollow interior 202 of the body 201 along body 201 longitudinal axis 203. The knob 204 is positioned at a proximal end of the handle 201a. The knob 204 includes internal threads (not shown) which mate with the threaded end 206' of the shank 206 such that the knob rotatably abuts the end wall 201a'' of the handle 201a when the knob is threaded on the threaded portion of the shank in the head locking position. The mating internal threads of the knob 204 and threads of the shank are not shown. The shank 206 mates with the head 208 at the distal end of the instrument as discussed below to form a connection arrangement to temporarily fixedly secure the head to the instrument.

Figure 28:
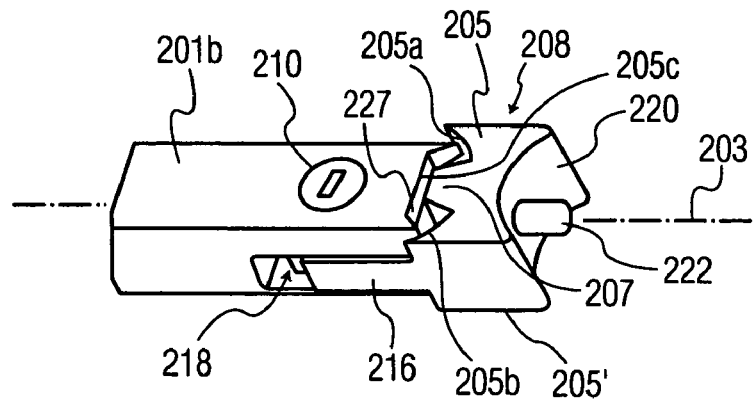
FIGS. 28, 29 and 30 are respective fragmented isometric, plan and sectional plan views of an articulation joint between a head and instrument shaft at region 7 of FIG. 25 and a more detailed sectional plan view of the articulation joint as shown in FIG. 26 taken at the region 7.
Figure 29:
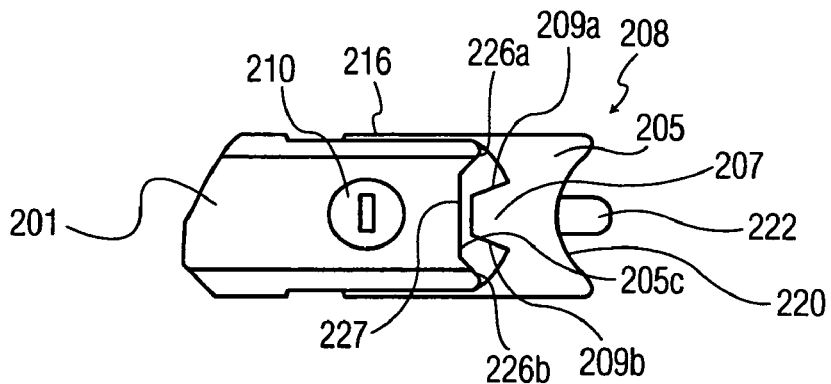

In FIGS. 28 and 29, the head 208 has a rectangular extension tongue portion 216 which fits in a slot 218 at the distal end of the shaft 201b. The head 208 and shaft 201b are rotatably interconnected by a screw 210. The screw 210 has a smooth bearing journal 211' which mates with a journal bore 211'', FIG. 30, in the tongue portion 216. The screw passes through the shaft 201b and the tongue portion 216 of the head 208, securing the head to the shaft. The threads 211 of the screw 210 are secured to mating threads in the shaft 201, and the non-threaded journal 211' provides a pivot for the head 208.

The end of the head 208 opposite the tongue portion 216 engages an implant (not shown). The head surface configuration that mates with an implant is complementary to the given implant to be attached to this head. Other heads having different configurations for mating with complementary implants of different configurations are not shown in these figures.

For the purpose of engaging an exemplary implant, the head 208 includes a concave arcuate surface 220 and a stud 222 extending from surface 220 along the central longitudinal axis 203. The head 208 further includes a top wall 205 which is representative of an opposite bottom side wall 205'. The walls 205 and 205' each include upper and lower juxtaposed arcuate concave portions 205a and 205b, FIGS. 28 and 29, in mirror spaced relation to each other. The walls 205 and 205' each include a corresponding proximally extending trapezoidal upper and lower juxtaposed stop portion 207 therebetween. The portions 207 are parallel and juxtaposed with each other.

The distal end of the shaft 201b has two pairs, an upper pair and a lower pair, of coplanar male projections 226a and 226b which are complementary to and received in the respective female cavities formed by the concave arcuate portions 205a and 205b. There are two pairs of such cavities, upper and lower. The projections and cavities are dimensioned to mate and to permit the head to rotate about the screw 10 a predetermined angular amount.

The shaft distal end also has a pair of upper and lower recesses 205c between the projections 226a and 226b for receiving corresponding proximally extending upper and lower juxtaposed portions 207 of the head 208. Portions 207 each have inclined side walls 209a and 209b, FIG. 29, which abut mating surfaces of the projections 226a and 226b to limit the amount the head can rotate. The projections 226a and 226b are in spaced mirror image relation to each other with a planar wall 227 therebetween forming the base of the recess. The sides of the projections 226a and 226b are inclined for stopping the rotation of the head. The head is stopped by the abutment of corresponding projection 207 side walls 209a and 209b when the head is pivoted about the threaded screw 210. The head is rotated until contact is made between either of the pair of the walls 226a, 226b and the corresponding walls 209a, 209b.

Figure 30:
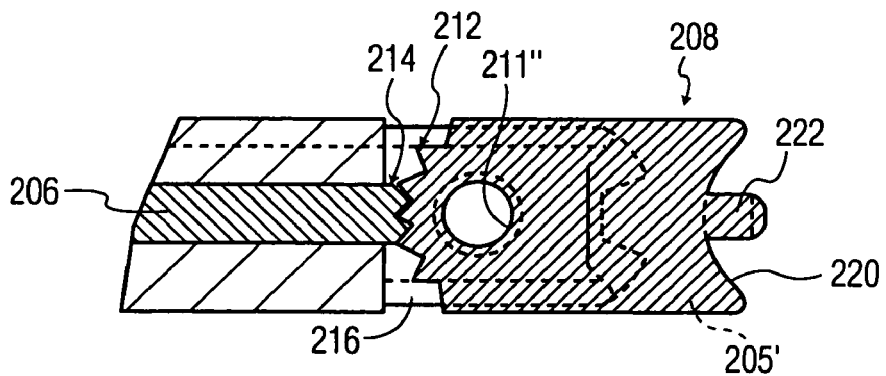

In FIG. 30, the head 208 tongue portion 216 includes an arcuate array of teeth 212 located between the two extending portions 207 and the recesses 205c. The shank 206 includes a toothed end 214 which meshes with the teeth 212 within the central space between the projections 207.

In operation, the head 208 may be angularly positioned by hand to rotate the head about the pivot axis provided by the non-threaded bearing portion 211' of the screw 210. The angular extent of the rotation is determined according to the relative magnitude of the transverse dimension of the space between the projections 226a and 226b to the transverse dimension of the projection 207. By making the projection 207 narrow, the head can rotate a larger angular extent.

The knob 204 is turned to push the shank 206 toward the distal end of the instrument until the teeth 212 and toothed end mesh and lock in place. When the mating teeth 212 and teeth on the toothed shank end 214 are locked into place, FIG. 30, the head can no longer rotate and is fixed in its set angular position. This structure of fixing the head forms a connection arrangement for temporarily fixedly securing the head to the instrument.

Figure 31:
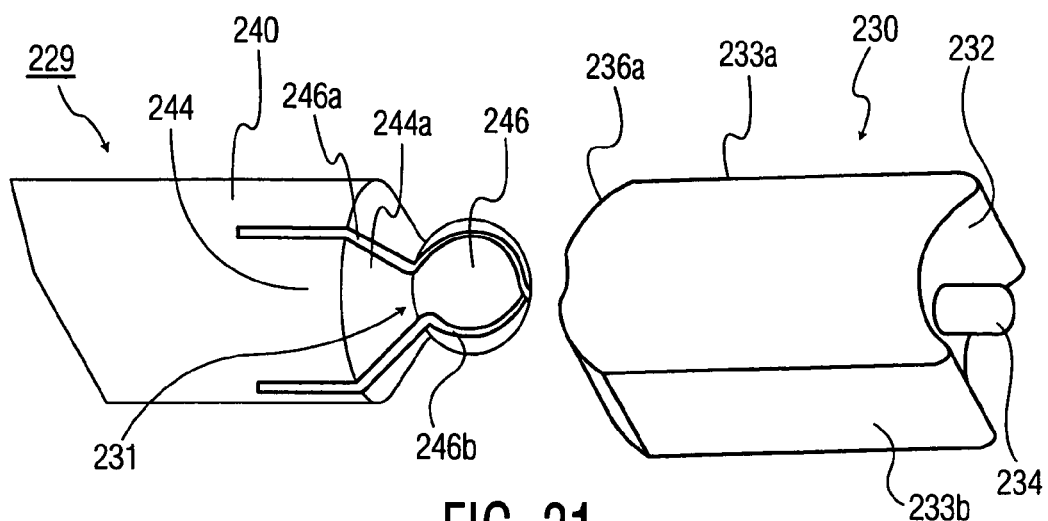
FIG. 31 is an isometric exploded view of an instrument articulation joint and implant insertion head according to a further embodiment.
Figure 32:
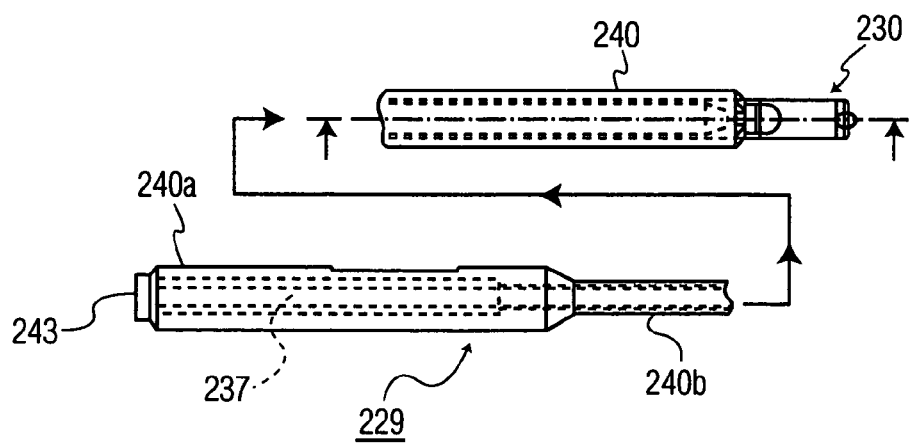
FIG. 32 and FIG. 33 is an exploded side elevation view of the instrument for use with the head of FIG. 31
Figure 33:
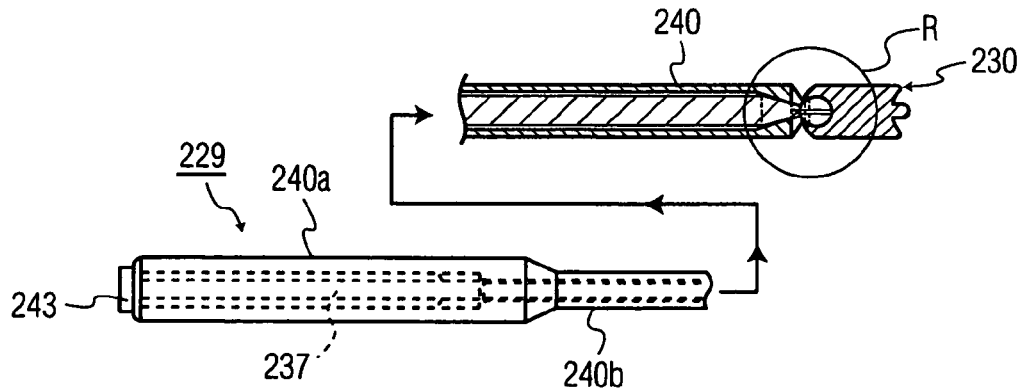
Figure 34:
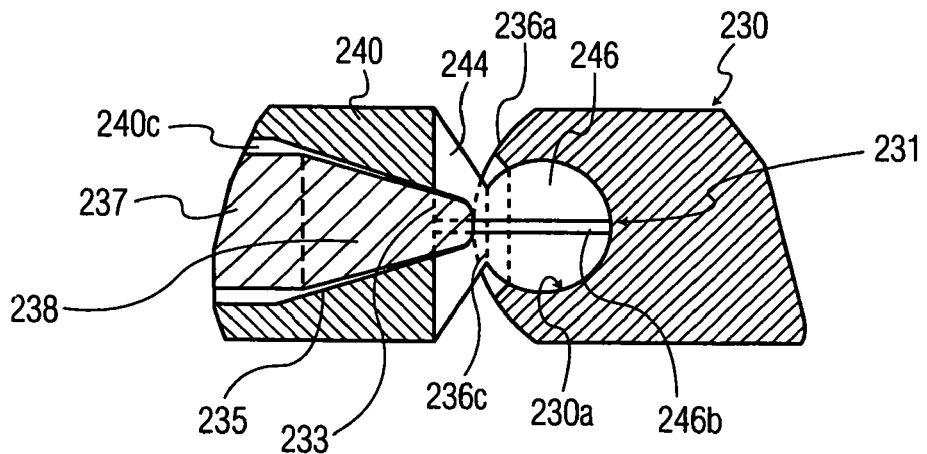
FIG. 34 is a more detailed view of the sectional view portion of the head and shaft articulation joint portion of FIG. 33 taken at region 231.
Figure 35:
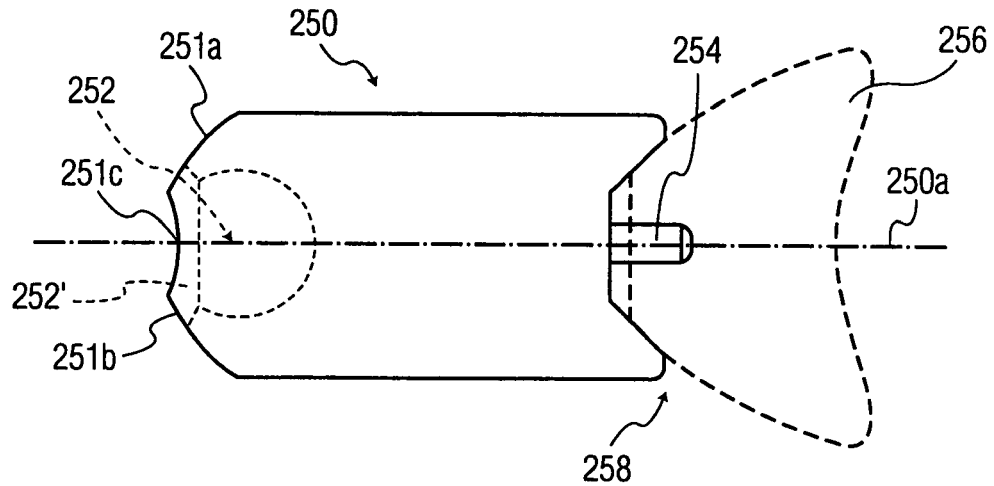
FIG. 35 is a side elevation view of an implant insertion head according to further embodiment with the implant shown in phantom.
Figure 36:
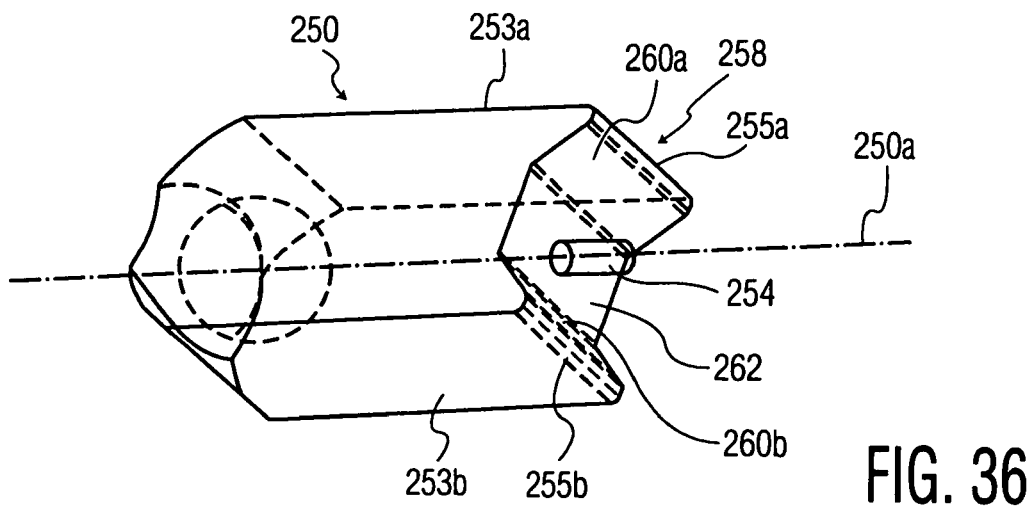
FIGS. 36-39 are respective isometric, rear elevation, front elevation and top plan views of the head of FIG. 35.
Figure 37:
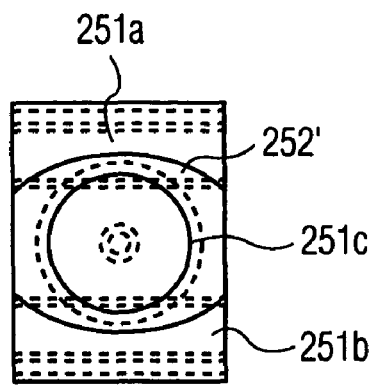
Figure 38:
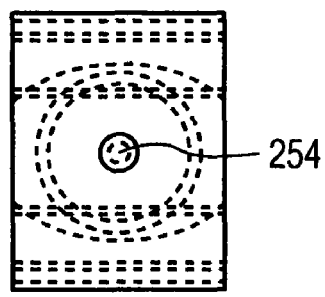
Figure 39:
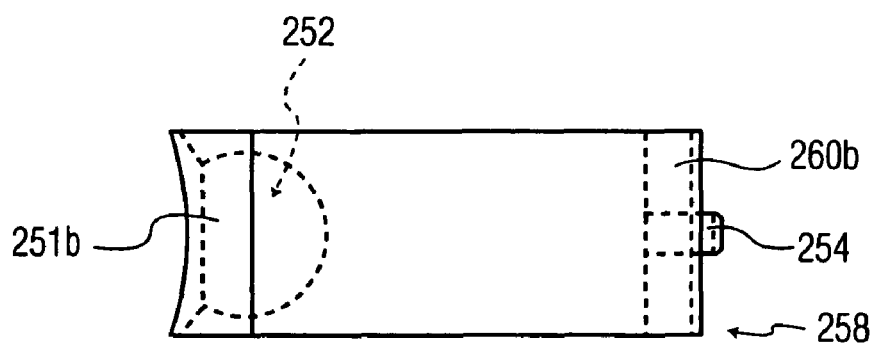
Figure 40:
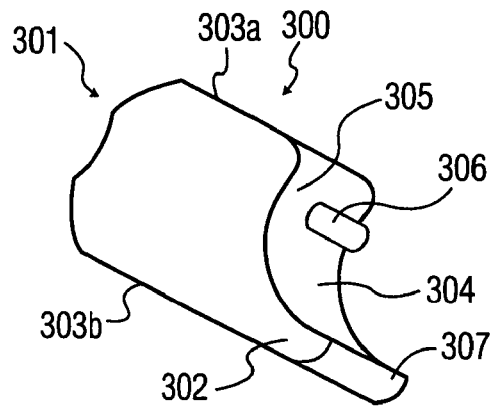
FIGS. 40, 41, 42, 43 and 44 are respective isometric, side elevation, top plan, front elevation and rear elevation views of an implant insertion head according to a further embodiment.
Figure 41:
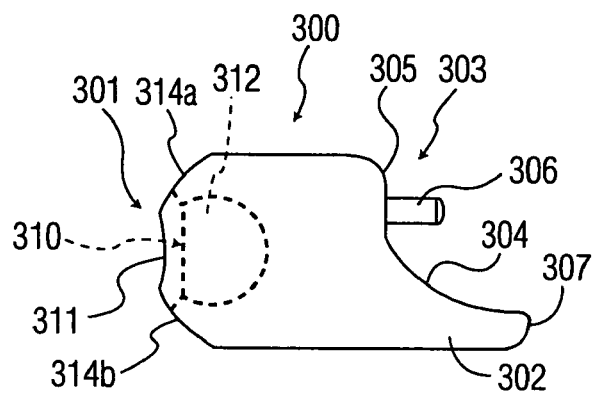
Figure 42:
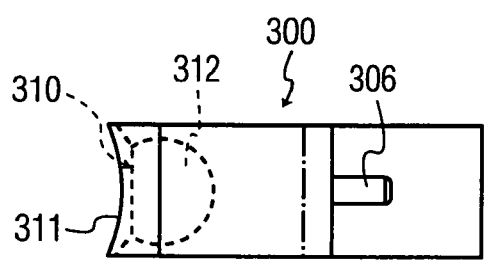
Figure 43:
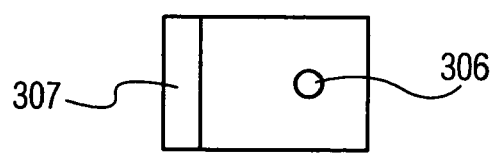

FIGS. 31-34, illustrate an instrument 229 according to a further embodiment of an articulation joint, joint 231, at region R, FIG. 33 and shown in more detail in FIGS. 31 and 34. The joint 231 rotationally and releasably secures implant insertion head 230 to the instrument 229. The instrument 229 has a handle 240a and a shaft 240 that includes a joint 231 male ball 246 extending from the shaft. The implant insertion head 230, FIG. 31, includes a spherical cavity 230a forming the female portion of the joint 231 for mating with and receiving the ball 246, FIG. 34. The shaft 240 distal end at the joint 231 has three slits, slits 246a, 246b and a third slit not visible in the figures. The ball 246 is connected to the end of instrument shaft 240 by resilient relatively thin segments 244 including frusto-conical segments 244a formed by the slits. The ball 246 is formed of equal shaped and dimensioned spherical segments also formed by the three slits 246a, 246b and so on. The three slits also extend partially axially along the shaft 240 outer cylindrical surface to form axial sections of the segments 244. The segments 244 thus include an axial portion of the shaft outer surface, the frusto-concial segments 244a and the ball portions. The segments 244 are equally dimensioned as formed by the slits 246b. The three slits 246a, 246b etc. are equally angularly spaced apart about the longitudinal axis of the instrument shaft 240. The segments 244 are integral one piece with the shaft 240, the segments 244a and the ball 246. The segments 244 and their corresponding section portions of the ball 246 integral with each segment can flex radially toward and away from each other in response to forces thereon. The ball sections have a normal quiescent position as shown with the sections spaced by the slits.

The slits 246a, 246b are dimensioned to permit the ball sections to compress together to fit into the cavity 230a of the head an amount sufficient to pass through the smaller cavity egress opening 236c, FIG. 34. The drawing is not to scale. The ball 246 then expands to its quiescent position once inside the spherical cavity 230a, FIG. 34, forming a ball joint with the ball socket cavity 230a.

An elongated rod 237, FIG. 34, is mounted inside the hollow interior 239 of the shaft 240. The rod 237 has a conical tip 238. The shaft 240b interior 239 has a frusto-conical surface 235 at its distal end. The tip 238 subtends a smaller angle than that of the surface 235. The tip 238 smaller diameter end protrudes through opening 233 at the distal end of the shaft interior 240c, FIG. 34.

The ball 246 and spherical cavity 230a allow the head 230 to be rotated about the center of the ball 246 in any direction to achieve various angles relative to the shaft 240. The rod 237 extends through the interior hollow cavity 240c through the shaft 240 and cylindrical handle 240a of the instrument 229, FIGS. 32 and 33. In FIGS. 32 and 33, a knob 243 is fixed to the proximal end of the rod 237, which is threaded to the interior 239 of the instrument 229 handle and shaft. Rotation of the knob axially displaces the rod 237 relative to the shaft 240. When the shaft displaces to the right in the FIG. 34, the tip 238 displaces further to the right in the figure and engages the frusto-conical surface 235 of the interior 240c. As the rod is forced further to the right in FIG. 34, its conical tip engages the frusto-conical inerior surface of the shaft and forces the shaft segments 144 apart. This forces the ball 246 sections apart and thus eventually frictionally engages the ball 246 against the cavity 230a interior surface locking the head to the ball 246 in a fixed position. the head is released by rotation of the knob in the opposite direction.

The insertion head 230 includes opposing side walls 233a and 233b and proximal convex end wall 236a defining the opening 236c receiving the ball joint 246. The insertion head 230 further includes a distal concave wall 232 having a stud 234 extending perpendicularly therefrom. The stud 234 is adapted to be received in a mating opening in an implant (not shown in these figures, but shown in FIGS. 16-24 by way of example). In the alternative, the rod 237 tip 238 may engage the interior of the junction of the ball 246 with segments 244a rather than the interior of the shaft 240a. That junction and segments have a thinner wall thickness and thus the ball will flex more easily at this junction than at the shaft portions of the segments 244.

FIGS. 35-39 illustrate a further embodiment of an implant insertion head. Insertion head 250 has a spherical ball joint socket cavity 252 at the head proximal end. The head socket cavity receives a ball (not shown) forming a ball joint similar to the joint shown in FIGS. 7-9. The head at the proximal end has two convex wall 251a and 251b in spaced relation to each other and defining an opening 251c (FIG. 37) to the cavity 252 surrounded by a concave surface 252'. The distal end 258 of the insertion head 250 includes two walls 260a and 260b in spaced mirror image relation to each other, extending angularly and preferably defining a planar surface 262 therebetween according to the shape of the mating implant to be received by the head. The planar surface 262 is perpendicular to a longitudinal axis 250a. The walls 260a and 260b are have inclined inner surfaces and are contiguous with parallel side walls 253a and 253b of the insert 250. The side walls 253a, 253b, and the walls 260a, 260b connect at arcuate edges 255a and 255b. A centrally positioned stud 254 extends perpendicularly from planar surface 262 along the longitudinal axis 250a. The stud 254 is closely received in a mating opening in an implant, such as implant 256, shown in phantom in FIG. 35, to releasably frictionally hold the implant in place during surgery. The implant 256 represents a head of any shape and configuration for any desired aspect of the spinal implant insertion procedure. The walls 260a and 250b preferably abut the outer surface of an implant to hold the implant in the correct orientation during surgery.

Figure 44:
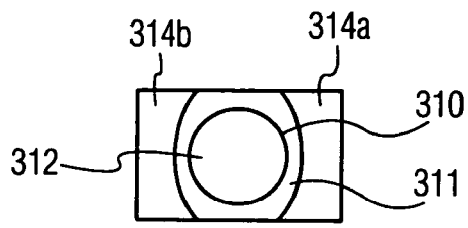

Another embodiment of an insertion head is shown in FIGS. 40-44. In this embodiment head 300 includes opposing side walls 303a and 303b, a proximal end 301 and a distal end 303. A spherical ball joint socket cavity 312 located at the proximal end 301 has an opening 310 surrounded by a concave wall 311, as shown in FIG. 44. Two opposing convex walls 314a and 314b are in mirror image spaced relation and define the annular concave wall 311 therebetween. The spherical socket cavity 312 is receives a ball (not shown) forming the ball joint. A distally extending cantilevered wall 302 extends from side wall 303b of the head 300. The distal end 303 includes a planar end wall portion 305 perpendicular to the representative side wall 303b and contiguous with a concave wall portion 304 joined to the cantilevered portion 302 of the side wall 303b by an arcuate edge 307. An implant receiving stud 306 for closely frictionally engaging a mating implant hole extends perpendicularly from the planar wall portion 305 at the distal end of the head.

Figure 45:
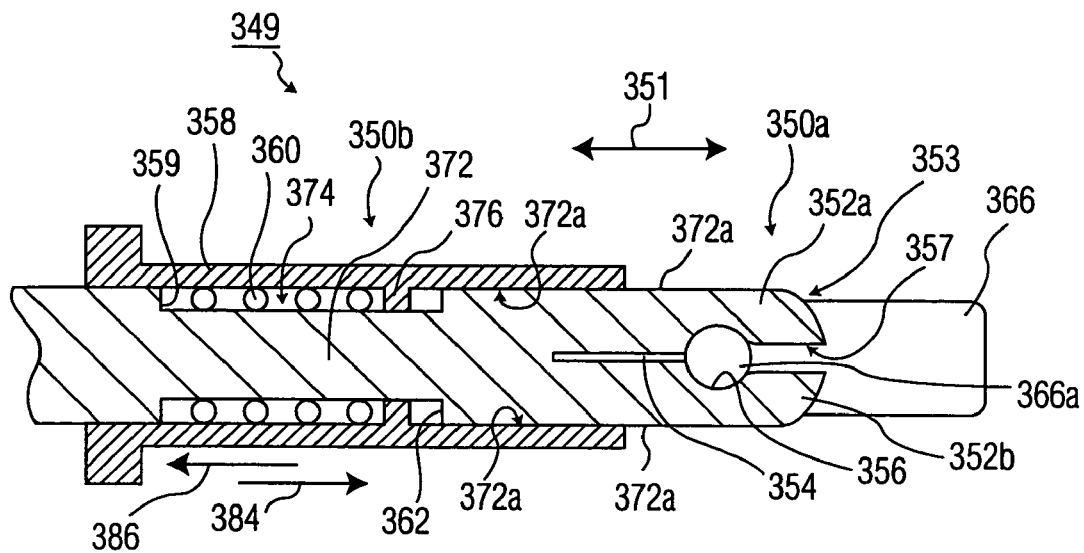
FIG. 45 is a fragmented side elevation sectional view of a interchangeable joint of a shaft and attached implant insertion head or intervertebral disc space processing head according to a further embodiment of the present invention.
Figure 46:
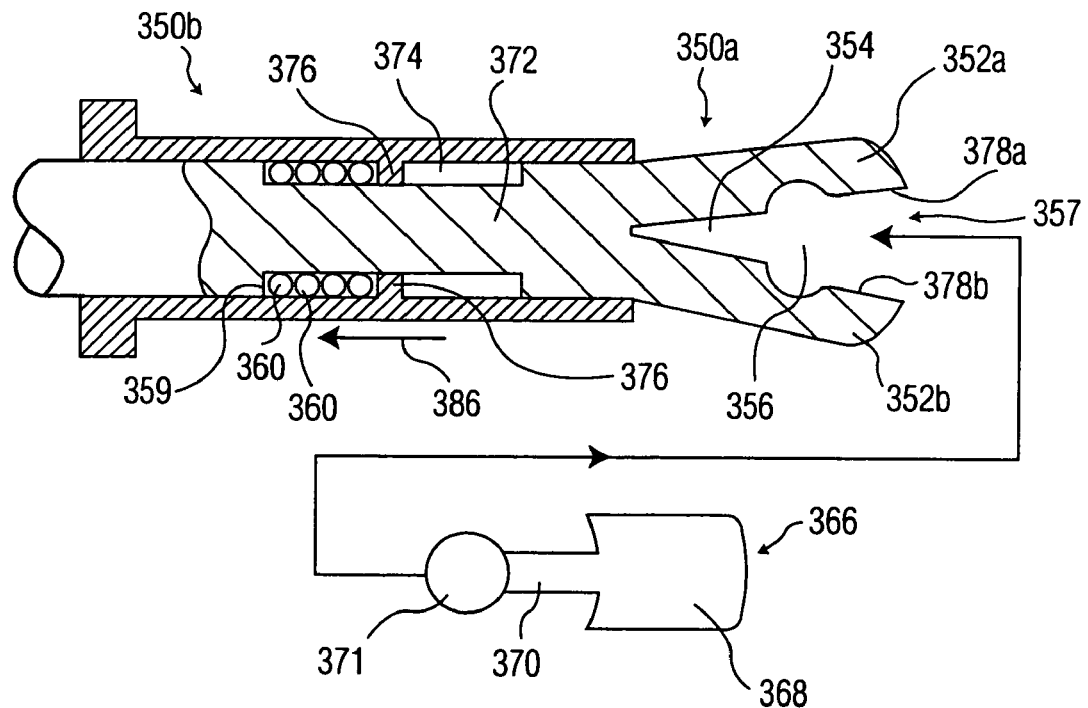
FIG. 46 is an exploded fragmented side elevation sectional view similar to that of FIG. 45 with the head joint element detached from the shaft joint element.

FIGS. 45 and 46 illustrate an embodiment of a connection joint 350a and locking mechanism 350b of a surgical instrument 349 according to the present invention. The mechanism is for locking a disc space processing or implant insertion head 366, which is representative of any tool useful for surgery on a spinal disc space. Such heads are illustrated in detail elsewhere in this disclosure and are interchangeable with the joint and locking mechanism of the instrument 349. The mechanism forms a connection arrangement for temporarily fixedly securing interchangeable tool heads to the instrument.

The surgical instrument 349 includes a shaft 372 and a contiguous handle (not shown). A head and instrument shaft joint 350a is at the distal end of the shaft 372. The joint 350a includes a pair of jaws 352a and 352b in opposing spaced relation from one another. The jaws 352a and 352b define an inner elongated slot 354, a cylindrical socket cavity 356 forming cylindrical joint element and an outer slot 357 therebetween. The slot 354, socket cavity 356 and slot 357 permit the jaws to pivot relative to each other and the shaft 372.

The shaft 372 portion of the locking mechanism 350b has a recessed cylindrical portion 374 which receives an annular coil compression spring 360. A cylindrical sliding member 358 is positioned over the recess and spring and abuts the outer surface 372a of the shaft 372. The sliding member 358 manually slides toward the distal and proximate ends of the shaft 372 in directions 351. The member displacement in the rearward direction 386 is resisted by the compression of the spring 360 between shoulder 359 at the proximal end of the recess 374 and stop element 376 on the sliding member 358. The sliding member 358 is biased by the spring toward the distal end of the joint in direction 384 and is stopped by the stop element 376 abutting shoulder 362 at the distal end of the recess 374. The sliding member 358 is held in place in the head locking position, FIG. 45, by the spring's bias in direction 384.

The jaws 352a and 352b are fabricated to be normally biased in the open position, FIG. 46. The jaws 352a, 352b can open and close as shown in FIGS. 45 and 46 by moving the sliding member 358 proximally in the rearward direction and distally in the forward direction as indicated by arrows 386 and 384, respectively. When the jaws 352a and 352b are forced together by releasing the sliding member 358 to move distally in the forward direction, the cylindrical member 371 of the processing head 366 is held between the jaws 352a, 352b in the cylindrical joint socket cavity 356, as shown in FIG. 45. The force of the jaws 352a and 352b on the cylinder 371 can be released by moving the sliding member 358 in the rearward direction 386 to allow for the head to be inserted and removed from between the jaws. The head 366 is locked in position axially and rotationally in all directions. This is because the slot 357 has a narrower portion (not shown) at each of the sides of the jaws than in the central portion. The wider central portion of the slot 357 thus forms a passage that receives the relatively larger diameter shank 370 of the head as compared to the remainder of the slot 357. The shank 370 of the head 366 in the slot 357 central portion prevents the body 368 of the head 366 from being angularly positioned in and out of the drawing figure in the passage 357. Thus the head 366 once assembled to the jaws is locked in place and can not move in any direction forming a connection arrangement for temporarily fixedly securing the head to the instrument. The head 366 is representative of any interchangeable tool used in processing the disc space such as a chisel, a curette, a distractor or an implant inserter for insertion of an implant into the disc space, for example, or any other spinal surgical tool as may be desired.

In FIGS. 47-50, another embodiment of a surgical instrument according to the invention is illustrated. The instrument 400 includes a joint 400a for attaching a head 424, FIG. 50, to the instrument. The instrument 400 includes an elongated shaft 402 having a cylindrical hole 404 communicating with a slot 406 and two jaw members 403a and 403b, the jaw members forming a female socket portion of the joint 400a.

Figure 47:
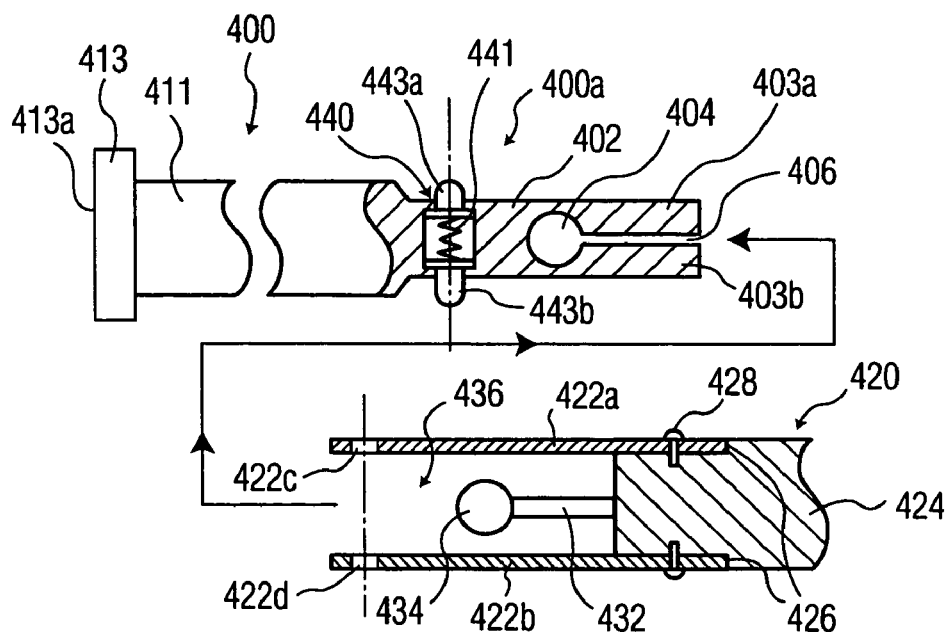
FIGS. 47-50 are 1) a respective fragmented side elevation sectional exploded view of a shaft and head, 2) a side elevation view of an attachment member used in the embodiment of FIG. 47, 3) a fragmented side elevation view of the head joint element and head portion and 4) a fragmented top plan view of the head and shaft of the embodiment of FIG. 47.
Figure 48:
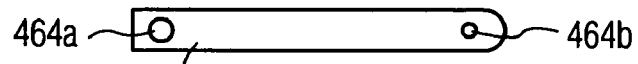
Figure 49:
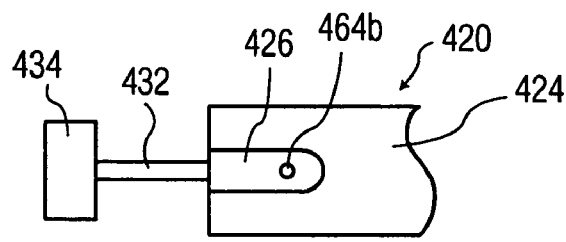
Figure 50:
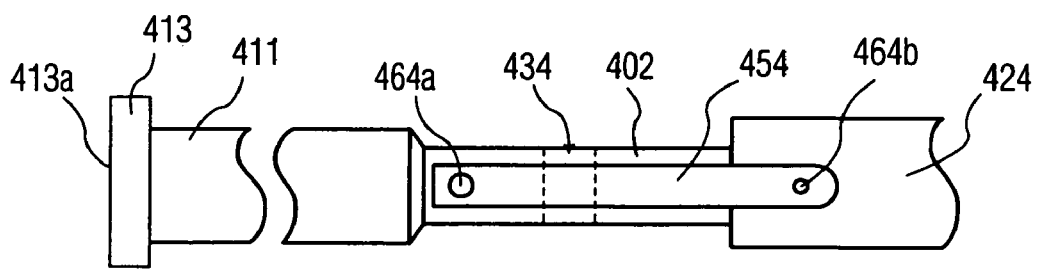

A head assembly 420 is shown in FIG. 47 and includes elongated sheet material upper and lower head attachment members 422a and 422b, and a head 424. The head 424 has two elongated recessed portions 426 on its upper and lower sides which matingly receive the members 422a, 422b. These members are fixed by screws 428 to the head 424 as shown in FIG. 47 or like attachment means.

A cylindrical connector 434 forming a male joint member is attached to the head 424 via an elongated element 432. The cylindrical joint connector 434 fits into the cylindrical socket bore 404 of the elongated shaft 402 forming the joint assembly.

The head is further attached to the shaft by the members 422a and 422b. A pair of oppositely disposed spring loaded plungers 440 are movably captured to the shaft 402. The plungers each have a cylindrical locking elements 443a and 443b in respective bores of the shaft biased outwardly by a central spring 441. The locking elements 443a and 443b and plungers are captured to the shaft bores. The members 422a and 422b include respective holes 464a and 464b for receiving locking elements 443a and 443b of the spring loaded plungers 440.

The cylindrical member 434 is inserted into the cylindrical bore 404 while the locking members 422a and 422b are adjusted over the shaft and depress the plungers. The plungers 443a and 443b then snap into place as they enter the holes 422c and 422d. The elongated elements 454 includes holes 464a and 464b for fixing the elements 454 to the shaft 402 by engagement of the plungers locking elements 443a, 443b with these holes. The members 454 provide additional support for locking the head assembly 420 in place.

The head 424 may be a tamp, a chisel or any other tool with or without requiring an impact surface for applying force for use in any aspect of a spinal implant surgical procedure. The instrument 400 provides a stable head assembly 420 and shaft 402 joint along a singular plane. An end cap 413 is attached to the proximal end of the handle 411 and includes an impact surface 413a such as might be used for insertion of an implant, for use with a chisel, a distractor or other implant insertion processing tool.

Figure 51:
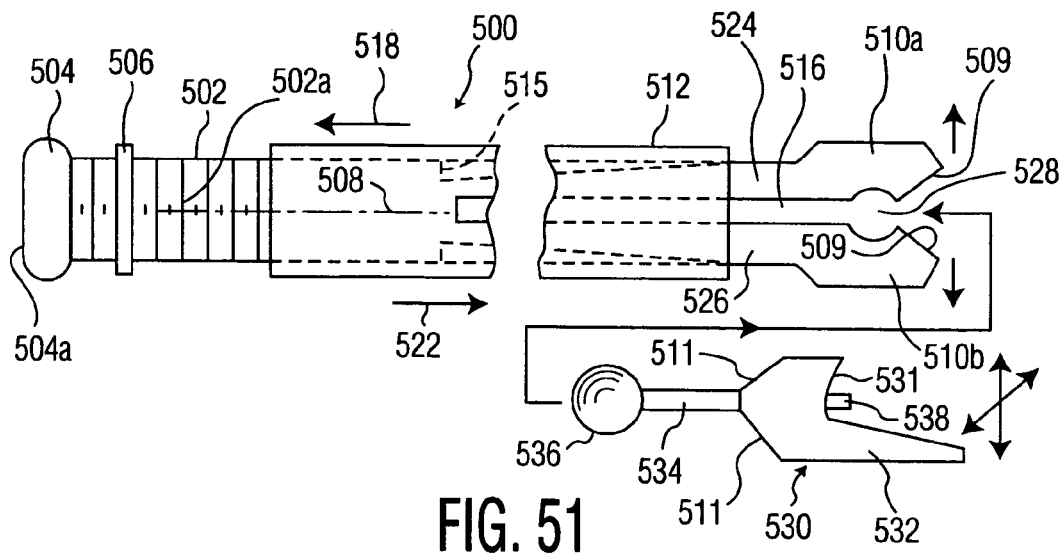
FIG. 51 is an exploded side elevation fragmented view of an instrument and a representative implant insertion head and head-instrument interchangeable joint in a jaw closed state according to a further embodiment.
Figure 52:
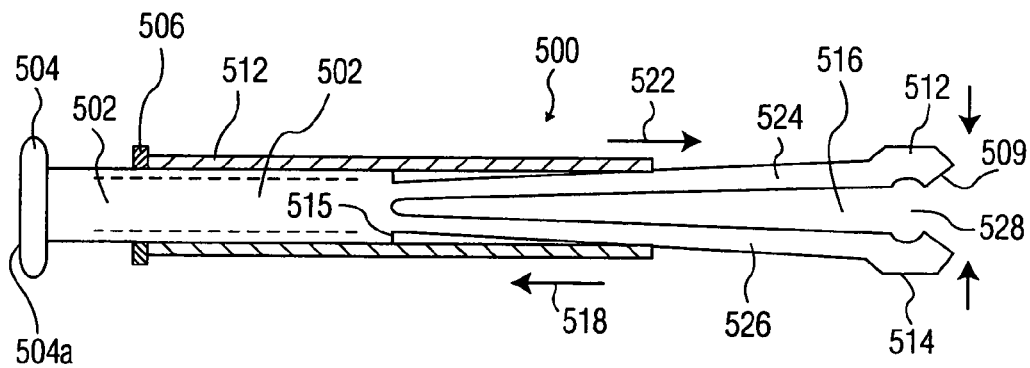
FIG. 52 is a side elevation view partially in section of the instrument of FIG. 51 showing the jaw open state.

Another embodiment of an instrument according to the present invention is shown in FIGS. 51 and 52. In FIGS. 51 and 52, surgical instrument 500 includes a shaft 502 having an enlarged annular gripping member 504 attached to the shaft proximal end. The member 504 has a rear impact surface 504a which receives blows from an insertion hammer. The shaft has longitudinally extending external threads 502a at its proximal end. A nut 506 having internal threads mate with and are attached to the shaft external threads 502a for displacing the nut along the shaft longitudinal axis 508 as the nut is rotated.

The shaft 502 includes resilient jaws 510a and 510b formed therein at the shaft distal end. The jaws 510a and 510b are in opposing spaced relation to each other and are formed by a longitudinal slot 516 and define a spherical opening 528 therebetween in the jaw closed state of FIG. 51. The jaws are relatively thicker than the shaft portion surrounding the slot 516 proximal to the jaws. The jaws 510a and 510b extend distally from respective elongated arms 524, 526 formed by the slot 516. The arms 524, 526 are rectangular in cross section and relatively thin so that they may pivot by bending at their junction at the proximal end of the slot 516. The arms 524, 526 form a step 515 with the shaft portion proximal thereto. The jaws 510a and 510b are reinforced by being relatively thicker than the arms. The jaws have respective distal end surfaces 509 which are inclined in mirror image relation to each other and relative to the longitudinal axis 508, e.g., about 45° to the axis. The jaws are normally inherently biased open as shown in FIG. 52.

A movable sleeve 512 manually slides along the shaft 502 in the forward direction arrow 522 (toward the distal end) and in the rearward direction arrow 518 (toward the proximal end). When the sleeve 512 is moved rearward, the jaws 510a, 510b are resiliently biased in the open position as shown in FIG. 52. When the sleeve 512 is moved forward, in the direction of arrow 522, the jaws 510a, 510b are moved toward one another against their bias to their closed position to secure an exemplary implant insertion head 530 joint member thereto. The jaws may receive other tool heads for different aspects of the implant insertion procedure as described above. The nut 506 is then threaded against the sleeve 512 (see FIG. 52 for this relative position of the nut) to lock it in the closed position of FIG. 51 to securely mount the head 530 to the closed jaws in an immobile position.

The exemplary implant insertion head 530 in this embodiment includes a cantilevered side wall 532 forming a projection that extends distally from end wall 531. An implant receiving stud 538 extends distally from the wall 531. The walls 531 and 532 are configured to receive and mate with an implant complementary surfaces to be inserted into a spinal disc space by the instrument 500. In this case, the wall 531 is arcuate and slightly concave to receive a mating complementary convex surface of the implant and the wall 531 is inclined to receive a complementary inclined side wall of the received implant.

The head 530 has a shank 534 which is elongated and cylindrical, but may be rectangular. A ball 536 which is complementary to but slightly larger than the spherical opening 528 of the closed jaws is connected to the neck 534. The ball 536 is received in the spherical jaw opening 528.

In the alternative, the joint member may be a cylinder and the opening 528 may be cylindrical. This is not as desirable as a spherical arrangement because the head might displace laterally if the joint were cylindrical whereas a ball joint would be laterally immobile. The mating jaw and head inclined surfaces prevent the head from rotating about the ball joint.

In operation, the sleeve 512 is moved rearward, direction 518 so that the jaw members open in response to the bias of the arms 524, 526. The jaws open an amount sufficient for the ball 536 to be inserted into the enlarged opening 528. When the sleeve 512 is moved forward in direction 522, the jaw members close as shown in FIG. 51 clamping the ball 536 to the jaws. The nut 506 is then rotated to abut the sleeve proximal end and is further rotated to tightly clamp the ball 536 to the opening 528. This action locks the insertion head 530 in a desired position. The nut may include a bore (not shown) for receiving a rod to assist in locking the nut in its final position by providing additional torque to the nut.

The head 530 has inclined surfaces 511 which abut the inclined surfaces 509 of the jaws, FIG. 51, to securely lock the head in the desired orientation relative to the axis 14, and in this case with the circular cylindrical stud 538 longitudinal axis parallel to the instrument longitudinal axis 508. The head is thus fixed immobile in this position both by the clamping action of the jaws and by the mating abutting inclined head and jaw surfaces. The inclined mating surfaces of the head and of the jaws prevents the head from rotating relative to the jaws and instrument when locked in place. The spherical ball joint prevents the ball from displacing out of the joint during use.

The sleeve 512 may also be somewhat frictionally attached to the shaft 502 outer peripheral cylindrical surface which may have a larger diameter than the threads 502a in a manner not shown. Thus the sleeve can retain its position on the shaft unless manually moved. However, the nut 506 is threaded along the threaded portion 502a of the shaft 502 to lockingly abut the sleeve 512 in the jaw closed state and also to further displace the sleeve to its final locking position to firmly clamp the jaws to the processing head.

In another embodiment, the sleeve 512 may have internal threads that mate with threads along the length of the shaft 502. Rotation of the sleeve about the shaft translates the sleeve along the shaft to the jaw open and closed states.

Figure 53:
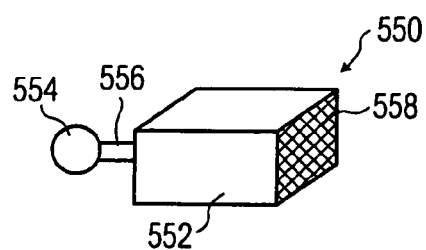
FIGS. 53-57 are isometric views of respective implant impact heads (FIGS. 53 and 54), a chisel head (FIG. 55), a distractor head (FIG. 56) and a rasp head (FIG. 57) which may be attached to the shafts of the instruments of FIGS. 51 and 52 in exemplary embodiments.
Figure 54:
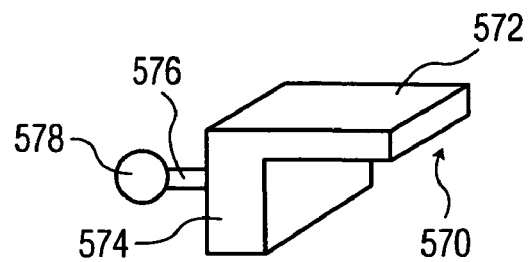
Figure 55:
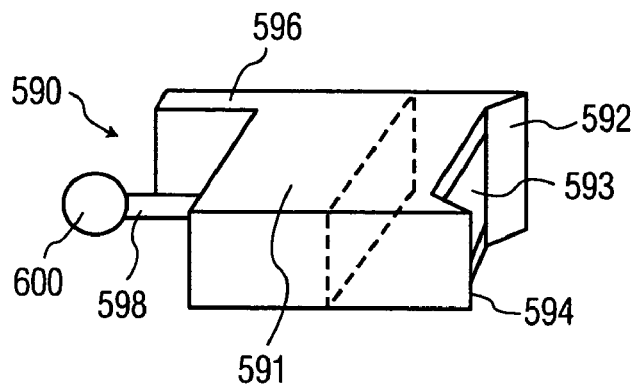
Figure 56:
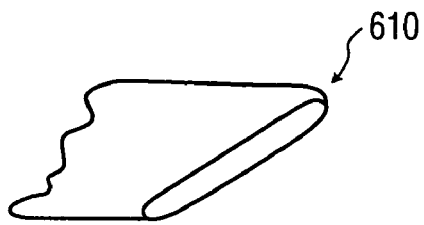
Figure 57:
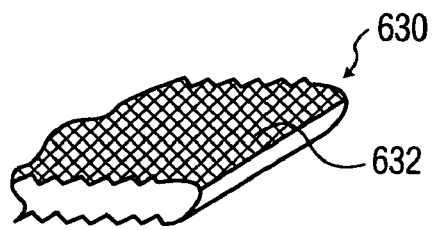

Embodiments of an implant impact head, a chisel head, a distractor head and a rasp head are shown in FIGS. 53-57. FIGS. 53-55 show heads having a ball of the ball joint for use, for example, with the instrument 500 of FIGS. 51 and 52. The heads shown in FIGS. 56 and 57 are fragmented views of heads which also may include a ball and shank as in the heads shown in FIGS. 53-55.

In FIG. 53, an implant impact head 550 has a generally rectangular body 552 and a ball 554 for a ball joint connected to the body 552 by a shank 556. The distal end of the head includes a roughened surface 558 such as knurling, or pits and valleys which provide enhanced gripping friction with the contacted implant during spinal implantation surgery. The head 550 like all heads and tools disclosed herein are preferably stainless surgical steel.

In FIG. 54, implant head 570 includes a body which is generally "L" shaped and includes cantilevered distally extending leg 572 which extends from leg 574 at right angles to one another. The implant head 570 is also connected to a ball 578 via a shank 576.

In FIG. 55, chisel head 590 has a rectangular body 591 and which includes a cantilevered wall 596 extending rearwardly in the proximal direction from the body at the body proximal end. A shank 598 extends from a proximal wall of the body 591 perpendicularly adjacent to the cantilevered wall 596. A ball 600 is attached to the distal end of the shank for mating, for example, with a spherical opening such as opening 528, FIG. 52. Two chisel edges 592 and 594 in opposing parallel spaced relation to one another extend from the body 591 at the distal body end opposite the ball joint 600 at opposite sides of the body 591. The body 591 has a cavity 593 adjacent to and rearward of the edges 592 and 594. Once the chisel head 590 is locked in position in an instrument, the chisel head 590 can be used for cutting and scraping vertebrae and disc material during spinal implant surgery.

FIG. 56 illustrates a distractor head 610. A rasp head 630 is shown in FIG. 57 having a roughened rasp surface 632. Surface 632 may comprise an array of pyramidal teeth as known in this art. The distractor head 610 and the rasp head 630 have a shank and ball attached similar to the heads 550, 570 and 590 and are connected to a instrument such as instrument 500, FIGS. 51 and 52 similarly.

Figure 58:
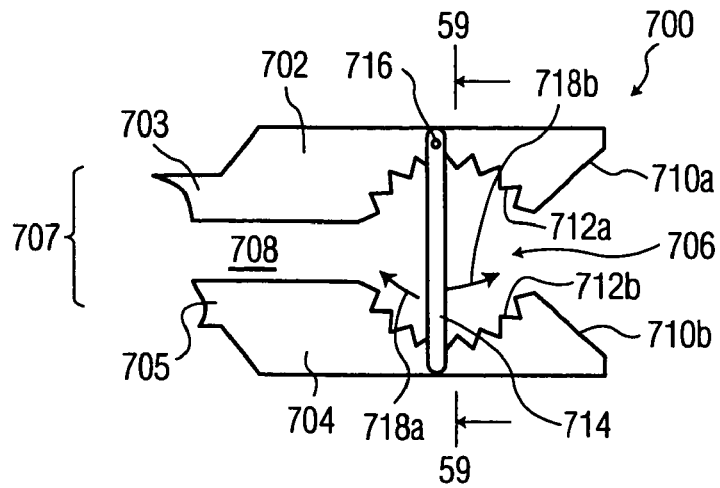
FIGS. 58 and 59 are respective fragmented side elevation and front elevation views taken along lines 59-59 of FIG. 58 of a female articulation joint element of an instrument shaft according to a further embodiment of the present invention.

A female articulation joint element 700 is shown in FIG. 58. The element 700 includes an upper arm 703 and a lower arm 705 formed from a shaft 707 by slot 708. See the instrument of FIGS. 51 and 52 for example. The upper arm 703 terminates at upper jaw 702 and the lower arm terminates at lower jaw 704 in opposing spaced relation to each other similar to the instrument shown in FIGS. 51 and 52. The arms are normally biased apart in the jaw open state as described in connection with instrument of FIG. 51.

Figure 61:
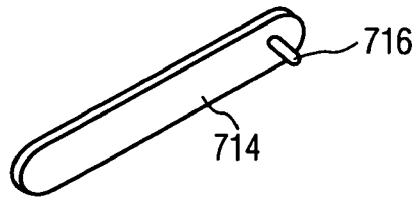
FIG. 61 is an isometric view of a joint element retaining member used in the embodiment of FIGS. 58 and 59.
Figure 62:
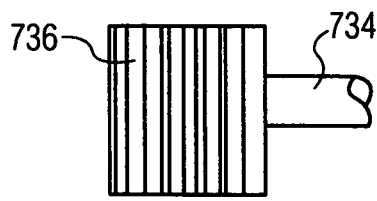

The jaws 702 and 704 have slot 708 therebetween and form a cylindrical transverse opening 706 at the slot 708. The distal ends of the jaws 702, 704 each have an inclined surface 710a, and 710b. Each of the jaw members 702, 704 includes a respective toothed arcuate surface having linear elongated teeth 712a and 712b. Each surface is formed by an array of parallel like transverse saw teeth 712a and 712b normal to the side walls of the jaws and to the plane of the drawing figures. A retaining arm 714, FIGS. 58 and 61, is pivotally attached at one arm end to opposite sides of the upper jaw member 702 using a peg 716 as a pivot member. The arm 714 pivots about the pivot axis as indicated by arrows 718a and 718b and overlies the opening 706 somewhat medially of the opening. The other end of the arm 714 opposite the peg 716 can be releasably secured, in the desired position shown in FIG. 58, to the lower jaw member 704 using conventional means, such as a detent bumps (not shown) on the side of the jaws.

Figure 59:
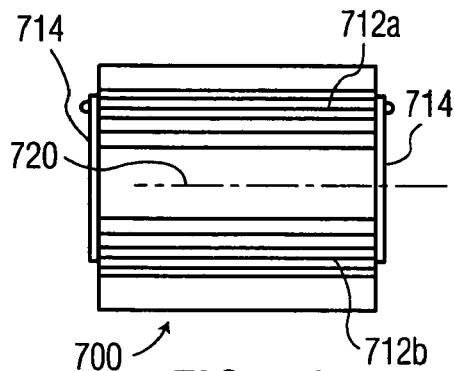
Figure 60:
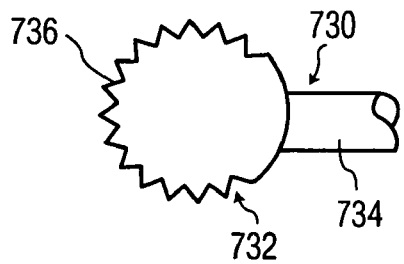
FIGS. 60, 62 and 63 are respective side elevation view, top plan view and isometric view of an instrument implant insertion or processing head male articulation joint element that mates with the joint element of FIG. 58.
Figure 63:
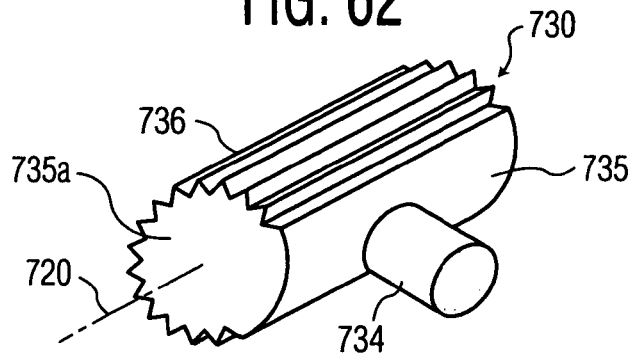

A cylindrical male joint structure 730, FIGS. 60 and 63, has planar opposite side walls 735a and an elongated body 735. The cylindrical joint structure 730 may be attached to an implant head or tamp (not shown) or other instrument spinal surgery processing head as, for example, the embodiments shown in FIGS. 53-55. The cylindrical male joint structure 730 has a surface 732 which includes teeth 736 that mate with the teeth 712a and 712b of the joint element 700. The mating arrangement of teeth 736, 712a, 712b provides stepped or incremental articulation of the cylindrical joint structure 730 between the jaw members 702, 704 about axis 720, FIGS. 59 and 63. Once the joint structure 730 is articulated into a desired angular position relative to slot 708 and the instrument shaft 707, FIG. 58, the structure can be fixed into that angular position by using the arms 714 to hold the head or tamp or the like transversely to a shaft 734 attached to the joint structure 730.

The jaws 702 and 704 are locked in place by the remainder of the instrument structures such as disclosed in the instrument of FIGS. 51 and 52 using a sleeve to close the jaws and lock them closed with a nut. The natural bias of the jaw arms opens the jaws when the sleeve is retracted rearwardly as shown above in FIG. 52. The arms 714, FIG. 58, insure that the male joint structure 730 does not slide transversely out of the jaws 702 and 704 along the axis 720, FIG. 59. A shank 734 connects the male structure to any of a plurality of different spinal processing tool heads as described elsewhere herein.

Figure 64:
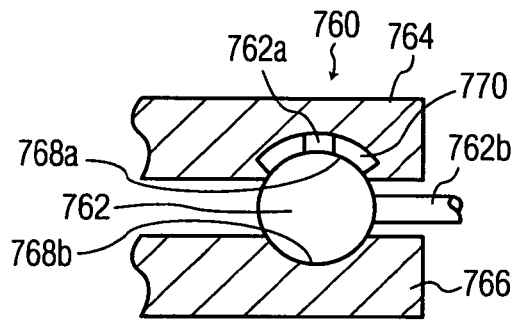
FIG. 64 is a fragmented side elevation sectional view of an articulation joint between a head and a shaft end according to a further embodiment.
Figure 65:
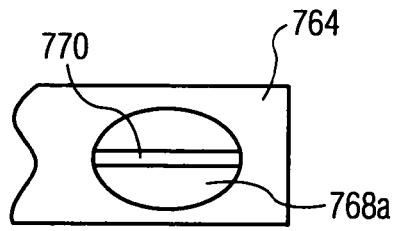
FIG. 65 is a bottom plan view of the upper shaft member of the joint of FIG. 64.
Figure 66:
FIG. 66 is a top plan view of the lower shaft member of the joint of FIG. 64.

In FIGS. 64-66, a distal end of an articulation ball joint 760 of an instrument according to the present invention is shown. The ball joint 760 has a female portion formed in upper and lower jaws 764 and 766, respectively. The jaws may be part of an instrument as shown in FIGS. 51 and 52, for example. The joint 760 includes a male ball 762 seated in complementary spherical portion mating female recesses 768a and 768b in the upper and lower jaws 764, 766, respectively. These spherical portion recesses in essence together cooperate to form a spherical cavity for receiving the ball 762 of the joint 760. The ball 762 includes a protruding member 762a for mating with and received in a slot 770 in the recess 768a of the upper jaw 702, FIGS. 64 and 65. The arcuate recess 768b in the lower jaw 766 is also shown in FIG. 66. The interaction between the slot 770, which defines a plane, and the mating received protruding member 762a limits the range of motion of the ball joint 762 to the plane of the slot.

A shank 762b is connected to the ball 762 and in turn is connected to a processing head (not shown in these figures). The head can be angularly articulated in the plane of the slot 770 to an angular range extent as allowed by the protruding member 762a moving in the slot 770. The desired angle the head can be set and then locked in place by the jaws 764, 766. In an alternative embodiment (not shown), the recess 768a may include a further intersecting slot or slots defining a still different plane or planes for receiving the protruding member 762a and further limit the motion of the ball joint 762 along such different arcuate paths defined by these further slots.

Figure 67:
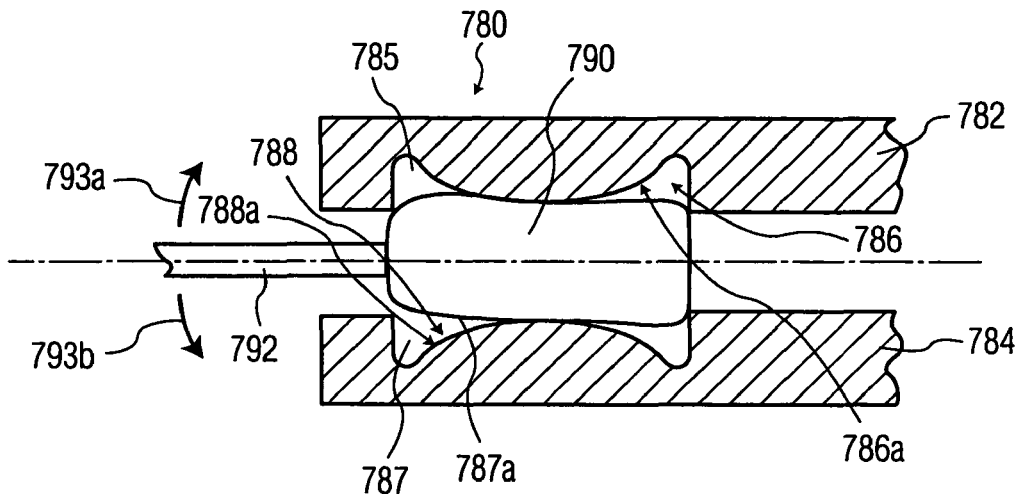
FIG. 67 is a fragmented side elevation partially in section view of an articulation joint between a head and a shaft according to a further embodiment.

A distal end of a surgical instrument 780 is depicted in FIG. 67 including upper and lower jaws 782, 784. These jaws may also be manipulated between open and closed locked positions as described in the other embodiments herein, such as in FIG. 51. The jaws 782, 784 include recesses 786 and 788 having complementary convex surfaces 786a and 788a, respectively. The recesses 786 and 788 are in mirror image spaced relation to one another. An articulation male joint member 790 is an elongated cylinder or rectangular shape with rounded end corner edges attached to shank 792. Shank 792 is attached to a processing head (not shown in these figures). The male member 790 is located between the convex surfaces of the recesses 786, 788 of the respective upper and lower jaw members 782, 784.

The joint member 790 can be manipulated angularly as shown by arrows 793a and 793b in a limited fashion, but when formed of a cylindrical shape is free to rotate about a longitudinal axis. When rectangular, the male member 790 can only rotate in a plane. If cylindrical, it can also rotate about the axis of the cylinder as well. The joint member's 790 motion is defined by the interaction of the convex surfaces 786a and 788a with the cylindrical or rectangular shaped joint member 790. Once positioned, the joint member 790 can be locked into place using the jaws 782 and 784 to clamp the member 790 in a similar fashion as shown in previous embodiments.

Figure 68:
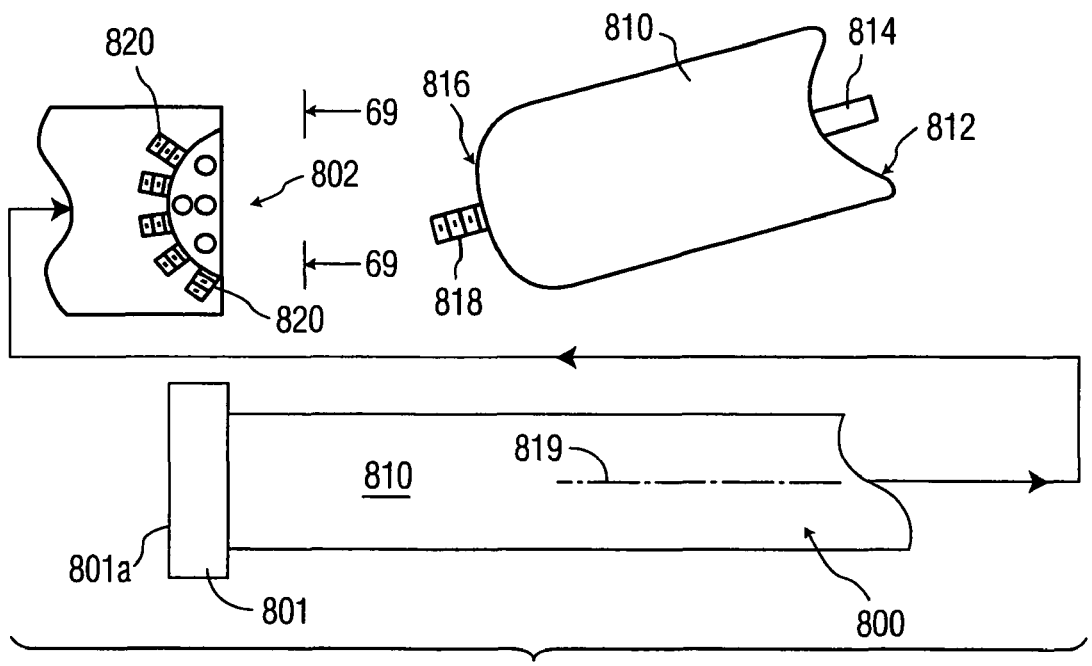
FIG. 68 is a fragmented exploded side elevation view of an instrument shaft and head joint according to a further embodiment of the present invention.

In FIG. 68, an instrument 800 according to a further embodiment of the present invention includes a female joint element 802. The instrument 800 includes an impact surface 801a on an impact portion 801 at a proximal end of the instrument handle 810. A representative processing head, e.g., an implant insertion head 810, has a concave surface 812 having a stud 814 projecting perpendicularly therefrom for mating with a complementary shaped implant (not shown). The end of the head opposite the stud 814 has a convex spherical surface 816 including a threaded stud 818 extending perpendicularly therefrom and in opposing relation to and on a parallel axis as the stud 814.

Figure 69:
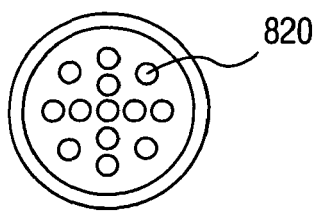
FIG. 69 is an end elevation view of the instrument shaft end showing the joint element of the shaft.

The female joint 802 of the instrument 800 includes a plurality of like threaded holes 820, FIGS. 68 and 69, in spaced relation in a spherical surface complementary to and for receiving the surface 816. The hoes 820 receive the threaded stud 818. The plurality of threaded holes 820 are in different angular orientations relative to each other. The plurality of threaded holes 820 provide articulation of the head 810 by the stem 818 being threaded to a selected threaded hole 820 to fix the head 810 at a desired angle relative to the instrument shaft axis 819.

The surgical instruments according to the embodiments of the present invention provides a means for interchanging and in some cases articulating insertion heads such that various spinal surgical processing devices may be used as described above. For example, curettes, rasps, chisels, or rongeurs may be used with an instrument according to the present invention by using similar joint devices as disclosed above in the various figures for the various tools illustrated herein. Various heads also as discussed below may be used with the different surgical instruments according to the present invention.

Figure 70:
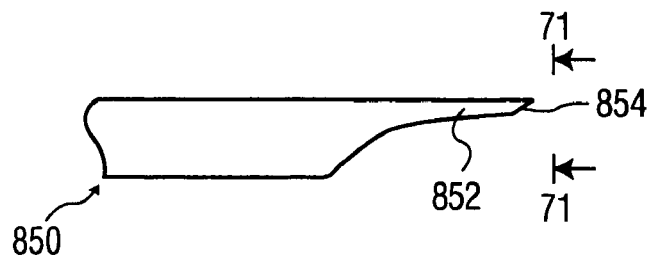
FIGS. 70-80 are respective side and end elevation views of a chisel head (FIGS. 70 and 71) taken along lines 71-71 of FIG. 70, end elevation and isometric views of a chisel portion of a head (FIGS. 72 and 73), and various views of different curettes (FIGS. 74-80)
Figure 71:
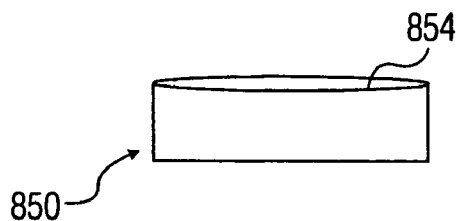
Figure 72:
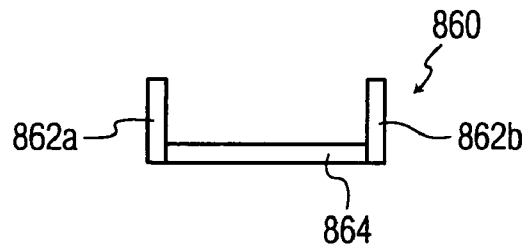
Figure 73:
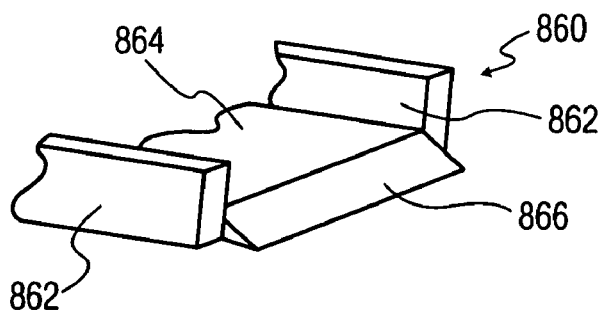

A chisel head embodiment is shown in FIGS. 70 and 71. The chisel head 850 has a cantilevered portion 852 terminating in a cutting edge 854. Another chisel head embodiment 860 is shown in FIGS. 72 and 73. Chisel head 860 has a "U" shaped configuration having two side walls 862a and 862b and a bottom wall 864 terminating in a cutting edge 866, as shown in FIG. 73. The chisel heads 850 and 860 can be attached to a shaft of an instrument in a similar manner as described above, for example, using a ball or cylindrical joint at the distal end of the instrument.

Figure 74:
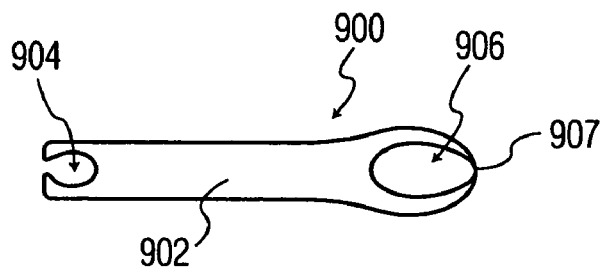
Figure 75:
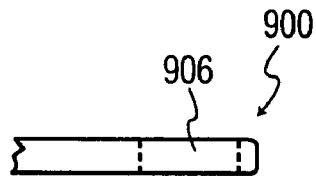

Several embodiments of curettes are shown in FIGS. 74-80 which may be used with various ones of the surgical instruments as described above herein according to the joint associated with the curette and instrument for which it is intended to be used. The curettes may have connection devices (not shown) for connection to different joints as may be desired. One embodiment of a curette 900 is shown in FIGS. 74 and 75. The curette 900 includes an elongated body 902 having a joint arcuate socket 904 at one end, to mate with a male joint element of an instrument shaft, and an oval processing cavity 906 adjacent to an arcuate cutting edge 907 at an opposite end. The socket is shown schematically and in practice includes details of one of the various joint arrangements as discussed above herein.

Figure 76:
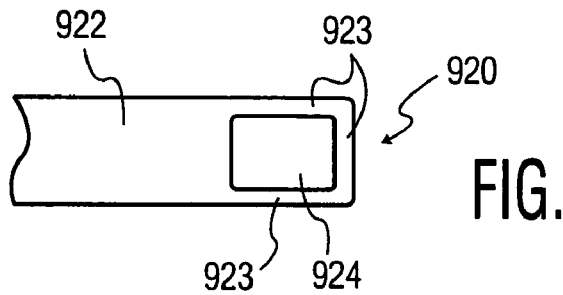
Figure 77:
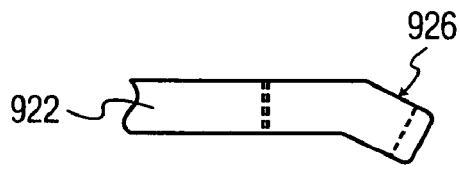

Another curette for use with an instrument according to the present invention is shown in FIGS. 76 and 77 without a joint member being shown, it being understood such a joint would be configured as discussed elsewhere herein. The curette 920 includes an elongated body 922 having a rectangular hollow core 924 adjacent to conventional cutting edges 923 at the instrument distal end. The body 922 includes an angled segment 926 as shown in FIG. 77.

Figure 78:
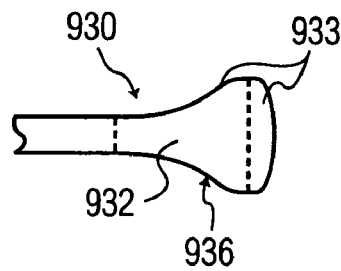

Another embodiment of a curette 930 is shown in FIG. 78. The curette is similar to the curette shown in FIG. 76 having a hollow core 932 shown by the dashed lines depicted in FIG. 78 and adjacent to tissue cutting edges 933. However, the curette 930 shown in FIG. 78 does not have an angled segment, and includes a tapered body 936.

Figure 79:
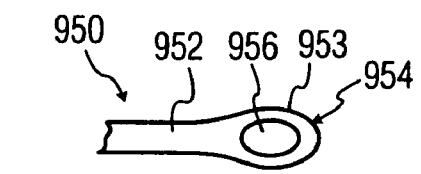
Figure 80:
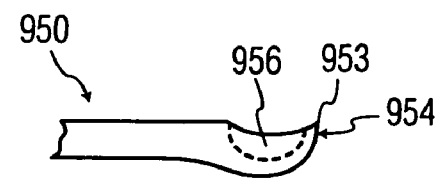

Another curette 950 is shown in FIGS. 79 and 80. The curette 950 includes an elongated body 952 and an arcuate distal end 954 defining a hollow core 956 adjacent to a cutting edge 953.

Figure 81:
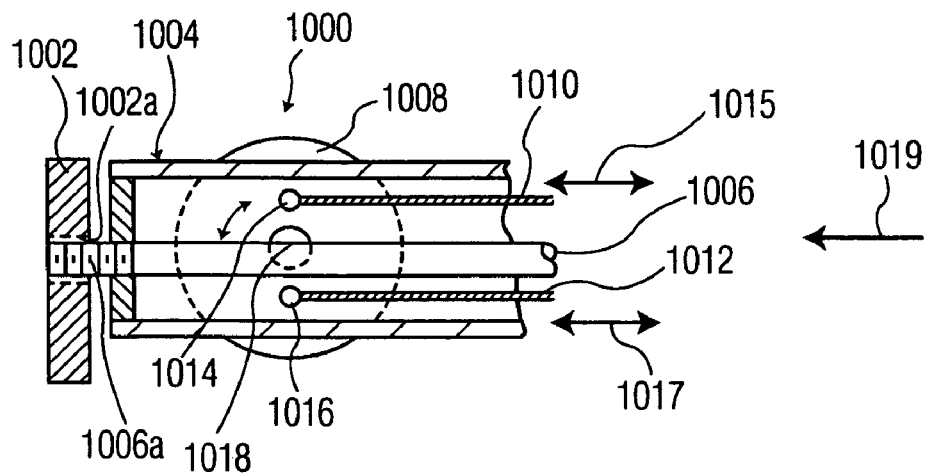
FIG. 81 is a fragmented sectional elevation view of a handle end of an instrument according to an embodiment of the present invention and FIG. 82 is a fragmented sectional elevation view of the head-shaft articulation joint of the instrument of FIG. 81.
Figure 85:
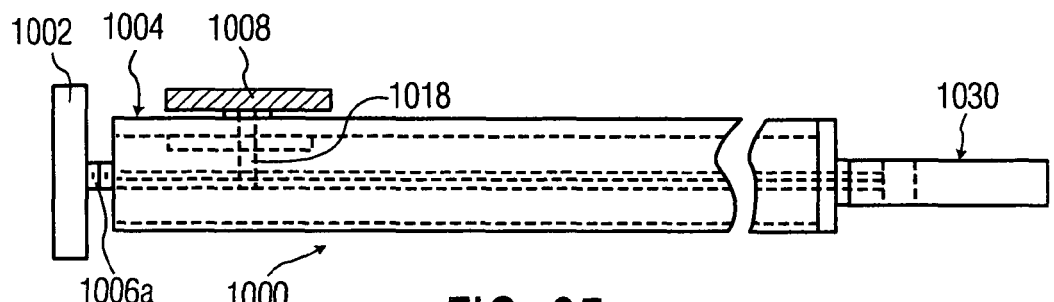
FIG. 85 is a fragmented top plan view of the instrument of FIGS. 81 and 82.

Another embodiment of a surgical instrument 1000 according to the present invention is shown in FIGS. 81-85. The handle end (proximal end) of the surgical instrument 1000 is shown in FIG. 81. The instrument includes an end rotatable knob 1002, a body 1004 forming a handle, a substantially elongated longitudinal shaft 1006 and a rotatable side knob 1008 mounted to the side of the body 1004. Elongated filaments 1010 and 1012 are connected to the side knob 1008 at spaced connection points 1014 and 1016, respectively. The points 1014 and 1016 are spaced equally from and on diametrically opposite sides of the knob shaft 1018. The side knob 1008 rotates on shaft 1018 mounted to the body 1004, as shown in FIG. 85. Rotation of the knob 1008 displaces the filaments 1014 and 1016 in opposite ones of directions 1015, 1017. For Example, filament 1014 displaces to the right in the figure and the filament 1016 displaces to the left when the knob 1008 is rotated clockwise in the figure. The filaments move in the opposite directions when the knob is rotated counter clockwise in the figure.

The end knob 1002 includes a threaded internal bore 1002a which mates with a threaded portion 1006a of the shaft 1006. When the end knob 1002 is turned, it displaces the shaft 1006 in one of directions 1015 (and the same one of directions 1017). For example, when the knob is threaded to the right in the figure it abuts the body 1004 and further rotation of the knob pulls the shaft 1006 to the left in the figure and vice versa when the knob is rotated in the opposite direction about shaft 1006.

Figure 82:
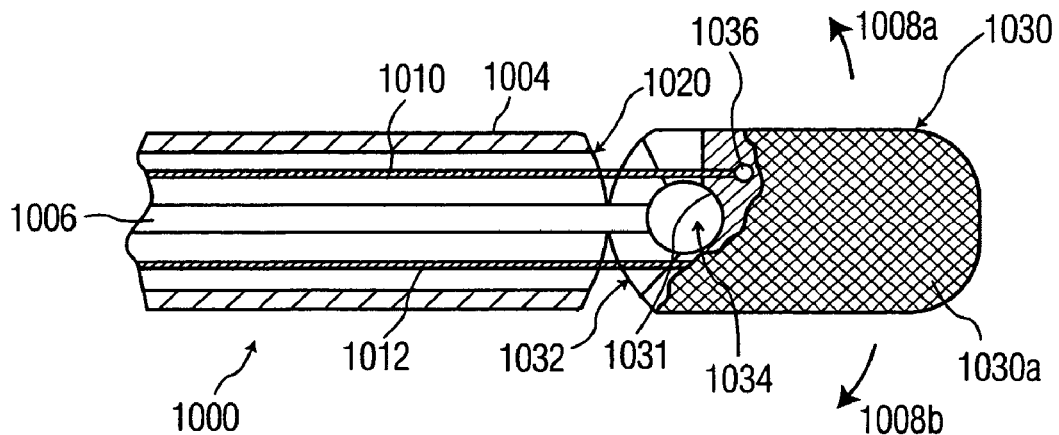

In FIG. 82, the filament 1010 is connected to a rasp flat head 1030, by way of example, at point 1036 and the filament 1012 is also attached to a point (not shown) on the head 1030 spaced from point 1036 in the same relative position on the head to the axis of rotation of the head, discussed below, as points 1014 and 1016 on the knob 1008 are to the axis of rotation of the knob 1008. The attachment of point 1036 is representative of both attachment points.

Figure 83:
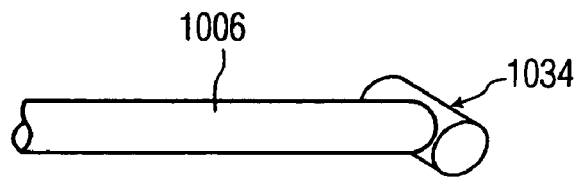
FIG. 83 is an isometric view of the male articulation joint element of FIG. 82.
Figure 84:
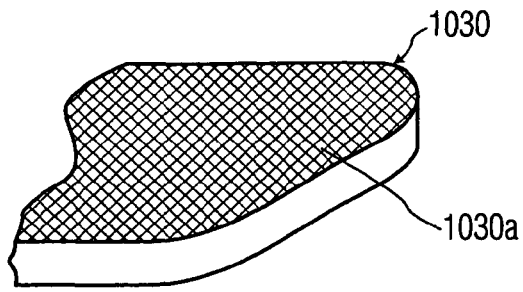
FIG. 84 is an isometric view of the rasp head of the embodiment of FIG. 82.

The head 1030 has a semi-cylindrical cavity 1031 for receiving a cylindrical joint member 1034 attached to the shaft 1006 distal end, FIGS. 82 and 83. The head 1030 has a convex surface 1032 at a proximal end thereof abutting a complimentary convex surface 1020 of the body 1004 at the body 1004 distal end. Preferably the surfaces 1020 and 1032 subtend the same arc and have the same radii of curvature. The convex surfaces 1020 and 1032 engage when the head 1030 is pulled toward the body 1004 by rotation of the knob 1002 in a direction which pulls the shaft to the left in the figure, direction 1019, FIG. 81.

When the side knob 1008 is rotated, the filaments are taught and pull on the head 1030 in direction 1019 at either of the connection points represented by connection point 1036 in accordance with the direction of rotation of the knob 1008. When the side knob 1008 is rotated counterclockwise, the filament 1010 pulls the head so that the head rotates in a first direction arrow 1008a via connection point 1036. The head rotates about an axis formed by the joint member 1034 engaged with the cylindrical head cavity.

When the side knob 1008 is rotated clockwise, the filament 1012 pulls the head in a second opposite direction arrow 1008b via the other connection point (not shown). The head 1030 slides along its convex surface 1032 against the convex surface 1020 of the body 1004 as the head 1030 rotates. The head 1030 rotates about an axis of rotation formed by the cylindrical cavity portion 1031 rotating about the journal formed by the joint member 1034.

After the head 1030 is rotated in a desired position, the end knob 1002 is turned to thread the threaded portion 1006a of the shaft 1006 further into the internal bore 1002a of the end knob 1002 direction 1019, locking the head 1030 in place. The rasp head 1030 is shown in more detail in FIGS. 82 and 84 which depict the rasp tooth surface 1030a. While a rasp head is illustrated in this embodiment, such a head is by way of example, as any other spinal processing tool head such as an implant insertion head, a distractor, an impact head, a curette and so on may also be used interchangeable with the instrument 1000.

A surgical rongeur instrument 1100 according to the present invention is shown in FIGS. 86-89. The rongeur 1100 includes a hollow core cylindrical body 1102, FIGS. 86, 88 and 89, and a shank 1110 located in the core of the cylindrical body 1102. A knob 1104 having internal threads (not shown) is threaded to a mating threaded end 1110a of the shank 1110. An abutment collar portion 1104a of the knob contacts the proximal end surface 1102b of the instrument 1100 body 1102.

Figure 86:
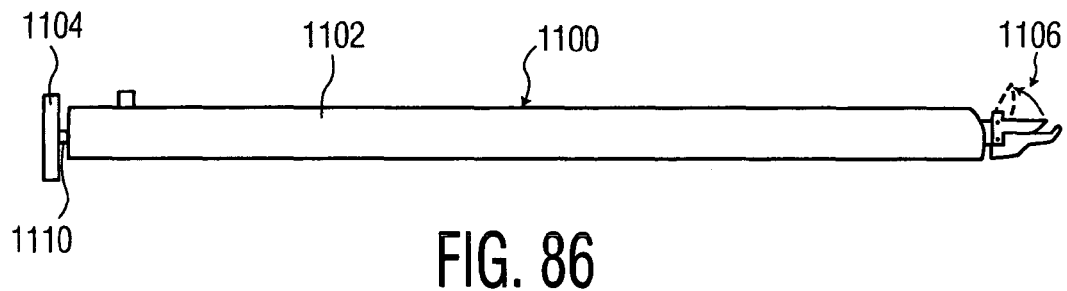
FIG. 86 is a side elevation view of a surgical rongeur instrument according to an embodiment of the present invention.
Figure 87:
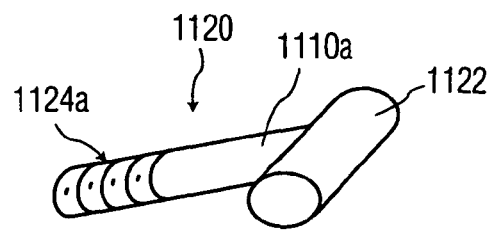
FIG. 87 is an isometric view of the male joint element of the instrument of FIG. 86.
Figure 88:
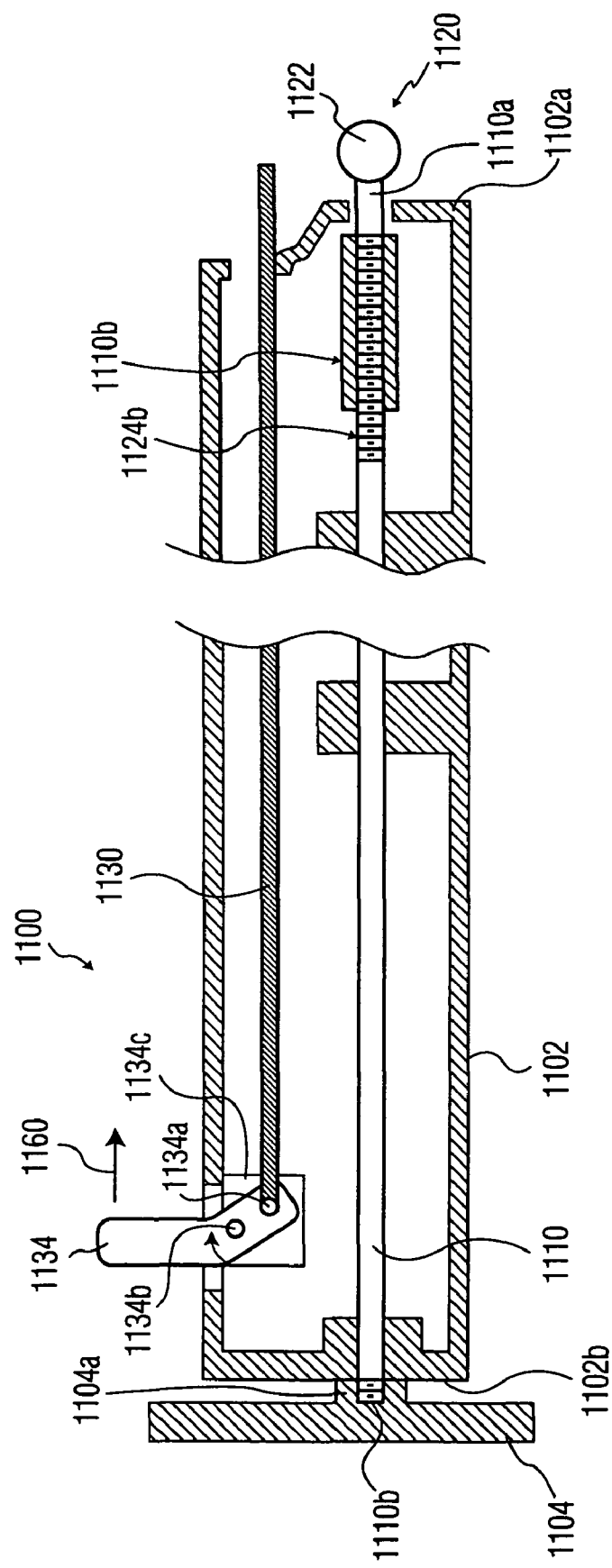
FIG. 88 is a more detailed fragmented sectional elevation view of the instrument of FIG. 86 without the head attached.
Figure 89:
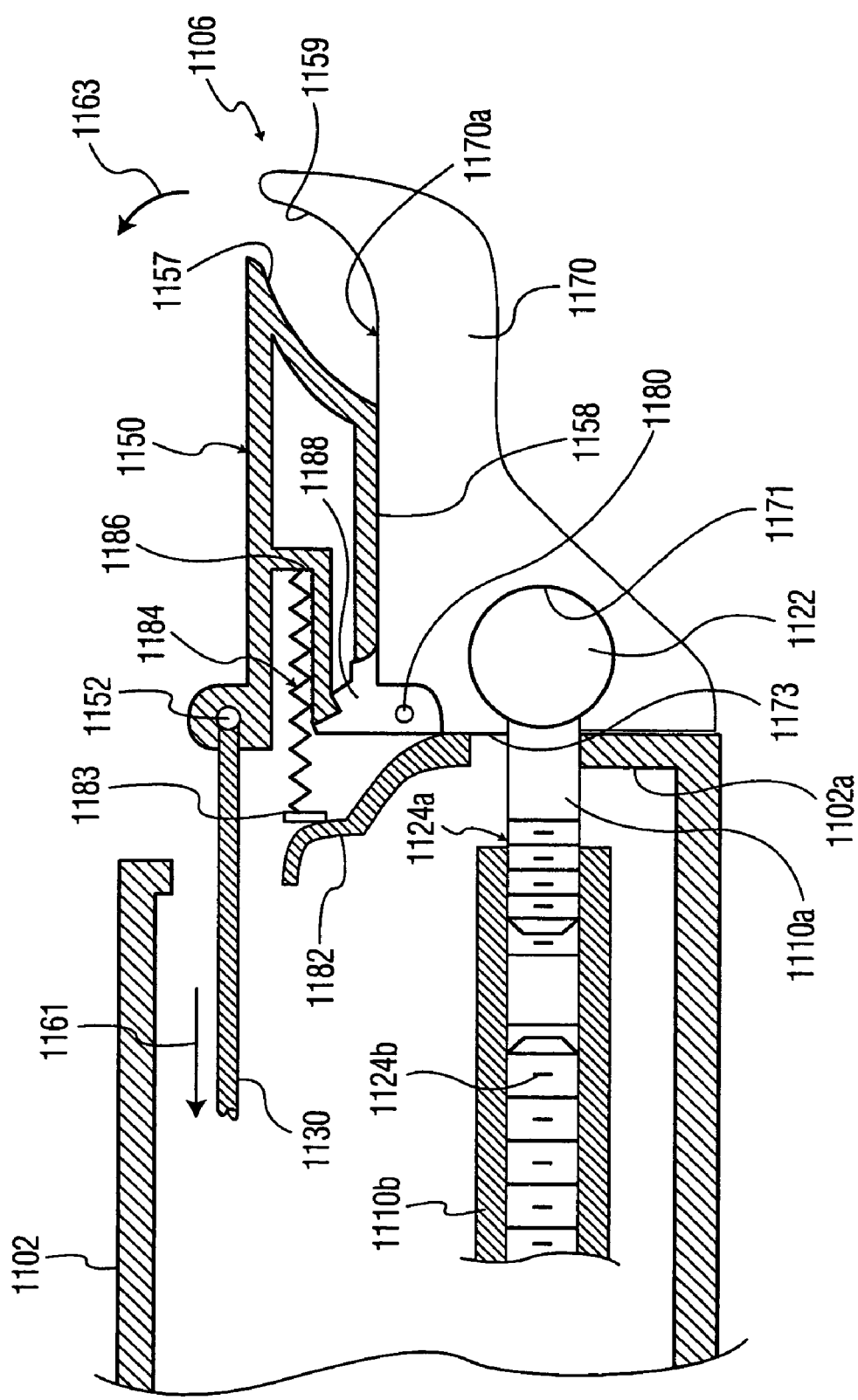
FIG. 89 is a more detailed fragmented sectional elevation view of the rongeur head and shaft portion of the instrument of FIG. 86.

A rongeur head 1106, FIGS. 86 and 89, is attached at a distal end of the instrument 1100. The rongeur is coupled to the distal end of the shank 1110 by coupling assembly 127. The coupling assembly 1120, FIGS. 87, 88 and 89 includes a circular cylinder 1122, forming a male joint member. The cylinder 1122, FIG. 87, is connected to a rod 1110a threaded at one end with threads 1124*a*. The shank 1110 is threaded at its distal end by threads 1124*b*, FIG. 88. A tubular coupling member 1110*b* has a threaded bore that is threaded to the shank 1110 distal end threads 1124*b* and to the threads 1124*a*, FIG. 89, on the end of the rod 1110*a*.

The distal end of the body 1102 has an end wall 1102*a* that is planar and an apertured wall 1102*b* that is contoured as shown, FIGS. 88 and 89.

The male joint member 1122 attaches to a mating cavity 1171 in rongeur lower jaw 1170, FIG. 89. The lower jaw 1170 cavity 1171 is circular cylindrical which receives the male cylindrical member 1122. The jaw 1170 has a planar anvil surface 1170*a*. The jaw 1170 has a second planar wall surface 1173 which abuts the body planar wall 1102*a*. Surfaces 1173 and 1170*a* are normal to each other. The jaw 1170 has a pivot bore which receives a pivot pin 1180. The contoured wall 1102*b* of the body curves away from the surface 1173 into arcuate wall portion 1182 that terminates spaced from outer cylindrical wall 1102*c* of the body 1102 forming opening 1175 in the wall 1102*b*.

The instrument 1100 further includes a filament 1130 attached to an actuation member 1134 at connection point 1134*a*. The actuation member 1134 pivots about a pivot pin 1134*b* attached to an extension 1134*c* of the body 1102 in the body interior cavity. The member 1134 is positioned adjacent to the proximal end of the body 1102.

Upper jaw 1150 pivots about pivot pin 1180 and has tissue cutting edges 1157 and 1158. Edge 1158 abuts the surface 1170*a* of the lower jaw and edge 1157 is spaced from arcuate surface 1159 of the lower jaw. The filament 1130 is attached to the upper jaw at connection point 1152 such that movement of the actuation member 1134 toward the distal end of the instrument, as shown by arrow 1160, FIG. 88, moves the filament towards the proximal end of the instrument. This action is shown by arrow 1161, FIG. 89, which pivots the upper jaw 1150 about pivot pin 1180 in the direction 1163.

The upper jaw element 1150 is biased to resist rotation by the filament 1130 by spring 1184. The spring biases the upper jaw to remain in it's at rest position FIG. 89. The spring 1184 is positioned between and connected to upper jaw wall 1186 and to the body 1102 wall 1182. Rotation of the upper jaw element 1150 in direction 1163 compresses the spring 1184. The spring resiliently returns the upper jaw element to it's at rest position as the actuation member 1134 is returned to it's initial position.

The lower jaw element 1170 matingly abuts the upper jaw element as shown in FIG. 89, and provides a cutting surface 1170*a* which cooperates with the edge 1158. The lower jaw element 1170 is locked into position by turning the knob 1104 and threading a threaded end 1110*b* of the shank 1110 into mating internal threads of the knob 1104. The abutment portion 1104*a* of the knob 1104 contacts the proximal end wall 1102*b* of the body 1102 and pulls the shank 110 to the left in the direction of arrow 1161. Thus the lower jaw wall 1173 is pulled into locking abutment with the distal end wall 1102*a* of the instrument 1100 body 1102 via the cylindrical element 1122.

The locked position of the lower jaw element 1170 allows the upper jaw element 1150 to more forcefully bear down on the cutting surface 1170*a* than if the lower jaw element movingly responded to the force of the upper jaw element.

Figure 90:
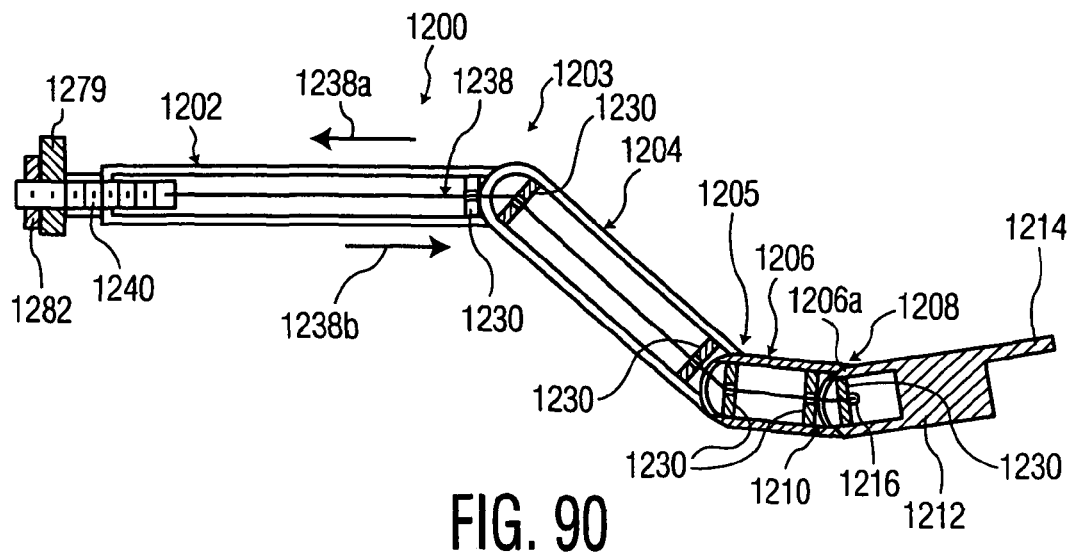
FIG. 90 is a side elevation sectional view of an instrument according to a further embodiment.

An articulated surgical instrument 1200 according to a further embodiment of the invention is shown in FIG. 90. The articulated surgical instrument 1200 includes a first tubular segment 1202 adjacent a proximal end of the instrument 1200. A second tubular segment 1204 is positioned between the first segment 1202 and a third tubular segment 1206 is positioned at a distal end of the articulated surgical instrument 1200. While three tubular segments are shown, more or fewer segments may be used according to a given implementation.

Articulation joint 1203 connects segments 1202 and 1204, and articulation joint 1205 connects segment 1204 and segment 1206. Articulation joint 1208 connects the third segment 1206 with a head 1212. Each articulation joint comprises a female concave spherical surface on the end of one segment and a convex complementary spherical surface on the end of the adjacent segment.

The first segment 1202 includes a female joint element which is a concave spherical surface at joint 1203. The second segment 1204 has a complementary male convex spherical surface at joint 1203 and a female concave spherical surface at its other end at joint 1205. The third segment 1206 has a male spherical convex surface complementary to and engages a female concave spherical surface at the mating end of segment 1204 at joint 1205. The other opposite end of segment 1206 is female and the mating joint element of the tool head at joint 1208 is a male spherical surface.

Figure 91:
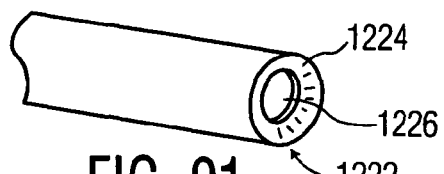
FIGS. 91 and 94 are respective isometric views of a representative shaft section end female face region showing a shaft section or head receiving configuration, FIG. 94 showing the configuration in more detail.
Figure 94:
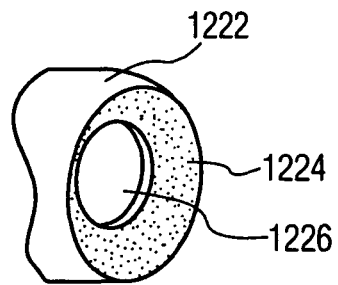
Figure 95:
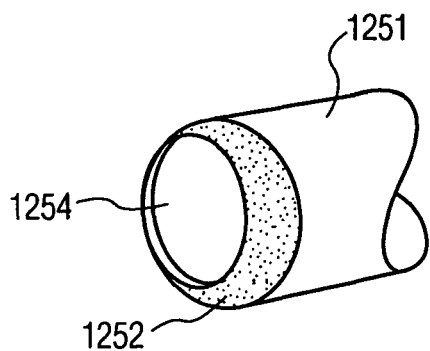
FIGS. 95 and 97 are respective isometric views of a representative shaft section end male face region, which mates with the female region of FIGS. 91 and 94, FIG. 95 showing the configuration in more detail.
Figure 96:
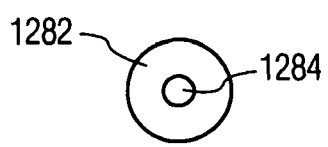
FIG. 96 shows a front elevation view of an adjustment knob locking member used with the instrument of FIG. 90.
Figure 97:
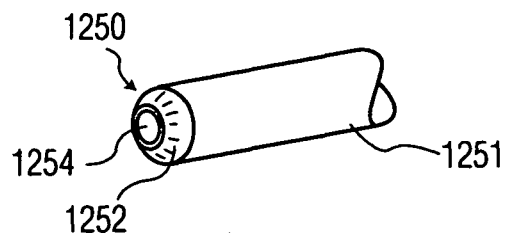
Figure 98A:
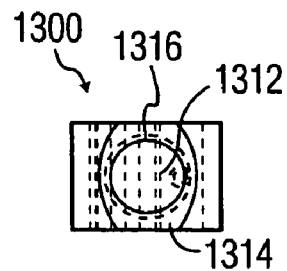
FIGS. 98a-98e are respective rear elevation, top plan, front elevation, side elevation and isometric views of a spinal implant insertion head according to an embodiment of the present invention.
Figure 98B:
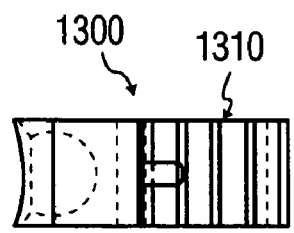
Figure 98C:
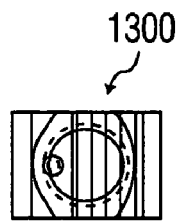
Figure 98D:
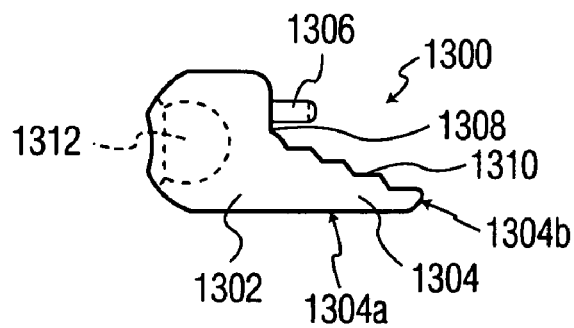
Figure 98E:
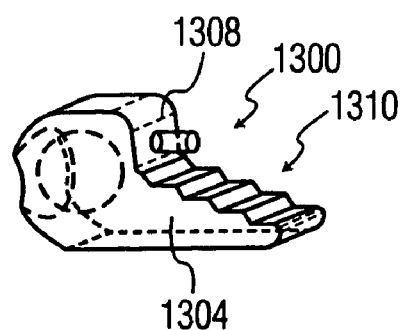
Figure 99A:
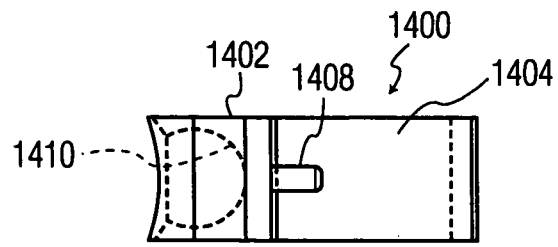
FIGS. 99a-99e are respective top plan, rear elevation, side elevation, front elevation, and isometric views of a spinal implant insertion head according to a further embodiment of the present invention.
Figure 99B:
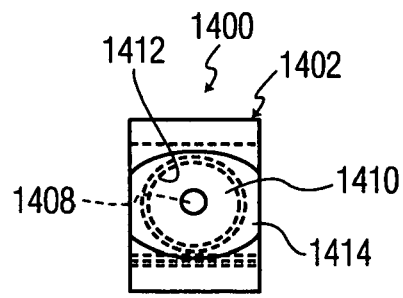
Figure 99C:
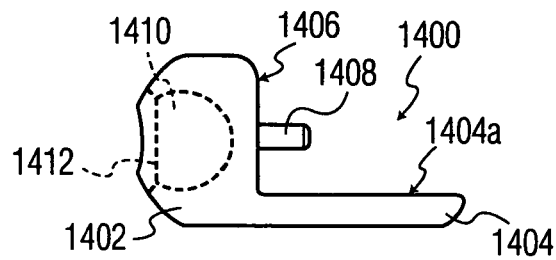
Figure 99D:
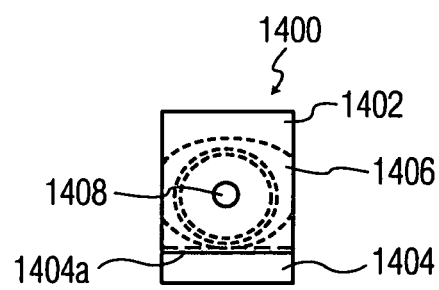
Figure 99E:
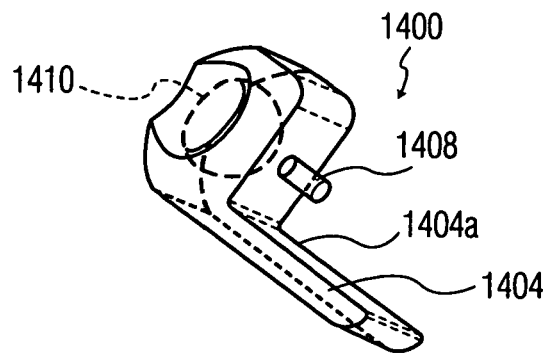

A representative male joint element 1251 is shown in FIGS. 95 and 97 which includes a spherical convex surface 1252 defining a central opening 1254. A representative female joint element 1222 is shown in FIGS. 91 and 94 and includes a spherical concave surface 1224 defining a central opening 1226. The male joint surface 1252 mates with the female joint surface 1224 and are complementary. Both surfaces 1224, 1252 are rough to provide a locking friction fit between the surfaces.

A representative female receiving joint element 1222 is shown in FIGS. 91 and 94. The element 1222 is located at the distal end of the third segment 1206, for example, or of any of the other segments, and has a concave spherical surface 1224 and an opening 1226.

The head 1212 includes a representative male joint element. The male joint element 1251 is cylindrical, terminates at a spherical convex surface 1252 relative to a longitudinal axis and defines an opening 1254. The male joint element 1251 is at a proximal end of the head 1212 and includes a spherical convex surface 1210 as described above for all of the segments. The surface 1210 mates with the corresponding female joint element of the third segment 1206 as described above with representative elements 1222 and 1251 shown in FIGS. 91 and 97.

The head 1212 shown in FIG. 90 has a cantilevered distal rectangular leg portion 1214. A filament 1238 is connected at point 1216 to the head. The male surface 1206*a* and the female surface 1210 matingly abut and provide cooperating engagement of the third segment 1206 and the head 1212 for relative articulation of the head 1212.

Figure 92:
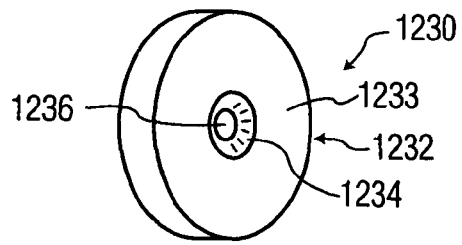
FIGS. 92 and 93 are respective isometric and side elevation sectional views of a representative filament guide used in the instrument of FIG. 90.

A representative filament guide member 1230 is shown in FIG. 92. The guide member 1230 includes a disc shaped body 1232 having an opening 1236 defined by a rounded smooth U-shaped surface 1234. A guide member 1230 is located at each male and female end of each segment.

Figure 93:
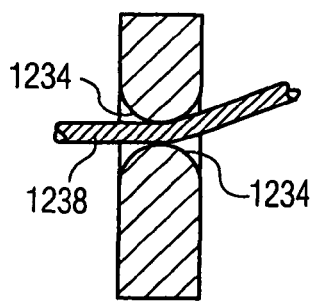

The filament 1238 is passed through the openings 1236 of each guide member in each segment and connected to a threaded rod 1240 at the proximal end of the instrument 1200. As shown in greater detail in FIG. 93, the filament 1230 passes through the opening 1236 formed by the convex rounded surfaces 1234.

The convex surfaces 1234 provide smooth non-abrading interaction with the filament 1238 as the filament displaces through the guides. The threaded element 1240 threads into a mating threaded hole in an adjustment knob 1279, and into threaded engagement with locking knob 1282. The knob 1279 when rotated pulls the filament 1238 taught, fixing the segments 1202, 1204, 1206 and the head 1212 one to another in any desired relative orientation within the range of motion of the male and female spherical surfaces of each joint. The locking knob 1282 locks the knob 1279 at a desired threaded location.

A spinal implant insertion head 1300 is shown in FIGS. 98a-98e. The implant insertion head 1300 includes a body 1302 having a cantilevered portion 1304. A stud 1306 extends from a distal end wall 1308. The distal end wall is contiguous with a stepped surface 1310 of the cantilevered portion 1304 of the implant insertion head 1300. The stepped surface 1310 and a bottom wall 1304a are joined via an arcuate edge 1304b. The body 1302 of the insertion head 1300 includes a spherical cavity 1312. A concave surface 1314 extends radially about a longitudinal axis and defines an opening to the cavity 1312. The spherical cavity 1312 receives a mating ball (not shown) to create an articulation joint such that the head 1300 can be moved to any desired angle.

Another spinal implant insertion head 1400 is shown in FIGS. 99a-99e. The implant insertion head 1400 includes a body 1402 having a cantilevered portion 1404 extending distally with a planar surface 1404a. The head 1400 further includes a distal planar surface 1406 which is perpendicular to the cantilevered portion 1404. A stud 1408 extends from the distal surface 1406 and is in parallel spaced relation with the cantilevered portion 1404. The stud is closely received in an implant bore such as the bores 104, 113, 131 and so on of the implants discussed previously in FIGS. 16-24 among others and assists in holding the implant to the head and orient the implant to the head.

The body 1402 of the insertion head 1400 includes a spherical cavity 1410 and an opening 1412 to the cavity 1410 defined by a concave surface 1414 at the proximal end of the body 1402. The spherical cavity 1410 is configured to receive a ball (not shown) so that an articulating joint is created by the mating of the ball and the spherical cavity 1410.

Figure 100A:
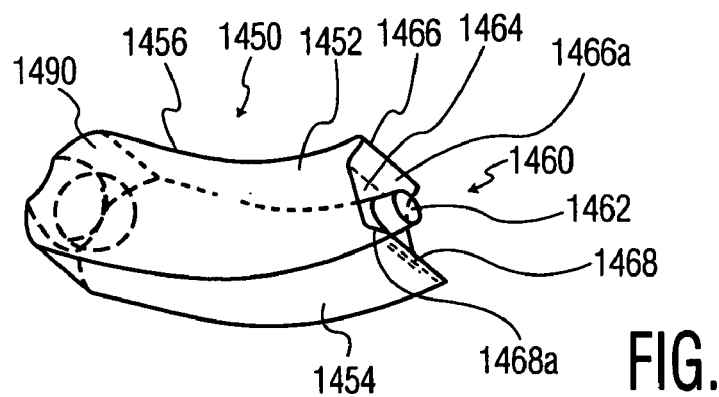
FIGS. 100a-100e are respective isometric, rear elevation, top plan, side elevation and front elevation views of a spinal implant insertion head according to a further embodiment of the present invention.
Figure 100B:
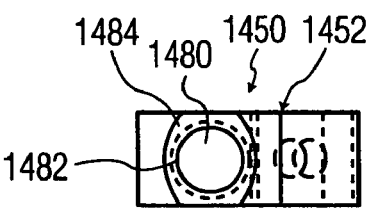
Figure 100C:
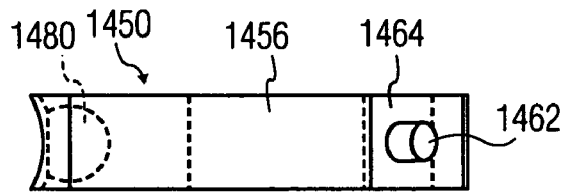
Figure 100D:
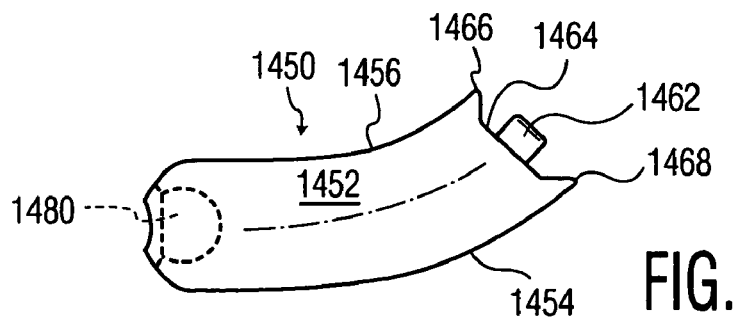
Figure 100E:
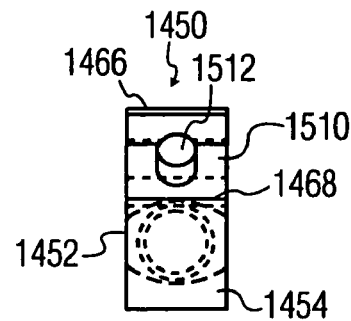
Figure 101A:
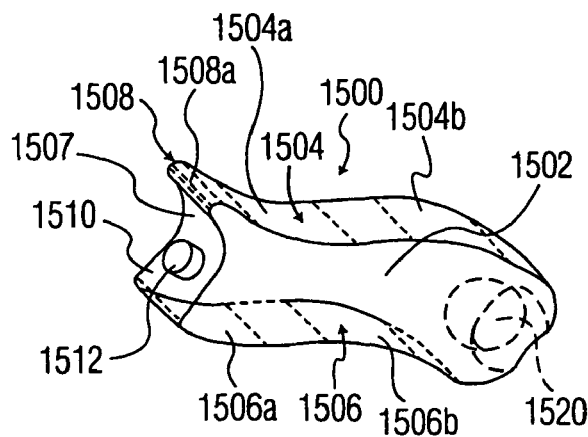
FIGS. 101a-101e are respective isometric, rear elevation, side elevation, front elevation and top plan views of a spinal implant insertion head according to a further embodiment of the present invention.
Figure 101B:
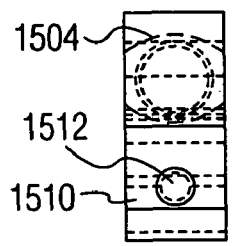
Figure 101C:
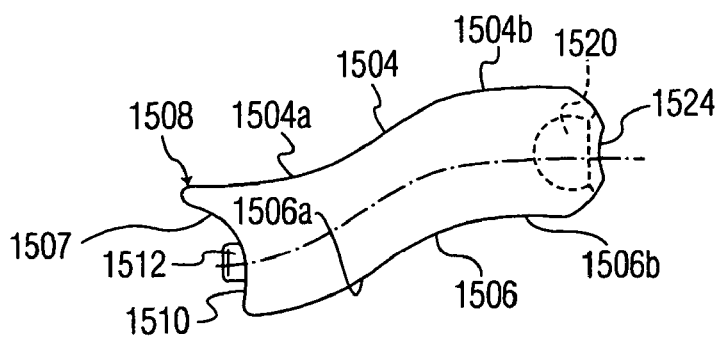
Figure 101D:
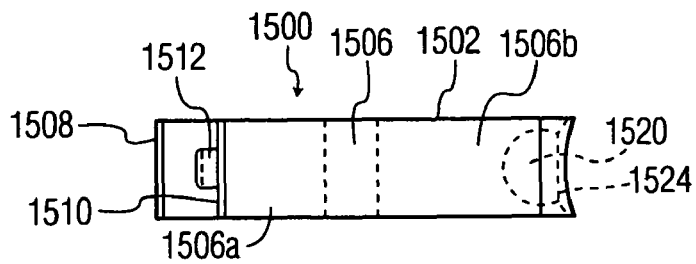
Figure 101E:
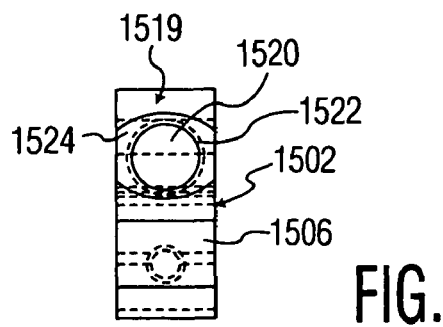

A further spinal implant insertion head according to the present invention is shown in FIG. 100a-100e. The insertion head 1450 includes a curved body 1452 having a convex side wall 1454 and a concave side wall 1456 opposite one another. The head 1450 includes a distal end 1460 having a stud 1462 extending from a distal surface 1464 of the body 1452. Two distally extending walls 1466 and 1468 are in spaced relation to each other and extend contiguously with the side walls 1456 and 1454. The distally extending walls 1466 and 1468 include angled surfaces 1466a and 1468a. The head 1450 also includes a spherical cavity 1480 in the body 1452, as shown in FIG. 100b. The cavity 1480 has an opening 1482 defined by a convex surface 1484 in the body proximal end wall 1490. The surface 1464 and the extending walls 1466 and 1468 inclined surfaces form a recess that is complementary to outer surfaces on the received implant.

A further spinal implant insertion head 1500 according to the present invention is shown in FIGS. 101a-101e. The head 1500 includes a body 1502 having side walls 1504 and 1506. Each side wall 1504, 1506 includes concave segments 1504a, 1506b and convex segments 1504b, 1506a, respectively. The concave and convex segments of each wall are in mirror image relation to each other. The side wall 1504 includes a cantilevered portion 1508 extending distally past a end wall 1510 and having an arcuate inner surface 1507 and edge 1508a connecting the end wall 1510 to the side wall 1504. A stud 1512 extends distally from the end wall 1510. At the opposite end wall 15 the body 1502 has a spherical cavity 1520, FIG. 101e. The opening 1522 of the cavity 1520 is defined by a concave surface 1524. The cantilever portion 1508 and walls 1507 and 1510 are shaped complementary to the received implant (not shown). The spherical cavity 1520 in this and the above described implants receive a ball of a male joint element (not shown) to secure the implant to an instrument of the types described above. The just enumerated implant insertion heads are interchangeable with the male joint element, forming a ball joint therewith, of each corresponding instrument for the insertion of different shaped implants with a common instrument.

A further embodiment of a spinal implant insertion head according to the present invention is shown in FIGS. 102a-102e. The implant insertion head 1550 includes a body 1552 and a distal end 1554 having opposing walls 1556 and 1558 in spaced relation to each other. The walls 1556, 1558 define channel 1560 therebetween. A distal end wall 1562, between the walls 1554 and 1558, has a stud 1564 extending therefrom and preferably spaced equally from the side walls 1556, 1558. The side walls 1556 and 1558 extend contiguously with the side walls 1566 and 1568, respectively. This head receives the implant 180 of FIG. 24 for example.

Figure 102A:
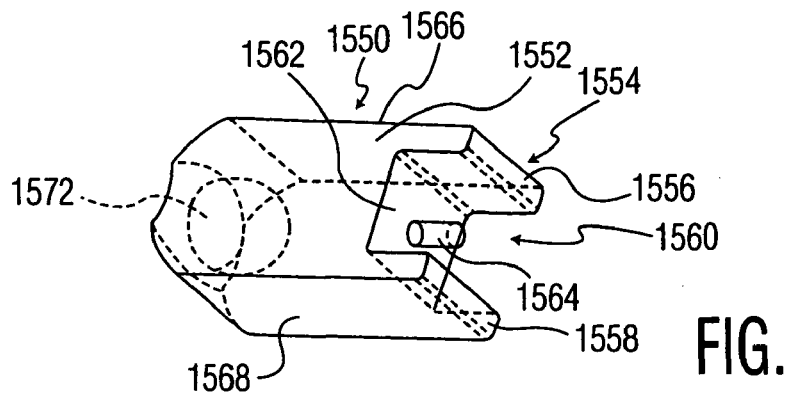
FIGS. 102a-102e are respective isometric, top plan, rear elevation, side elevation, and front elevation views of a spinal implant insertion head according to a still further embodiment of the present invention.
Figure 102B:
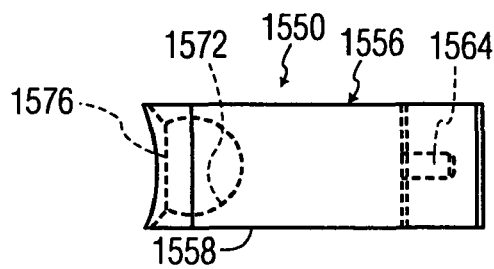
Figure 102C:
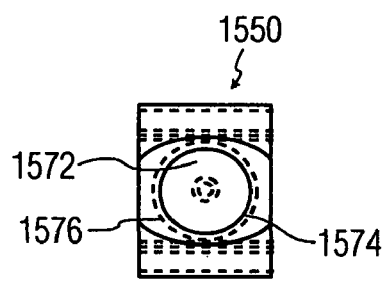
Figure 102D:
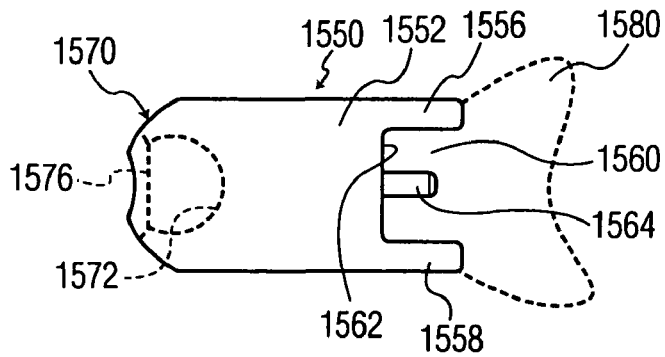
Figure 102E:
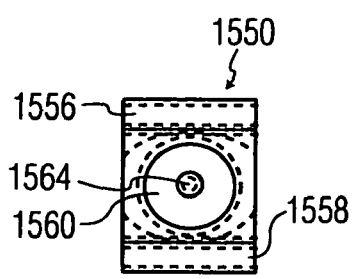

Opposite the distal end of the head 1550 is the proximal end wall 1570 of the head 1550. The body 1552 defines a spherical cavity 1572 having an opening 1574 in the distal end wall 1570 of the body 1552 defined by a concave surface 576. The cavity 1572, like the other spherical cavities of the heads described above, receives an articulating ball to form a ball joint (not shown) such as the compressible ball, for example, shown in FIG. 31. The phantom line of an implant 1580 such as that of FIG. 24 is shown in FIG. 102d which has a bore that closely mates with the stud 1564 in the channel 1560.

Figure 103A:
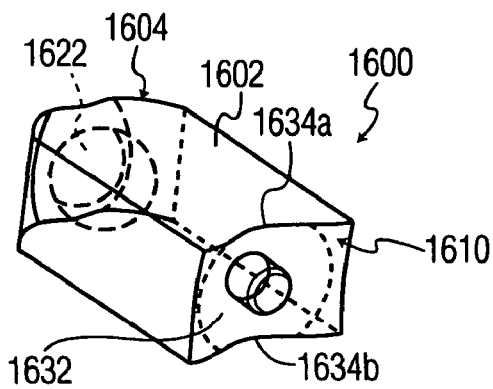
FIGS. 103a-103e are respective isometric, front elevation, top plan, rear elevation and side elevation views of a spinal implant insertion head according to a further embodiment of the present invention.
Figure 103B:
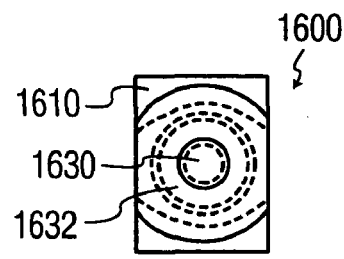
Figure 103C:
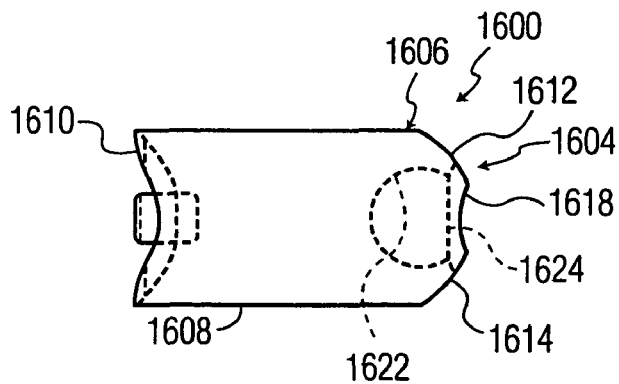
Figure 103D:
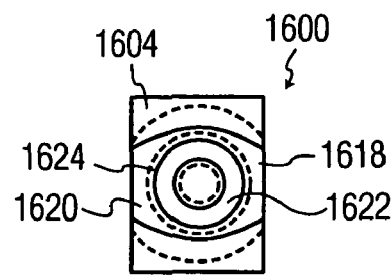
Figure 103E:
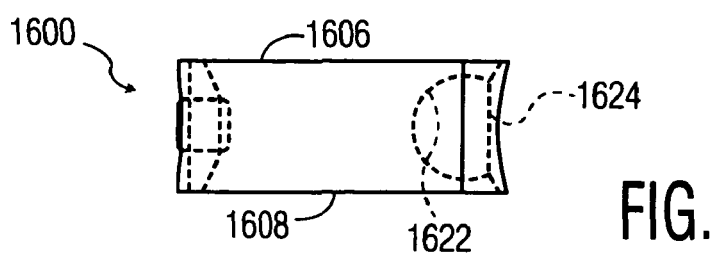

A further embodiment of a spinal implant insertion head 1600 according to the invention is shown in FIGS. 103a-103e. The head 1600 includes a body 1602 having a proximal end wall 1604, two side walls 1606 and 1608 and a concave distal end wall 1610. The proximal end wall 1604 has a convex surface 1612 contiguous with the side wall 1606, and a second concave surface 1614 contiguous with the opposing side wall 1608. Between the convex side walls 1612 and 1614 is a concave surface 1618. The proximal wall 1604 is shown in FIG. 103d and the body 1602 defines a spherical cavity 1622 having an opening 1624 in the concave surface 1618. The distal wall 1610 is shown in FIG. 103b, and has a stud 1630 that extends perpendicularly from the distal wall 1610. Concentrically surrounding the stud 1630 is a concave surface 1632. The distal wall 1610 includes a concave edge portion 1634a along the top edge and a mirror image concave edge portion 1634b along the bottom edge of the wall 1610.

Another embodiment of a spinal implant insertion head 1700 according to the present invention is shown in FIGS. 104a-104e. The head 1700 includes a body 1702 having opposing side walls 1704 and 1706, a distal end 1708, and a proximal end 1710. The distal end includes a wall edge 1712 extending contiguously from the side wall 1704. Planar end wall 1714 is contiguous with a curved wall terminating at an edge 1712 extending distally therefrom and has a stud 1718 extending therefrom. The planar wall 1714 is also contiguous with an inclined cantilevered wall section 1720 which terminates at an arcuate edge 1720a contiguous with the bottom side wall 1706. The wall 1714, section 1720 and the wall terminating at edge 1712 form a recess which receives a complementary shaped implant.

Figure 104A:
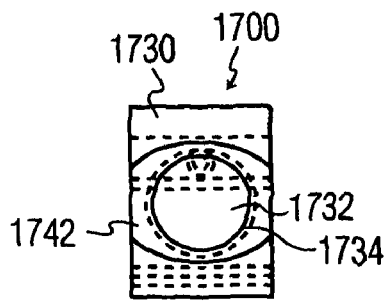
FIGS. 104a-104e are respective rear elevation, isometric, side elevation, front elevation and top plan views of a spinal implant insertion head according to a further embodiment of the present invention.
Figure 104B:
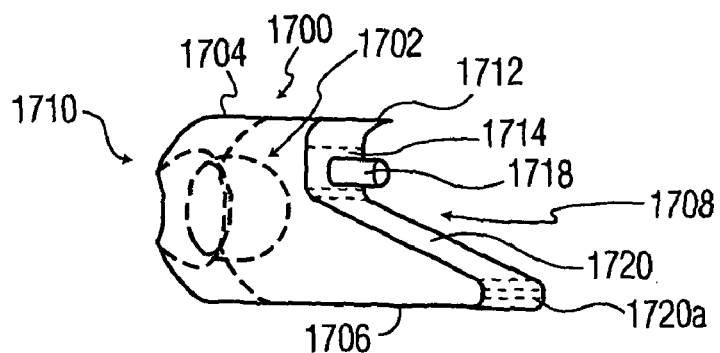
Figure 104C:
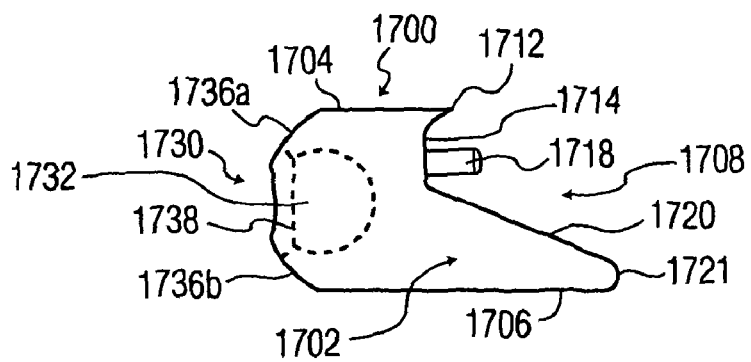
Figure 104D:
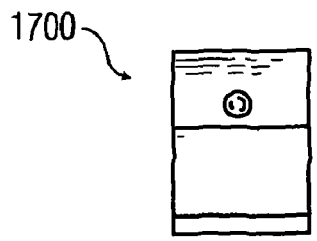
Figure 104E:
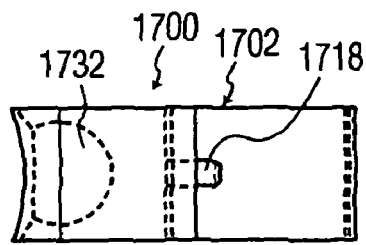

A proximal end wall 1730 shown in FIG. 104e includes an upper convex surface 1736a and a lower convex surface 1736b, and a concave surface 1738 between the upper and lower convex surfaces 1736a and 1736b. The body 1702 defines a spherical cavity 1732 having an opening 1734 for receiving a ball of a connecting joint element to form a ball joint therewith. A concave surface area 1742 defines the opening 1734, as shown in FIG. 104a. The head is interchangeable with the other heads described above in a given instrument as described above.

Figure 105A:
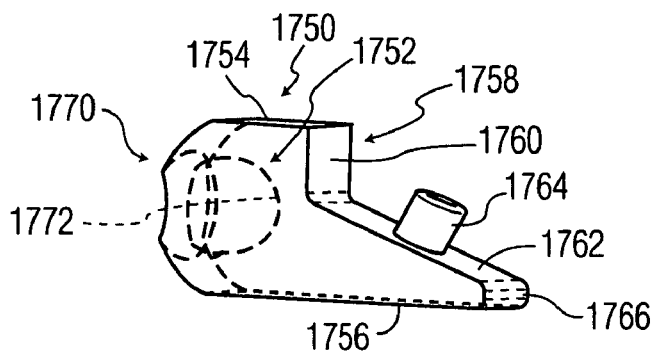
FIGS. 105a-105e are respective isometric, top plan, rear elevation, side elevation and front elevation views of a spinal implant insertion head according to a further embodiment of the present invention.
Figure 105B:
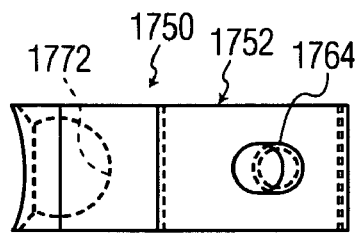
Figure 105C:
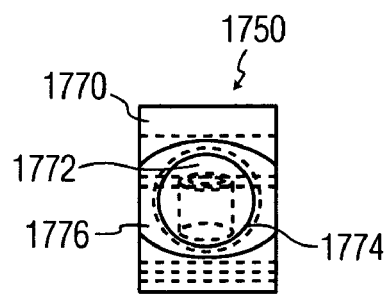
Figure 105D:
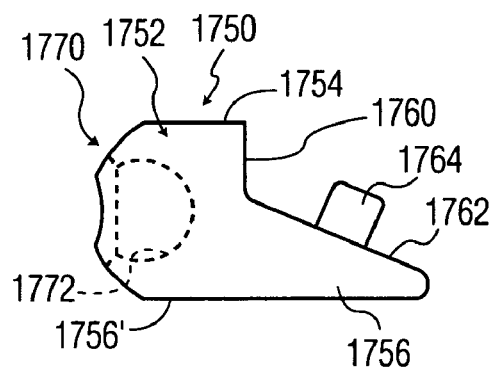
Figure 105E:
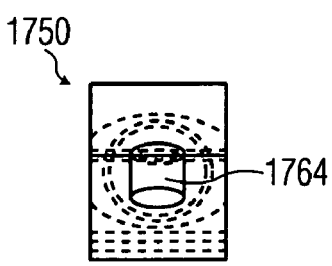

Another embodiment of a spinal implant insertion head 1750 according to the invention is shown in FIGS. 105a-105e. The head 1750 includes a body 1752 having top and bottom walls 1754 and 1756. The body 1752 also includes a distal wall 1758 having a planar vertical surface 1760 contiguous with top wall 1754 and perpendicular thereto. The distal wall 1758 has a cantilevered segment 1762 extending therefrom and having an inclined surface 1762. A stud 1764 extends perpendicularly from the inclined segment 1762, but is at an angle with respect to the plane coincident with the bottom wall 1756 bottom surface 1756'. The inclined portion contiguously extends to the bottom wall 1756 meeting at an arcuate edge 1766. The opposite, proximate wall 1770 includes a spherical cavity 1772 having an opening 1774, as shown in FIG. 105c. A concave surface 1776 defines the opening 1774. This head like the others is interchangeable with those heads with respect to a given instrument.

Figure 106:
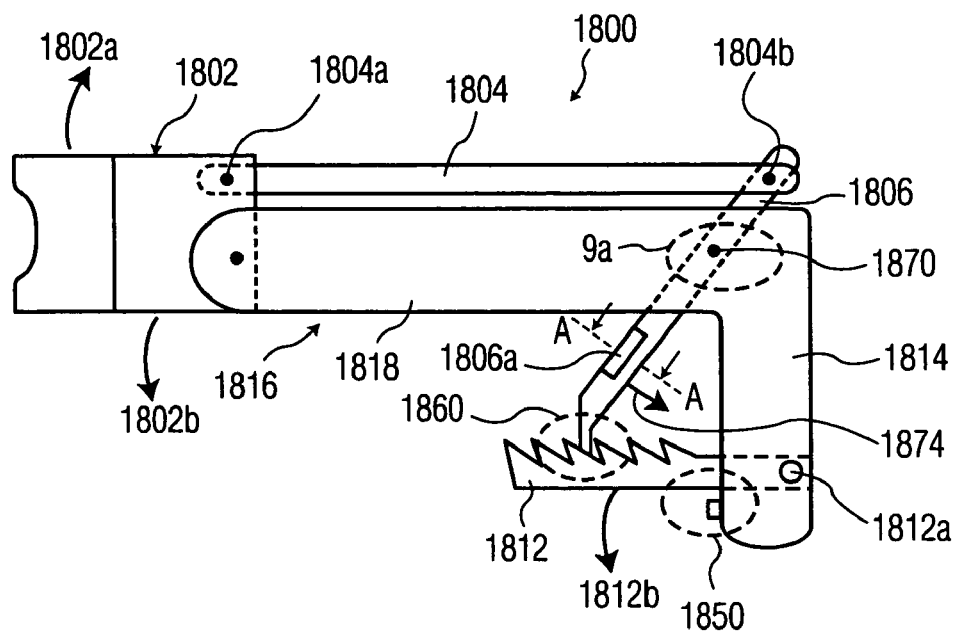
FIG. 106 is a side elevation of an instrument according to a further embodiment of the present invention.
Figure 107:
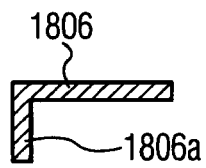
FIG. 107 is a sectional view of the instrument of FIG. 106 taken at lines A-A.
Figure 108:
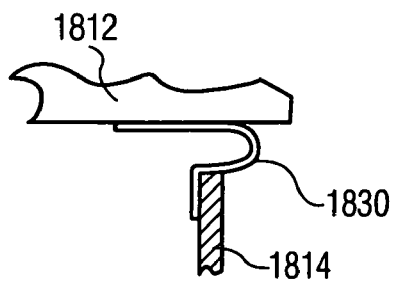
FIG. 108 is a more detailed view of the region 1850 of FIG. 106.

An embodiment of a further surgical instrument 1800 according to the present invention is shown in FIG. 106. The instrument includes a trigger mechanism substantially similar to that disclosed in the U.S. Pat. No. 5,660,333, which is hereby incorporated by reference. A tamp head 1802 is connected to an upper arm 1804 at pivot point 1804a. The upper arm is pivotally connected to a second (trigger) arm 1806 at pivot point 1804b. A cross section of the second arm 1806 is shown in FIG. 107 depicting the angularly extending finger tab 1806a.

A lower arm 1816 is "L" shaped and includes a first segment 1818 parallel with the upper arm 1804 and a second segment 1814 perpendicular to the first segment 1818. The second segment 1814 forms a handle for the instrument and is connected to a ratchet toothed member 1812 at pivot point 1812a.

Figure 109:
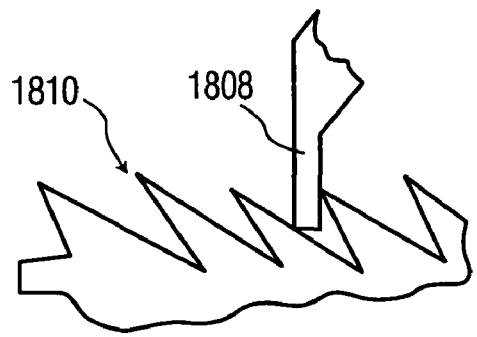
FIG. 109 is a more detailed view of the region 1860 of FIG. 106.

The member 1812 extends perpendicularly from the second segment and parallel to the upper arm 1804 and first segment 1818 of the lower arm. The member 1812 is urged upwardly in the figure toward the member 1806 by a resilient "U" shaped spring 1830 which abuts a bottom surface of the member 1812 and is connected to the second segment 1814. The second arm 1806 includes a pawl 1808 for engaging a selected one of a plurality of an array of ratchet teeth 1810 on member 1812, as shown in FIG. 109. The ratchet teeth 1810 hold the trigger arm 1806 in a given angular position. The arms 1804, 1818, 1806 and head 1802 form a four bar linkage.

Figure 111:
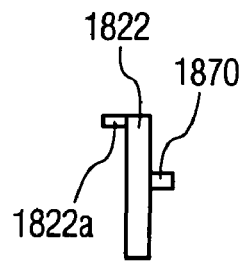
FIG. 111 is a side elevation view of a member which attaches the spring of FIG. 112 to the trigger of FIG. 110.
Figure 112:
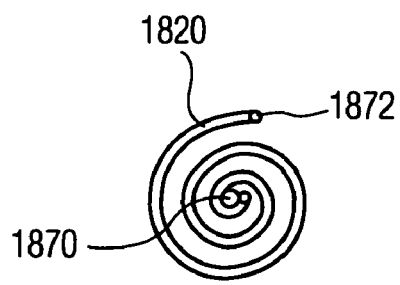
FIG. 112 is a side elevation view of a torsion spring for use with the member of FIG. 111 to bias the trigger in a neutral quiescent position.

The center of a torsion spring 1820 is pinned to pivot element 1870, shown in region 9a in FIG. 106, and the end 1872 of the torsion spring abuts or is fixed to the second arm 1806. A portion of the arm 1806 is shown in FIG. 111. The pivot element 1870 is shown in FIG. 111. Member 1822 is fixed to the first segment 1818 by pin 1822a.

Figure 110:
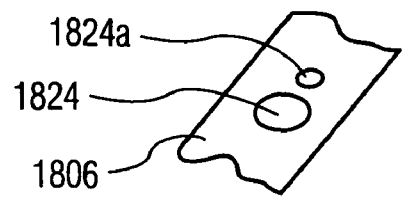

FIG. 110 shows a portion of the second arm 1806 at region 9a of FIG. 106 depicting a first hole 1824 for receiving the pivot element 1870, and a second hole 1824a for receiving the end 1872 of the spring 1820. Thus, the trigger arm 1806 is biased in the direction shown by arrow 1874, FIG. 106. The member 1812 is supported by the resilient "U" shaped element 1830 which allows the member 1812 to be pulled downward to release the pawl 1808 from the teeth 1810. The torsion spring 1820 bias advances the pawl 1808 in the direction of arrow 1874 when the member 1812 is pulled down to release the pawl 1808 from the teeth 1810. The arm 1806 and pawl 1808 can be pulled in the opposite direction using the tab 1806a.

When the pawl 1808 is moved between ratchet teeth, the upper arm 1804 moves forward or rearward (left and right in the figure) along a plane parallel to the first segment 1818 of lower arm 1816. The head 1802 thereby moves arcuately as indicated by arrows 1802a and 1802b in response to the upper arm 1804 movement. Other heads or tools may be attached to the instrument in place of head 1802 or head 1802 may be configured to have a male or female joint as described above in connection with certain of the embodiments for receiving various interchangeable processing heads.

It will occur to one of ordinary skill that various modifications may be made to disclosed embodiments. The various embodiments are given by way of illustration not limitation. It is intended that the appended claims define the invention.

What is claimed is:

1. A surgical instrument for processing an intervertebral disc space and/or for insertion of a spinal implant into the processed space comprising:
   a shaft having a first axis;
   a first joint element coupled to the shaft; and
   at least two different heads for said processing and/or insertion, each of the different heads for selective attachment to the shaft, each head having a second longitudinal axis and a second joint element which mates with the first joint element, the first and second joint elements forming a joint for attaching each selected head to the shaft,
   wherein the at least two different heads are selected from a group consisting of any two different head configurations, the configurations forming categories, each category having one or more different configurations, the categories including a chisel, an implant gripping head, an implant impacting head, an implant inserter, a rasp, a distractor, a trial, a curette and a rongeur;
   wherein the joint is configured for permitting pivoting of the second longitudinal axis of each selected head in at least three directions relative to the first axis, and
   wherein the second longitudinal axis is collinear with the first axis in at least one orientation of the selected head.

2. The surgical instrument of claim 1 wherein the first and second joint elements are mating complementary first and second articulation elements to permit articulation of one of the at least two heads relative to the shaft.

3. The surgical instrument of claim 2 wherein the first articulation element comprises one of a ball, cylinder, or socket and the second articulation element has a configuration complementary to the respective one ball, cylinder or socket for releasably and movably mating to the respective one ball, cylinder or socket.

4. The surgical instrument of claim 3 wherein the cylinder or ball is attached to the shaft or one of the at least two heads, and the socket is mounted in the other of said shaft or one of the at least two heads.

5. The surgical instrument of claim 3 wherein the cylinder or ball is integral with the shaft or one of the at least two heads.

6. The surgical instrument of claim 3 wherein one of the at least two heads further includes a distal end opposite the second articulation element, the distal end having a cantilevered side wall extending from a distal end wall, and the distal end wall having a stud attached thereto extending substantially parallel to the cantilevered side wall.

7. The surgical instrument of claim 2 wherein one of the first or the second articulation elements includes an engagement member for releasably engaging the other articulation element, and the engagement member is adapted to allow angular positioning between the first and second articulation elements.

8. The surgical instrument of claim 1 further including a connection arrangement secured to the shaft for temporarily fixedly securing any of the selected heads to the shaft.

9. The surgical instrument of claim 8 wherein the connection arrangement is for securing the selected heads in any one of selected different orientations relative to the first axis.

10. The surgical instrument of claim 1 wherein the joint elements are configured for permitting each selected head to be positioned at any of a plurality of angular orientations relative to the first axis.

11. The surgical instrument of claim 1 wherein the at least two different heads are in the same or different categories.

12. The surgical instrument of claim 1 wherein the at least two different heads are in different categories.

13. The surgical instrument of claim 1, the first joint element comprising a ball extending from the shaft and the second joint element comprising a spherical socket complementary to and for receiving the ball in each of the at least two heads forming the second joint element, the rod being arranged for displacing the ball in opposite directions along the first axis for selective releasing the attached head or for fixedly securing the attached head to the shaft in a given one of said different orientations.

14. The surgical instrument of claim 1 wherein one head of the at least two heads is an implant inserter.

15. The surgical instrument of claim 14 wherein the one head has opposite first and second ends and the second joint element is a socket in communication with the first end, the second end having an implant engaging surface for engaging a first implant surface and an implant engaging projection extending from the first implant engaging surface for engaging a mating implant bore.

16. A surgical instrument for processing an intervertebral disc space and/or for insertion of a spinal implant into the processed space comprising:
a shaft having a first axis;
a first joint element coupled to the shaft; and
a head for said processing and/or insertion having a second longitudinal axis and a second joint element which mates with the first joint element, the first and second joint elements forming a joint for permitting pivoting of the second longitudinal axis of the head in at least three directions relative to the first axis,
wherein the head is of a configuration selected from the group consisting of chisels, implant gripping heads, implant impacting heads, implant inserters, rasps, distractors, trials, curettes, and rongeurs; and
wherein the second longitudinal axis is collinear with the first axis in at least one orientation of the head.

17. A surgical instrument for processing an intervertebral disc space and/or for insertion of a spinal implant into the processed space comprising:
a shaft having a first axis;
a first joint element coupled to the shaft;
a connection arrangement secured to the shaft; and
a head for said processing and/or insertion coupled to the shaft, the head having a second longitudinal axis and a second joint element which mates with the first joint element, the first and second joint elements forming a joint for coupling the head to the shaft;
wherein the head comprises a distal end comprising an arcuate implant receiving wall and an implant engaging member extending from said implant receiving wall;
wherein the joint is configured for permitting pivoting of the second longitudinal axis of the head in at least three directions relative to the first axis;
wherein the second longitudinal axis is generally collinear with the first axis in at least one orientation of the head; and
wherein the connection arrangement is adapted to fixedly secure the head in an orientation in which the second longitudinal axis is angled with respect to the first axis.

18. The surgical instrument of claim 17 wherein the head further comprises an end face opposite the implant receiving wall, the end face comprising one of a convex and a concave surface configured to mate with a complementary surface of the shaft.

* * * * *